United States Patent
Goure et al.

(10) Patent No.: US 9,320,793 B2
(45) Date of Patent: *Apr. 26, 2016

(54) METHOD FOR TREATING A DISEASE ASSOCIATED WITH SOLUBLE, OLIGOMERIC SPECIES OF AMYLOID BETA 1-42

(71) Applicants: Acumen Pharmaceuticals, Inc., Livermore, CA (US); Merck Sharp & Dohme Corp., Rahway, NJ (US)

(72) Inventors: William F. Goure, Livermore, CA (US); Franz F. Hefti, Livermore, CA (US); Renee C. Gaspar, West Point, PA (US); Paul J. Shughrue, West Chester, PA (US); Fubao Wang, Dresher, PA (US); Weirong Wang, West Point, PA (US); Ningyan Zhang, West Point, PA (US); Wei-Qin Zhao, North Wales, PA (US); Alexander McCampbell, Cambridge, MA (US); Min Xu, Ambler, PA (US)

(73) Assignees: Acumen Pharmaceuticals, Inc., Livermore, CA (US); Merck Sharp & Dohme Corp., Rahway, NJ (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/693,362

(22) Filed: Dec. 4, 2012

(65) Prior Publication Data

US 2013/0089537 A1 Apr. 11, 2013

Related U.S. Application Data

(63) Continuation-in-part of application No. PCT/US2011/043866, filed on Jul. 13, 2011.

(60) Provisional application No. 61/364,210, filed on Jul. 14, 2010.

(51) Int. Cl.
| | | |
|---|---|---|
| A61K 39/395 | (2006.01) | |
| C07K 16/18 | (2006.01) | |
| A61K 45/06 | (2006.01) | |
| A61K 39/00 | (2006.01) | |

(52) U.S. Cl.
CPC ............ *A61K 39/3955* (2013.01); *A61K 45/06* (2013.01); *C07K 16/18* (2013.01); *A61K 2039/505* (2013.01); *C07K 2317/24* (2013.01); *C07K 2317/55* (2013.01); *C07K 2317/565* (2013.01); *C07K 2317/76* (2013.01); *C07K 2317/90* (2013.01); *C07K 2317/92* (2013.01); *C07K 2317/94* (2013.01)

(58) Field of Classification Search
CPC .............. C07K 16/18; C07K 2317/24; C07K 2317/55; C07K 2317/56; C07K 2317/565; C07K 2317/76; C07K 2317/92; C07K 2317/94; A61K 2039/505; A61K 2300/00

See application file for complete search history.

(56) References Cited

U.S. PATENT DOCUMENTS

| | | | |
|---|---|---|---|
| 7,700,099 B2 | 4/2010 | Strohl ........................ 424/133.1 |
| 7,731,962 B2 | 6/2010 | Kinney et al. .............. 424/133.1 |
| 7,780,963 B2 | 8/2010 | Acton et al. ............... 424/133.1 |
| 7,811,563 B2 | 10/2010 | Acton et al. ............... 424/133.1 |
| 2004/0053313 A1* | 3/2004 | Gozes et al. ...................... 435/6 |
| 2005/0107472 A1* | 5/2005 | Wischik et al. ............... 514/553 |
| 2006/0057701 A1 | 3/2006 | Rosenthal et al. ......... 435/252.3 |
| 2006/0228349 A1* | 10/2006 | Acton et al. ............... 424/133.1 |
| 2007/0218499 A1 | 9/2007 | Lambert et al. ................ 435/7.1 |
| 2008/0175835 A1 | 7/2008 | Acton et al. ............... 424/130.1 |
| 2010/0028357 A1* | 2/2010 | Matsubara et al. ........ 424/139.1 |
| 2011/0269764 A1* | 11/2011 | Cohen et al. .................. 514/250 |

FOREIGN PATENT DOCUMENTS

| | | |
|---|---|---|
| WO | WO 2006/014478 A1 | 2/2006 |
| WO | WO 2006/055178 A2 | 5/2006 |
| WO | WO 2006/103116 A1 | 10/2006 |
| WO | WO 2007/050359 A2 | 5/2007 |
| WO | WO 2012/009442 A2 * | 1/2012 |

OTHER PUBLICATIONS

Gozes I (2011) NAP (davunetide) provides functional and structural neuroprotection. Curr. Pharm. Des. 17(10):1040-4; abstract only.*
Lannfelt L et al. (2008) Safety, efficacy, and biomarker findings of PBT2 in targeting Abeta as a modifying therapy for Alzheimer's disease: a phase IIa, double-blind, randomised, placebo-controlled trial. Lancet Neurol. 7:779-786.*
De Felice et al. "Alzheimer's Disease-type Neuronal Tau Hyperphosphorylation Induced by Aβ Oligomers" Neurobiology of Aging 2008 29(9):1334-1347.
Lee et al. "Targeting Amyloid-β Peptide (Aβ) Oligomers by Passive Immunization with a Conformation-selective Monoclonal Antibody Improves Learning and Memory in Aβ Precursor Protein (APP) Transgenic Mice" The Journal of Biological Chemistry 2006 281(7):4292-4299.
Rowan et al. "Mechanisms of the Inhibitory Effects of Amyloid β-Protein on Synaptic Plasticity" Experimental Gerontology 2004 39:1661-1667.
Shughrue et al. "Anti-ADDL Antibodies Differentially Block Oligomer Binding to Hippocampal Neurons" Neurobiology of Aging 2010 31(2):189-202.

* cited by examiner

*Primary Examiner* — Kimberly A. Ballard
(74) *Attorney, Agent, or Firm* — Licata & Tyrrell P.C.

(57) ABSTRACT

This invention is a method and kit for treating a disease associated with, or resulting from, the accumulation of soluble oligomer amyloid beta 1-42 using an antibody, or antibody fragment thereof, that has a higher affinity for amyloid beta 1-42 oligomers than for amyloid beta 1-42 monomer, amyloid beta 1-40 monomer, plaques and amyloid beta fibrils and, optionally, a tau therapeutic or an inhibitor of amyloid beta production or aggregation.

1 Claim, 14 Drawing Sheets

```
19.3_vh         EVQLVESGGGLVQPGGSLRLSCAASGFTFSSFGMHWVRQAPGKGLEWVAYISRGSSTYY
human_vh3-66    EVQLVESGGGLVQPGGSLRLSCAAS---------------WVRQAPGKGLEWVS----
                ************************                *************

19.3_vh         ADTVKGRFTISRDNAKNSLYLQMNSLRAEDTAVYYCARGITTALDYWGQGTLVTVSS
human_vh3-66    ----RFTISRDNSKNTLYLQMNSLRAEDTAVYYCAR---------------------
                    ******** ** ******************

19.3_vl         DVVMTQSPLSLPVTPGEPASISCRSSQSIVHSNGNTYLEWYLQKPGQSPQLLIYKASNRF
human_vk2-19    DIVMTQSPLSLPVTPGEPASISC----------------WYLQKPGQSPQLLIY----
                * *********************                **************

19.3_vl         SGVPDRFSGSGSGTDFTLKISRVEAEDVGVYYCFQGSRLGPSFGQGTKLEIL
human_vk2-19    -GVPDRFSGSGSGTDFTLKISRVEAEDVGVYYC--------------------
                 ******************************                    
```

*FIG. 6*

METHOD FOR TREATING A DISEASE ASSOCIATED WITH SOLUBLE, OLIGOMERIC SPECIES OF AMYLOID BETA 1-42

This application is a continuation-in-part application of PCT/US2011/043866, filed Jul. 13, 2011, which claims the benefit of priority from U.S. Provisional Patent Application Ser. No. 61/364,210, filed Jul. 14, 2010, the contents of which are incorporated herein by reference in their entireties.

BACKGROUND OF THE INVENTION

Alzheimer's disease (AD) is characterized by the progressive loss of cognitive function and the accumulation of amyloid beta (Aβ) plaques in regions associated with learning and memory. While Aβ plaques were once thought to play a central role in the pathogenesis of AD, a growing body of evidence suggests that soluble oligomeric species of Aβ may be responsible for the disease-associated neuronal dysfunction and cognitive decline (Walsh & Selkoe (2004) *Protein Pept. Lett.* 11:213-228; Selkoe (2008) *Behavioral Brain Res.* 192:106-113; Sakano & Zako (2010) *FEBS J.* 277:1348-58). Soluble, globular, non-fibrillar oligomeric species of Aβ, also referred to as Aβ-derived diffusible ligands (ADDLs; Lambert et al. (1998) *Proc. Natl. Acad. Sci. USA* 95:6448-53) or toxic soluble Aβ oligomers (Walsh, et al. (2002) *Nature* 416:535-539; Selkoe (2008) *Handb. Clin. Neurol.* 89:245-60), are abundant in AD, but not normal brains (McLean, et al. (1999) *Ann. Neurol.* 46:860-866; Gong, et al. (2003) *Proc. Natl. Acad. Sci. USA* 100:10417-10422). In vitro studies have shown that ADDLs, isolated from AD brain or synthetic preparations, bind to a subpopulation of cortical and hippocampal neurons (Gong, et al. (2003) supra; Klein, et al. (2004) *Neurobiol. Aging* 25:569-580; Lacor, et al. (2004) *J. Neurosci.* 24:10191-10200; Shughrue, et al. (2010) *Neurobiol. Aging* 31:189-202), while little or no binding is detected with fibrillar or monomer Aβ preparations (Lacor, et al. (2004) supra; Hepler, et al. (2006) *Biochemistry* 45:15157-15167). More specifically, ADDL binding has been demonstrated to be localized to the synapses of hippocampal neurons (Rammes, et al. (2011) *Neuropharmacol.* 60:982).

Furthermore, ADDL binding to neurons can be attenuated with both polyclonal (Gong, et al. (2003) supra) and monoclonal antibodies (Lee, et al. (2006) *J. Biol. Chem.* 281:4292-4299; De Felice, et al. (2007) *Neurobiol. Aging* 29:1334-1347; Shughrue, et al. (2010) supra) generated against ADDLs.

In rodent models, the central administration of ADDLs induces deficits in rodent long-term potentiation (LTP) and memory formation (Walsh, et al. (2002) supra; Cleary, et al. (2004) *Nat. Neurosci.* 8:79-84; Klyubin, et al. (2005) *Nat. Med.* 11:556-561). The effect of oligomers on LTP was attenuated when ADDLs were co-administered with an anti-Aβ antibody or administered to animals that were vaccinated with the Aβ peptide (Rowan, et al. (2004) *Exp. Gerontol.* 39:1661-1667). In a transgenic model of AD, such as transgenic mice that produce human amyloid precursor protein (hAPP), age-associated cognitive deficits have been observed with elevated ADDL levels (Westerman, et al. (2002) *J. Neurosci.* 22:1858-1867; Ashe (2005) *Biochem. Soc. Trans.* 33:591-594; Lee, et al. (2006) supra; Lesne, et al. (2006) supra). When hAPP mice were treated with an anti-Aβ oligomer antibody, a significant improvement in cognitive performance was observed without a concomitant decrease in Aβ plaque load (Lee, et al. (2006) supra). Together these findings suggest that ADDLs, and not Aβ plaques, are primarily responsible for cognitive impairment and that the use of anti-ADDL antibodies may prove efficacious in the treatment of AD. See also, U.S. Pat. Nos. 7,731,962, 7,780,963; WO 2007/050359; US 2007/0218499, WO 2006/014478; U.S. Pat. No. 7,700,099; US 2008/01758835, WO 2006/055178; and U.S. Pat. No. 7,811,563.

Accordingly, there is a need for ADDL-selective therapeutic antibodies for the prevention and treatment of AD. The present invention meets this need.

SUMMARY OF THE INVENTION

This invention is a method for treating a disease associated with or resulting from the accumulation of soluble oligomer amyloid beta 1-42 by administering to a subject in need thereof a dose of less than 10 mg/kg body weight of an antibody, or antibody fragment thereof, that has a higher affinity for amyloid beta 1-42 oligomers than for amyloid beta 1-42 monomer, amyloid beta 1-40 monomer, plaques and amyloid beta fibrils. In additional embodiments, the antibody also exhibits an affinity for amyloid beta 1-42 oligomers compared to amyloid beta 1-40 monomers in a competitive binding assay of at least 500:1; blocks binding of amyloid beta 1-42 oligomers to neurons; blocks incorporation of amyloid beta 1-42 oligomers into amyloid plaques; reverses acute amyloid beta 1-42 oligomer-mediated impairment of long-term potentiation; and/or provides improvement in cognitive testing as compared to a subject not receiving the antibody or antibody fragment. In certain embodiments, the antibody, or antibody fragment thereof, has (a) a light chain variable region comprising,
   (i) a CDR1 having the sequence Arg-Ser-Ser-Gln-Ser-Ile-Val-His-Ser-$Xaa_1$-Gly-$Xaa_2$-Thr-Tyr-Leu-Glu (SEQ ID NO:1), wherein $Xaa_1$ is Asn, Ser, Thr, Ala, Asp or Glu and $Xaa_2$ is Asn, His, Gln, Ser, Thr, Ala, or Asp,
   (ii) a CDR2 having the sequence Lys-Ala-Ser-$Xaa_1$-Arg-Phe-Ser (SEQ ID NO:2), wherein $Xaa_1$ is Asn, Gly, Ser, Thr, or Ala, and
   (iii) a CDR3 having the sequence Phe-Gln-Gly-Ser-$Xaa_1$-$Xaa_2$-$Xaa_3$-$Xaa_4$-$Xaa_5$ (SEQ ID NO:3), wherein $Xaa_1$ is Arg, Lys or Tyr, $Xaa_2$ is Val, Ala, or Leu, $Xaa_3$ is Pro, His, or Gly, $Xaa_4$ is Ala, Pro, or Val, and $Xaa_5$ is Ser, Gly, Arg or Phe; and (b) a heavy chain variable region comprising,
   (i) a CDR1 of SEQ ID NO:4,
   (ii) a CDR2 of SEQ ID NO:5, and
   (iii) a CDR3 of SEQ ID NO:6.

In other embodiments, the method of this invention includes the optional administration of an inhibitor of amyloid beta production, an inhibitor of amyloid beta aggregation and/or a tau therapeutic.

This invention also features a kit, which includes an antibody, or antibody fragment thereof, that has a higher affinity for amyloid beta 1-42 oligomers than for amyloid beta 1-42 monomer, amyloid beta 1-40 monomer, plaques and amyloid beta fibrils; and a second therapeutic, such as an inhibitor of amyloid beta production, an inhibitor of amyloid beta aggregation, a tau therapeutic, or a combination thereof.

BRIEF DESCRIPTION OF THE DRAWINGS

FIG. 6 shows the alignment of the heavy and light chain variable regions for anti-ADDL antibody 19.3 with a human germ line with the complementary determining regions (CDRs) indicated in bold type face. Antibody 19.3 heavy chain variable region (SEQ ID NO:7), antibody 3-66 human heavy chain variable region (SEQ ID NO:8), Antibody 19.3 light chain variable region (SEQ ID NO:9), antibody 3-66 human light chain variable region (SEQ ID NO:10).

FIG. 8A shows that the Aβ oligomers levels were four-fold higher in AD patients as compared to age-matched control, i.e., non-AD, patients in a blinded evaluation. The differences were statistically significant to p≤0.0004 as determined using a two-way t-test and Mann Whitney analysis of ranks, assuming the population was non-Gaussian. FIG. 8B shows that the Aβ oligomer levels were eight-fold higher in AD patients as compared to young control, i.e., non-AD, patients in a blinded evaluation. The differences were also statistically significant between these groups using the same statistical method as in FIG. 8A to a p-value≤0.0021.

FIG. 9A shows the reduced levels of Aβ1-42 monomer in the AD CSF samples. The differences were statistically significant to p≤0.002 as determined using a two-way t-test and Mann Whitney analysis of ranks, assuming the population was non-Gaussian. FIG. 9B shows the unchanged levels between the two groups of Aβ1-40 monomer.

FIG. 14B; antibody 19.3: FIG. 14C, ring). Immunocytochemical analysis was used to assess the deposition of new material (AD-DLs) (FIGS. 14B and 14C).

DETAILED DESCRIPTION OF THE INVENTION

Figure 1:
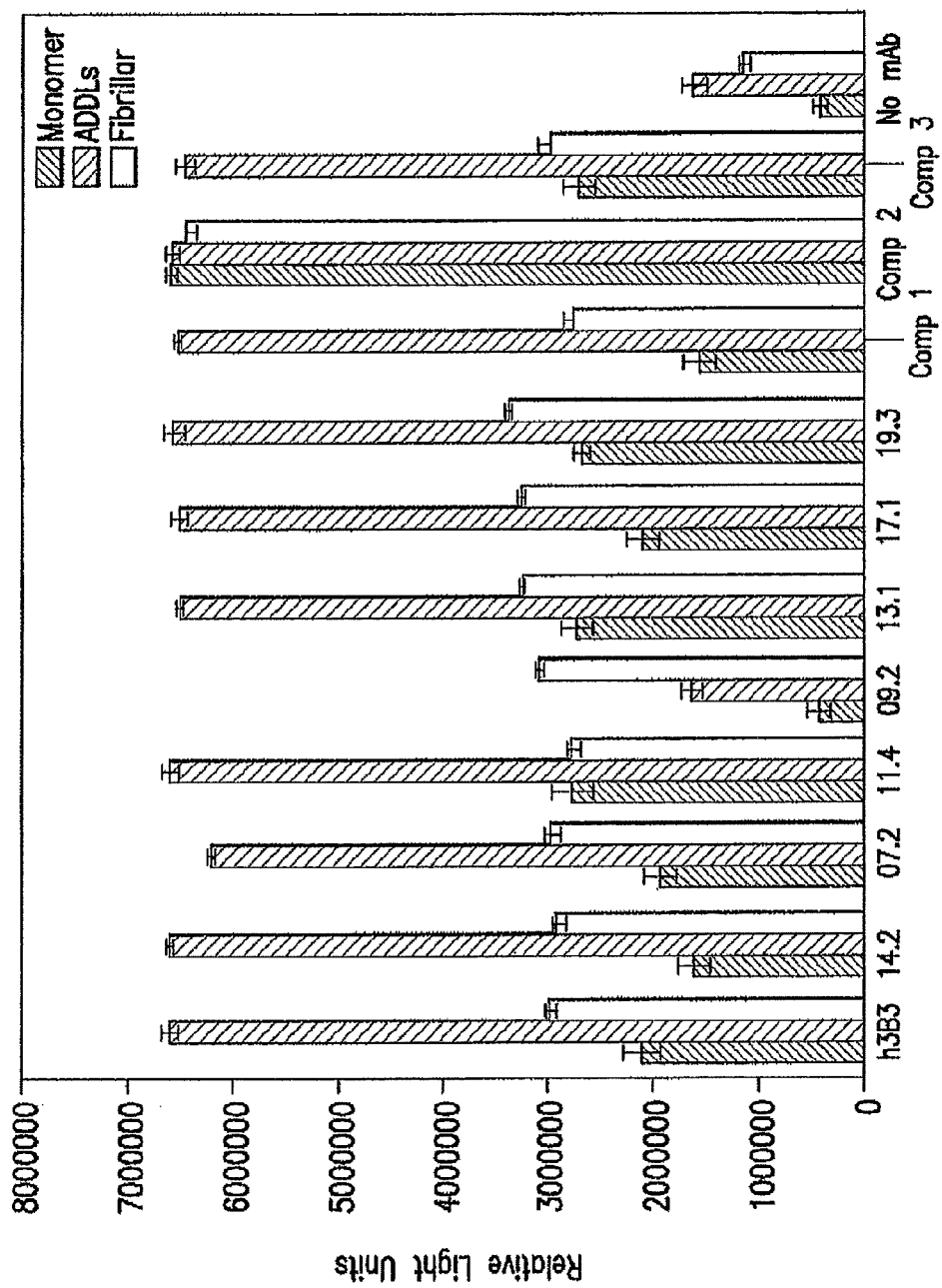
FIG. 1 is a graphic representation of the ELISA binding of a panel of humanized (h3B3) and affinity matured anti-ADDL (14.2, 7.2, 11.4, 9.2, 13.1, 17.1, and 19.3) antibodies and three comparator antibodies (Comp 1, 2, and 3) to monomer Aβ, ADDLs and fibrillar Aβ. The background of this assay was determined by removing the capture antibody from the ELISA (no mAb). Error bars represent standard error of the mean.

The present invention is directed to the treatment of a disease caused by, resulting from, or associated with the neurotoxic effects of soluble, oligomeric species of amyloid β1-42 (Aβ1-42) using an antibody that selectively and specifically binds soluble, oligomeric species of Aβ1-42 with high affinity in vivo and blocks binding of the same to neurons and amyloid plaques in vivo. The method of this invention can be used to provide acute behavioral benefits (e.g., within 1, 2 or 3 months of administration) and chronic disease modification. Moreover, in accordance with the method herein, the antibodies can be used as a stand-alone therapy, or can be used in combination with other Aβ- and/or Tau-directed therapies.

The antibodies of this invention have the added advantage of being capable of distinguishing between Alzheimer's disease (AD) and control human brain extracts, identifying endogenous oligomers in AD brain slices and on hippocampal cells, and neutralizing endogenous and synthetic ADDLs in solution. Antibodies of the invention specifically bind one or more multi-dimensional conformations of ADDLs, bind particular ADDLs derived from the oligomerization of Aβ1-42, while having significantly lower affinity or substantially no affinity for other Aβ species, including amyloid beta 1-42 monomer, amyloid beta 1-40 monomer, plaques and amyloid beta fibrils.

This invention is particularly directed to the use of antibodies 17.1, 14.2, 13.1, 19.3, 7.2, 9.2, 11.4, and derivatives thereof, that preferentially bind ADDLs and that have been characterized as to their specificity and selectivity for ADDLs. Importantly, the specificity and selectivity of the antibodies of this invention was not predictable from the linear epitope of Aβ to which they bound, nor was this activity predictable from their ability to detect ADDLs by western blot analysis, or from their ability to detect immuno-stained ADDLs bound to neurons. Moreover, the differential ability of the anti-ADDL antibodies of the invention to neutralize ADDLs and block binding to primary hippocampal neurons supports the belief that the antibodies of this invention act through binding to a more relevant, conformational epitope, which prevents soluble oligomeric species of Aβ1-42 from binding to neurons and amyloid plaques. One embodiment of the present invention, antibody 19.3, not only blocked the binding of ADDLs to primary neurons, but also abated ADDL-induced changes to hippocampal spine morphology, an indication that the impedance of ADDL-neural binding has significant physiological ramifications, for example, neuronal survival, neuronal connectivity and signal transduction. Antibody 19.3 also had an improved pharmacokinetic (PK) profile, as compared with a previously known anti-ADDL antibody, 3B3, when assessed in both in vitro and in vivo models. In addition, when administered to transgenic mice that over-express a human form of amyloid precursor protein (hAPP), antibody 19.3 was shown to penetrate the blood-brain-barrier, concentrate in the brain, and block incorporation of ADDLs into amyloid plaques. Since ADDLs are localized in the brain and act there to adversely affect neuronal function, one of skill in the art would appreciate and recognize that the penetration and concentration of antibody in the brain would be beneficial for immunotherapy. Taken together, these data demonstrate that selective anti-ADDL antibodies, such as antibody 19.3, can block the binding of ADDLs to hippocampal neurons, which are critically involved in learning and memory.

The method of treatment herein is based on a body of evidence that indicates that ADDLs, and not amyloid plaques per se, play a fundamental role in the cognitive decline associated with this disease (Walsh & Selkoe (2004) *Protein Pept. Lett.* 11:213-228). ADDLs are elevated in the AD brain and induce deficits in behavioral and electrophysiological endpoints when centrally administered to rodents (Walsh, et al. (2002) *Nature* 416:535-539; Cleary, et al. (2004) *Nat. Neurosci.* 8:79-84; Klyubin, et al. (2005) *Nat. Med.* 11:556-561; Balducci, et al. (2010) *Proc. Natl. Acad. Sci. USA* 107:2295-2300). Deficits in learning and memory have also been observed in a hAPP expressing mouse model, with the onset of impairment associated with elevated ADDL levels (Westerman, et al. (2002) *J. Neurosci.* 22:1858-1867; Ashe (2005) *Biochem. Soc. Trans.* 33:591-594; Lee, et al. (2005) *J. Biol. Chem.* 281:4292-4299; Lesne, et al. (2006) *Nature* 440:352-357). While the cellular and sub-cellular events that mediate these effects on cognition are not fully understood, it is clear that ADDLs bind to the synaptic terminals localized on the dendritic processes of hippocampal neurons (Lacore, et al. (2004) *J. Neurosci.* 24:10191-1022) and alter the morphology and number of dendritic spines (Lacor, et al. (2007) *J. Neurosci.* 27:796-807; Shankar, et al. (2007) *J. Neurosci.* 27:2866-2875; Shughrue, et al. (2010) *Neurobiol. Aging* 31:189-202). The finding that ADDLs bind to both GABAergic and glutamate neurons in the hippocampus (Shughrue, et al. (2010) supra), neurons critically involved in learning and memory, which results in the internalization of AMPA receptors (Zhao, et al. (2010) *J. Biol. Chem.* 285:7619-7632), further supports the indication that ADDLs directly or indirectly modulate these neurotransmitter systems (see, for example, Venkitaramani, et al. (2007) *J. Neurosci.* 27:11832-11837).

As described herein, a panel of anti-ADDL antibodies derived from anti-ADDL antibody, 3B3 (U.S. Pat. No. 7,780, 963 and U.S. Pat. No. 7,811,563), were assessed for their ability to block ADDL binding to primary hippocampal neurons. Selected monoclonal antibodies were then humanized and affinity matured for further characterization. Lead antibodies, selected for their ability to bind to ADDLs, were further assessed at a single concentration using a three-pronged ELISA to determine antibody binding to monomer Aβ, ADDLs, and fibrillar Aβ. As shown in FIG. 1, six of the seven affinity matured anti-ADDL antibodies, specifically antibodies 14.2, 7.2, 11.4, 13.1, 17.1, and 19.3 were ADDL preferring, when compared with monomer Aβ and fibrillar Aβ.

Figure 2:
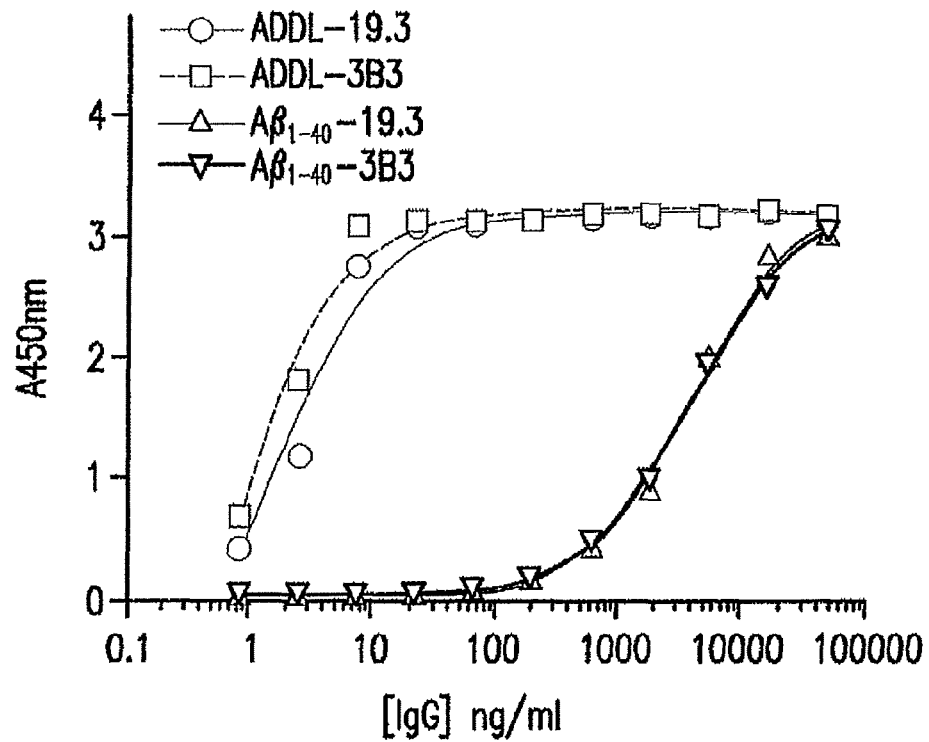
FIG. 2 is a graphic representation of the ELISA binding of anti-ADDL antibody 19.3 and antibody 3B3 to ADDLs or monomer Aβ (Aβ1-40) evaluated with an 11 point titration curve.
Figure 3:
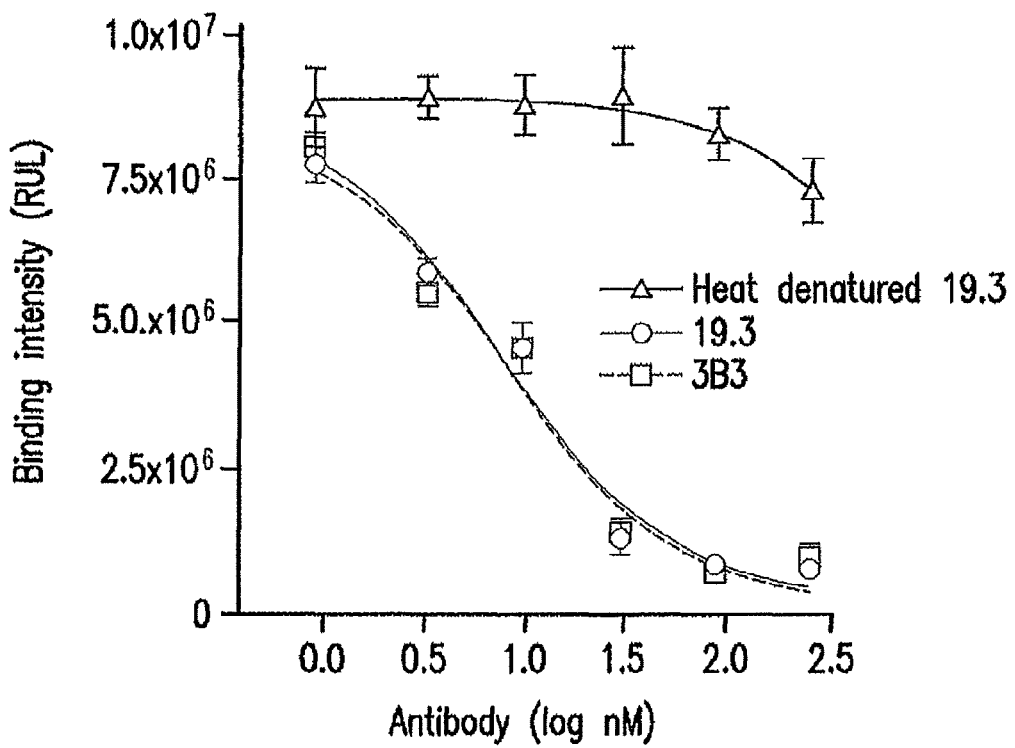
FIG. 3 is a graphic representation of the ability of anti-ADDL antibody 19.3 and 3B3 to block ADDL binding to primary hippocampal neuronal cells after pre-incubation with increasing concentration of the antibody. The ability of anti-ADDL antibody 19.3 to block ADDL binding to neurons was attenuated after heat denaturing of the antibody. Error bars represent standard error of the mean.

Subsequently, an eleven point titration curve and ELISA were used to ascertain the binding affinity of anti-ADDL antibodies to ADDLs and monomer Aβ (41-40) over a broad range of concentrations. As shown in FIG. 2, the anti-ADDL antibodies 3B3 and 19.3 were highly ADDL selective. In addition, antibodies were compared in a cell-based binding assay to determine the ability of antibodies to block ADDL binding to neurons. As shown in FIG. 3, ADDLs, pre-incubated with increasing concentrations of anti-ADDL antibodies 3B3 and 19.3, were added to primary hippocampal neurons, and a titration curve was used to show quantitatively the ability of the antibody to block ADDL binding to neurons. Taken together, these results show that anti-ADDL antibodies profoundly attenuate neuronal binding in a cell-based format.

Figure 4A:
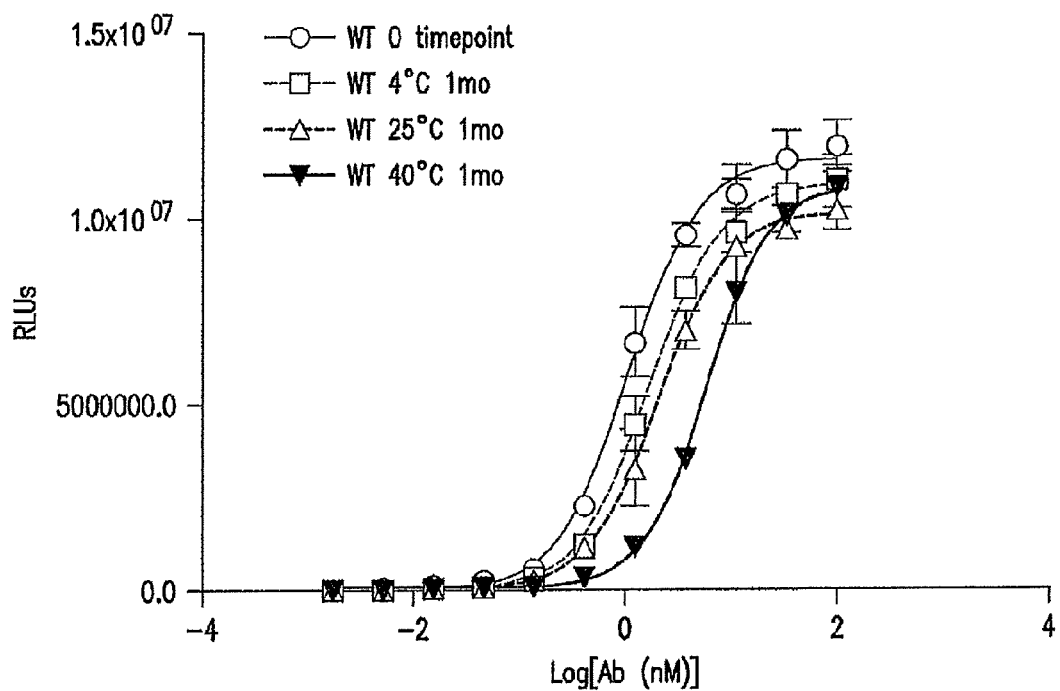
FIGS. 4A-4C are graphic representations of the ELISA binding to ADDLs of the anti-ADDL antibody 19.3 (designated as WT in FIG. 4A) and two 19.3-derived anti-ADDL antibodies (FIGS. 4B and 4C) after incubation up to one month at varying temperatures to evaluate antibody stability. The 19.3-derived anti-ADDL antibodies had a single amino-acid substitution of Asn33 within light chain CDR1 to either Ser33 (19.3S33) or Thr33 (19.3T33) (SEQ ID NOS: 42 and 43, respectively). Substitution of Asn33 with either S33 (FIG. 4B) or T33 (FIG. 4C) resulted in improved antibody stability, versus the parental 19.3 antibody.
Figure 4B:
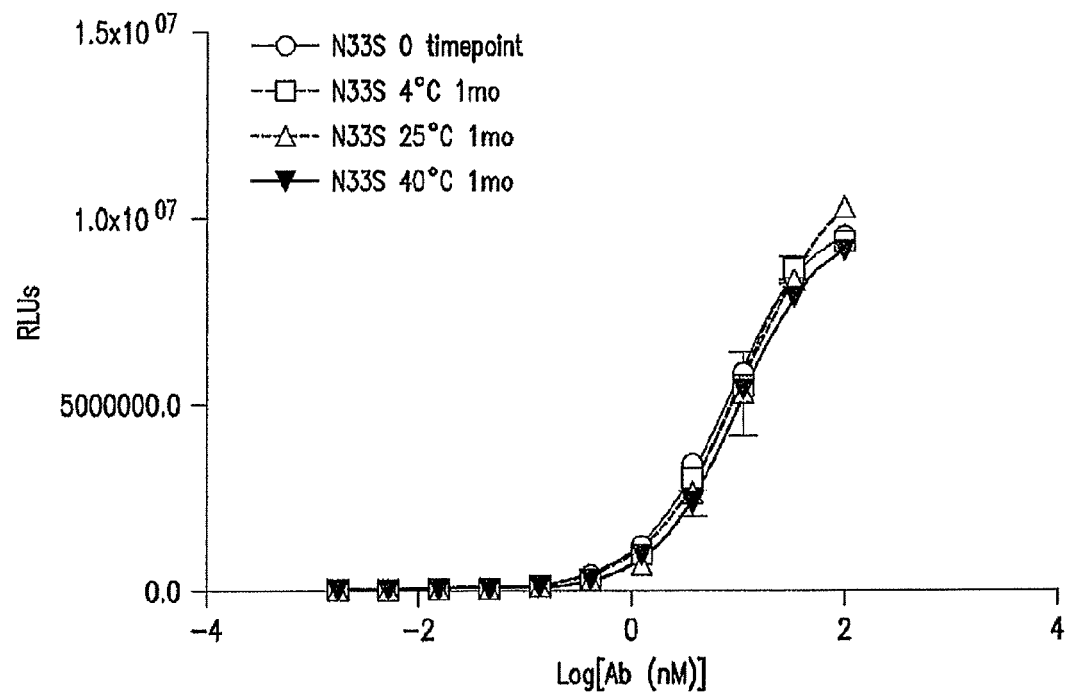
Figure 4C:
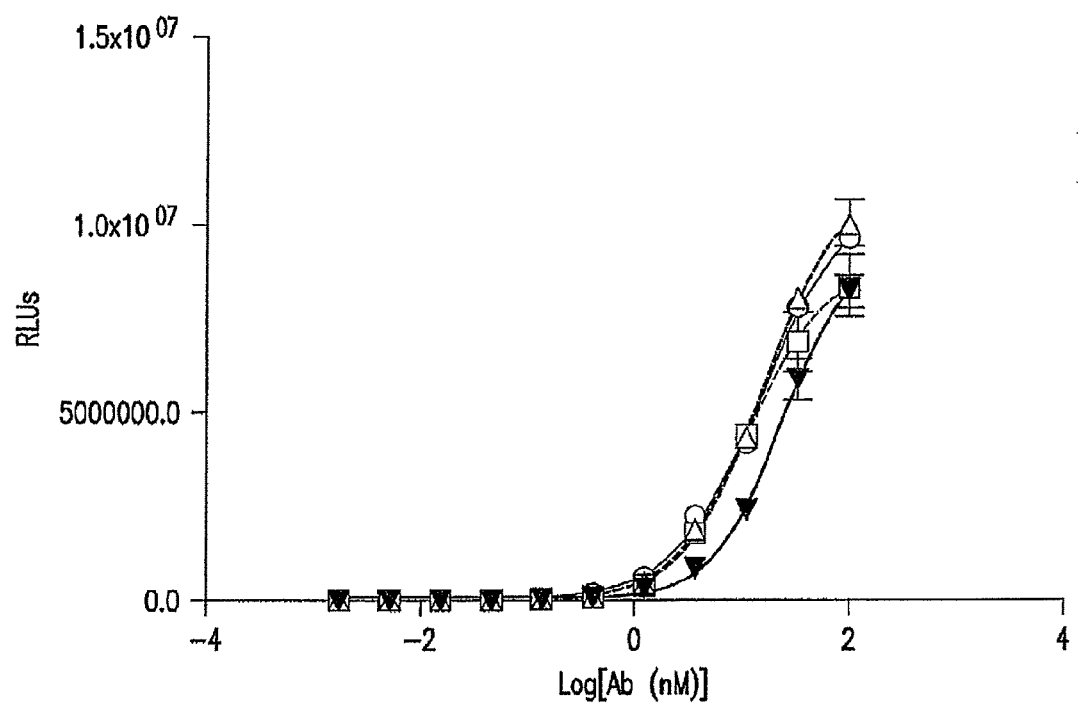

An assessment of the amino acid sequence was conducted to identify potential sites of deamidation. Asparagine and aspartic acid residues present in the CDRs of therapeutic antibodies can undergo deamidation and isoaspartate formation (Valsak & Ionescu (2008) *Curr. Pharm. Biotech.* 9:468-481; Aswad, et al. (2000) *J. Pharm. Biomed. Anal.* 21:1129-1136), the formation of which can alter the binding potency of an antibody and, in turn, reduce antibody effectiveness for use as a therapeutic. Thus, those of skill in the art would recognize and appreciate that the presence of an asparagine or an aspartic acid within the CDRs for the 19.3 antibody would not be desirable. Accordingly, the asparagine residue at position 33 of the light chain CDR1 was altered to optimize the stability of the anti-ADDL antibody 19.3. Derivatives of the 19.3 antibody were produced with the substitution of serine (SEQ ID NO:42), threonine (SEQ ID NO:43), or glutamic acid (SEQ ID NO:45) for the asparagine at position in CDR1. The substitution of aspartic acid (SEQ ID NO:46) for the asparagine as position 33 was also generated as a control. These changes remove the possibility of deamidation of asparagine at position 33 in CDR1. The 19.3 derivatives were generated and characterized as described in the Examples. As shown in FIGS. 4B and 4C, respectively, two representative derivatives, 19.3S33 (SEQ ID NO:42) and 19.3T33 (SEQ ID NO:43), had enhanced binding stability following a one-month incubation at varying temperatures. Other amino acid substitutions in the light chain CDR1 for the asparagine at positions 33 and 35 (SEQ ID NOs:47-50) and in the light chain CDR2 for the asparagine at position 58 position (SEQ ID NOs:52-55) are listed in Tables 7 and 8, respectively, for further evaluation.

Figure 5:
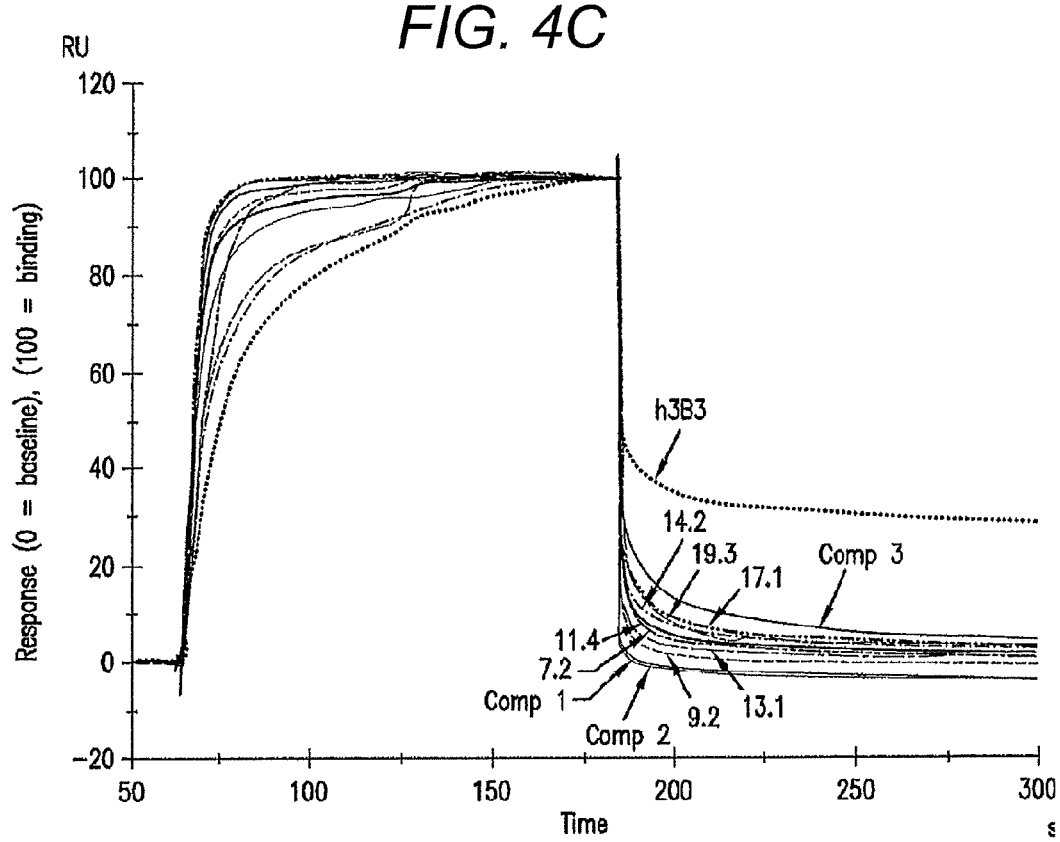
FIG. 5 is a graphic representation of the binding and dissociation of anti-ADDL antibodies to immobilized human FcRn when assessed with BIACORE™ (GE Healthcare, Piscataway, N.J.). The adjusted sensorgram shows initial binding at pH 6.0 and then the dissociation of antibodies at pH 7.3 from 180 seconds. A report point (Stability) was inserted at 5 seconds after the end of pH 6.0 binding and the "% bound" was calculated as $RU_{stability}/RU_{Binding}$ (%).
Figure 10:
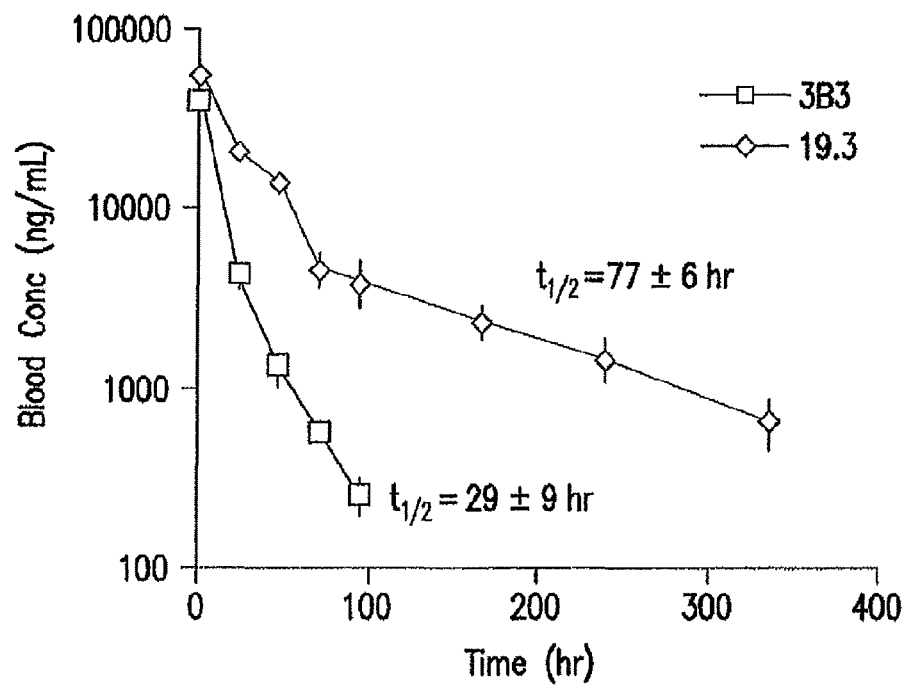
FIG. 10 is a graphical representation of the pharmacokinetic (PK) profile of anti-ADDL antibodies 19.3 and 3B3 evaluated in heterozygous 276 human FcRn mice (Jackson Laboratory (Bar Harbor, Me.) following a single 10 mg/kg intravenous (IV) administration. The concentration of antibody was measured at various time intervals to determine the half-life ($t_{1/2}$) of free antibody (19.3: 77±6 hours; 3B3: 29±9 hours).

To determine the pharmacokinetics of the affinity matured anti-ADDL antibodies of this invention, a series of in vitro and in vivo studies were conducted. The binding of antibodies to the FcRn receptor at pH 6.0 has been shown to be predictive of antibody half-life in humans (Zalevsky, et al. (2010) *Nat. Biotech.* 28(2):157-159) and at pH 7.3 (U.S. 61/307,182) The binding and dissociation of the anti-ADDL antibodies of the invention to immobilized human FcRn was assessed via label-free interaction analysis, such as that offered by BIA-CORE™ Life Sciences, BIACORE™ T-100 (GE Healthcare, Piscataway, N.J.). An adjusted sensorgram is used to show the initial binding at pH 6.0 and then the dissociation of antibodies at pH 7.3 from 180 seconds. A report point (Stability) was inserted at 5 seconds after the end of pH 6.0 binding and the "% bound" was calculated as $RU_{stability}/RU_{Binding}$ (%). As shown in FIG. 5, the off-rate for humanized 3B3 was markedly slower than the seven anti-ADDL antibodies of this invention, which included antibody 19.3, and three comparator antibodies. In that a slow off-rate is thought to be an indicator of poor in vivo PK, an additional in vivo study was conducted in transgenic FcRn mice (heterozygous 276 human FcRn mice, Jackson Laboratories, Bar Harbor, Me.). When the transgenic FcRn mice were given 10 mg/kg intravenously (IV) of either anti-ADDL antibody 3B3 or 19.3, a significant difference in pharmacokinetics was determined. As shown in FIG. 10, the half-life ($t_{1/2}$) of anti-ADDL antibody 3B3 was relatively short (29±9 hours), which was consistent with the prediction from the in vitro BIACORE™ data, while the half-life for anti-ADDL antibody 19.3 was significantly longer (77±6 hours). Given its more desirable PK, 19.3 is of use as a therapeutic due to its bioavailability.

Figure 12:
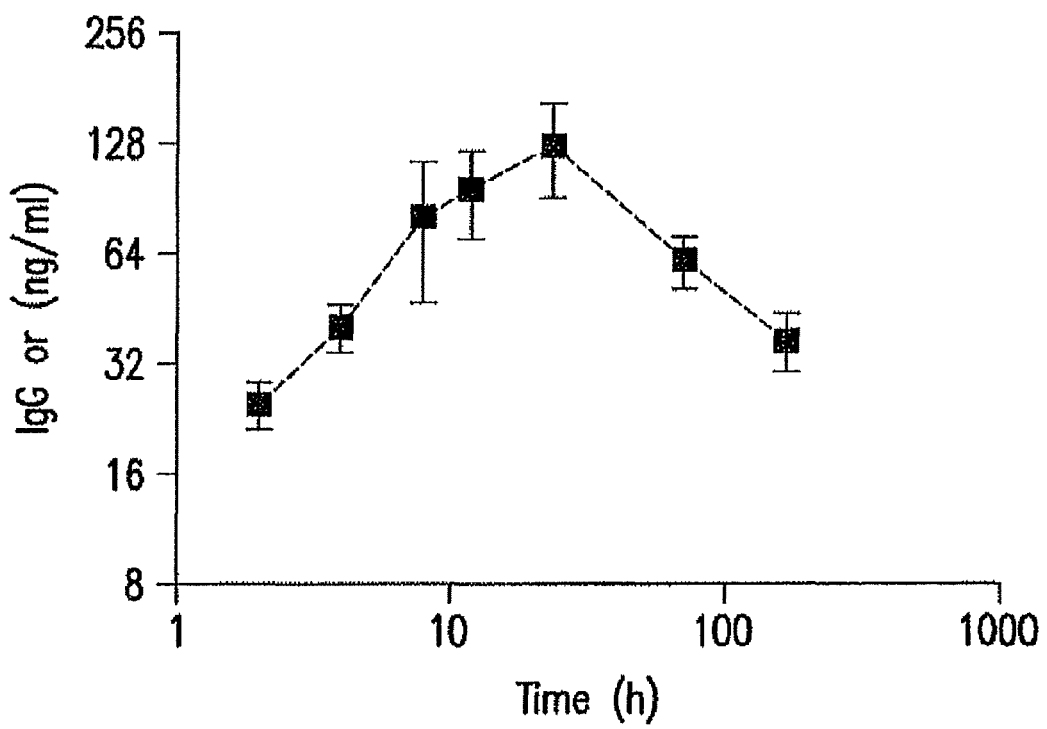
FIG. 12 is a graphical representation of the PK of anti-ADDL antibody 19.3 assessed in primate (three male rhesus monkeys) cerebrospinal fluid (CSF) using a cisterna magna ported rhesus model following administration of a bolus IV dose of 5 mg/kg. At about 48 hours post-dose, the anti-ADDL antibody 19.3 was present in the CSF at 0.1% of the concentration in serum.

To confirm the predicted half-life of anti-ADDL antibody 19.3 in primates, a primate pharmacokinetics study was conducted for the antibody in a cohort of cisterna magna ported rhesus monkeys. The animals were dosed with a single intravenous (IV) bolus or subcutaneous (SC) injection of anti-ADDL antibody 19.3 (5 mg/kg) and blood samples collected after antibody administration. Concurrently, CSF samples were collected from the cisterna magna port at timed intervals and the concentration of anti-ADDL antibody 19.3 in serum and CSF was determined with an anti-human IgG ELISA assay. When the animals were administered anti-ADDL antibody 19.3 by a single IV bolus injection a $t_{1/2}$ of 254±28 hours was observed (FIG. 11), while a $t_{1/2}$ of 204±49 hours was observed for the subcutaneous administration. In addition, it was found that anti-ADDL antibody 19.3 was able to cross into the primate CSF, where it increased in concentration during the first hours and peaked at about 0.1% of the antibody dosed (FIG. 12).

Figure 13B:
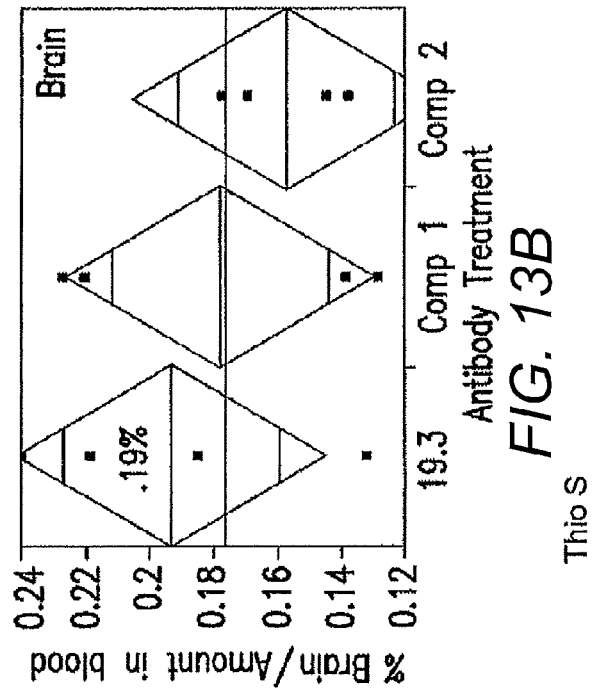
FIGS. 13A-13D are representations of the ability of anti-ADDL antibody 19.3, versus two comparator antibodies (Comp 1 and Comp2), to cross the blood-brain-barrier in a transgenic mouse model that over-expresses human amyloid precursor protein (hAPP). Mice were injected intravenously (IV) with $^{125}$I-labeled anti-ADDL antibody 19.3, or a comparator antibody, and the blood, CSF and brain samples were collected two hours post-dose. Upon assessment of the radioactivity distribution, 0.02% of anti-ADDL antibody 19.3 was present in the CSF (FIG. 13A), while 0.19% was seen in the brain (FIG. 13B). Similar levels were seen with the two comparator antibodies. Immunocytochemical analysis demonstrated that anti-ADDL antibody 19.3 is moving from plasma to the brain and is concentrated after dosing (FIG. 13C, arrows), and that some anti-ADDL antibody 19.3 is associated near the periphery of plaques (FIG. 13D). This shows that anti-ADDL antibody 19.3 is able to penetrate into the brain and bind ADDLs.
Figure 13A:
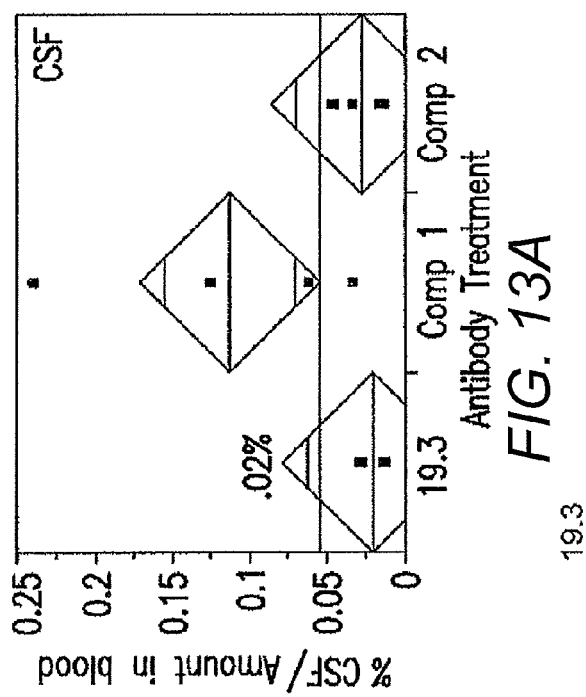
Figure 13D:
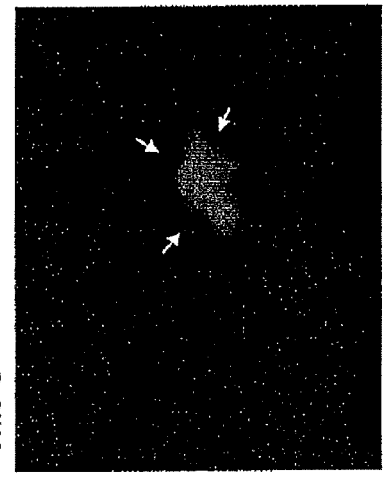
Figure 15:
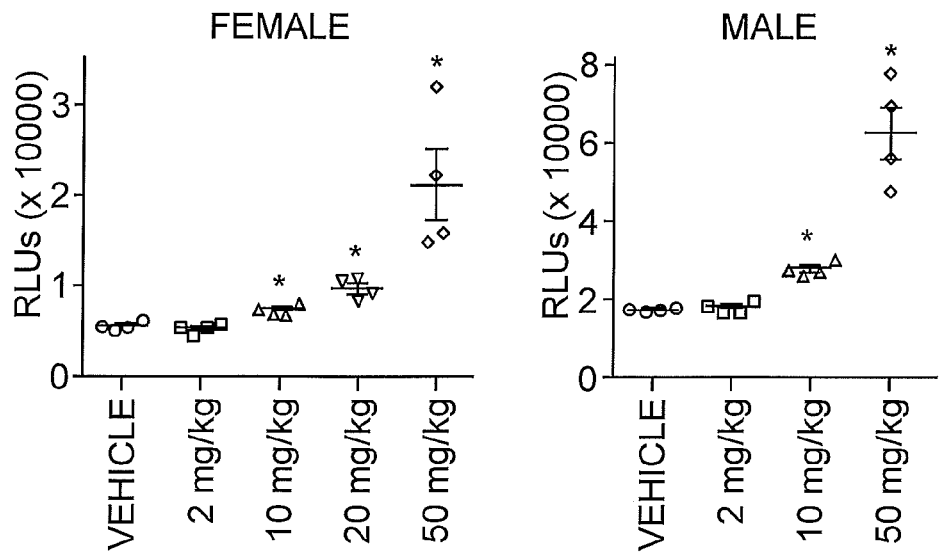
FIG. 15 shows blood-brain-barrier penetration and target engagement of antibody 19.3 in the brain. Levels of antibody 19.3:ADDL complexes in the brain of female (left panel) and male (right panel) Tg2576 mice 24 hours following IV injection of antibody 19.3 were determined. The asterisks indicate a statistically significant difference from vehicle control levels. (RLU, relative light units).

To ascertain the amount of Aβ oligomeric species present in the brain of AD patients, Aβ oligomeric species were determined in AD brain as compared to age-matched (FIG. 8A) and young (FIG. 8B) controls. The absolute levels of Aβ oligomers observed were ~2 pg/mL in AD and 0.2 pg/mL in control CSF samples. To compare the levels of Aβ oligomeric species to the amount of antibody that crosses the blood-brain barrier, anti-ADDL antibody 19.3 and two comparator antibodies (Comp 1 and Comp 2) were $^{125}$I-labeled and administered to aged (twelve-month old) mice that over-express hAPP, a rodent model for AD. Two hours after IV dosing, about 0.02% of antibody 19.3 was seen in the CSF (FIG. 13A), while about 0.19% of antibody 19.3 was seen in the brain (FIG. 13B). Similar levels were seen for the two comparator antibodies (FIGS. 13A and 13B). When immunocytochemical analysis was carried out on brain sections of the dosed mice and the localization of anti-ADDL antibody 19.3 was determined (arrow in FIG. 13C), a concentration of the antibody associated with the deposition of Aβ into plaques was observed (FIG. 13D). Recently, it was shown that exogenous ADDLs were deposited into plaques when administered to mice that overexpress hAPP (Gaspar, et al. (2010) *Exp. Neurol.* 223:394-400). Thus, the findings herein confirmed that the localized anti-ADDL antibody 19.3 bound to circulating ADDLs that became associated with plaques. Overall, this analysis demonstrated that the anti-ADDL antibody 19.3 penetrated into the CSF and brain at a level sufficient to bind the soluble oligomeric species of Aβ present in the brain. Moreover, the animal model studies indicated that the minimal efficacious dose to significantly elevate antibody 19.3:ADDL complexes in the brain was 10 mg/kg (FIG. 15).

Figure 14A:
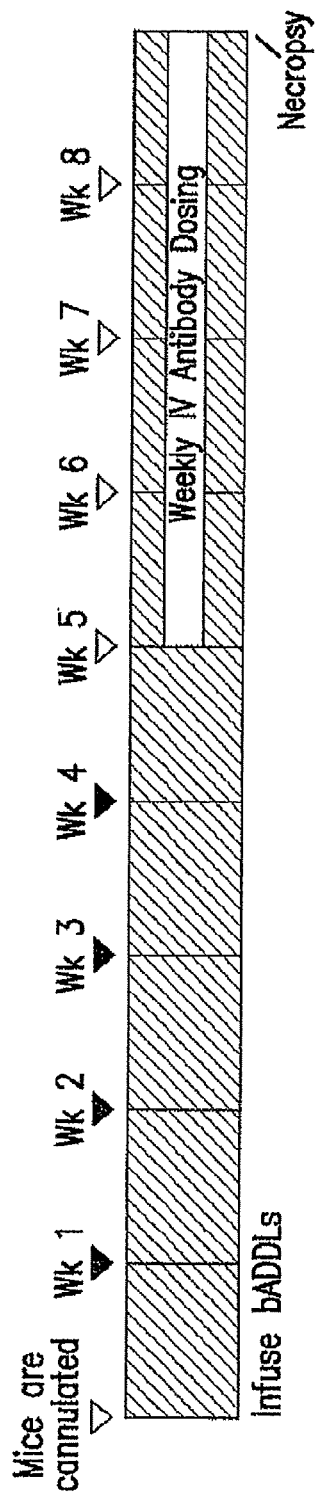
FIGS. 14A-14C show that anti-ADDL antibody 19.3 blocks the deposition of ADDLs into growing plaques in a transgenic mouse model that over-expresses hAPP. Biotinylated ADDLs (bADDLs) infused into the hippocampus of 12-month-old mice for four weeks (one injection per week) (FIG. 14A) labeled existing plaques (vehicle alone.
Figure 14C:
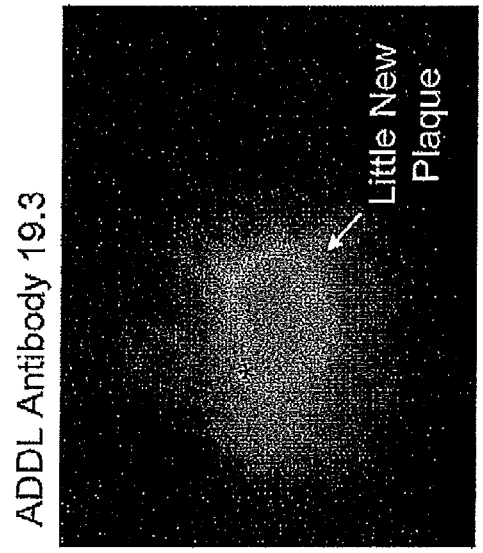
Figure 14B:
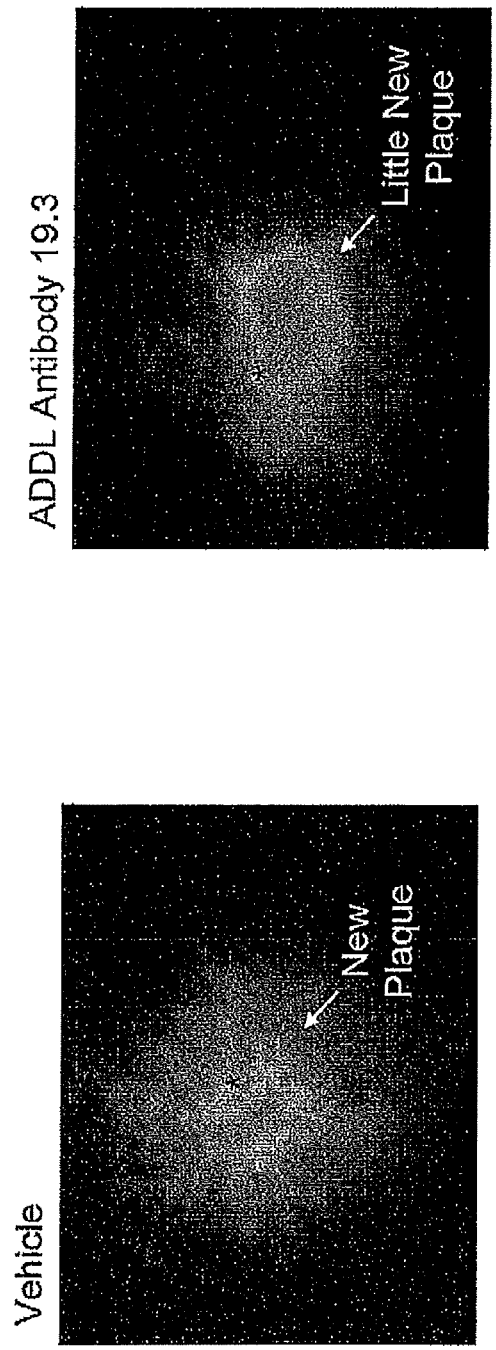

To further evaluate the in vivo efficacy of the antibodies of this invention, the ability of antibody 19.3 to block the deposition of ADDLs into growing plaques was assessed in hAPP transgenic mice following four weekly infusions of biotinylated ADDLs (bADDLs) into the hippocampus of 12-month old mice to label existing plaques (FIG. 14A). The animals then received four weekly intravenous infusions of antibody 19.3 (FIG. 14A). The deposition of new material (ADDLs) into growing plaques was assessed by immunocytochemical analysis. As seen in FIGS. 14B and 14C, anti-ADDL antibody 19.3 significantly reduced the deposition of ADDLs into the periphery of existing plaques (FIG. 14C) as compared to mice treated with vehicle alone (FIG. 14B), but did bind vascular plaques. Taken together, these results demonstrated that an anti-ADDL antibody, specifically the 19.3 antibody, was able to cross the blood-brain-barrier, bind ADDLs, and block the deposition of new material into growing plaques.

Figure 16:
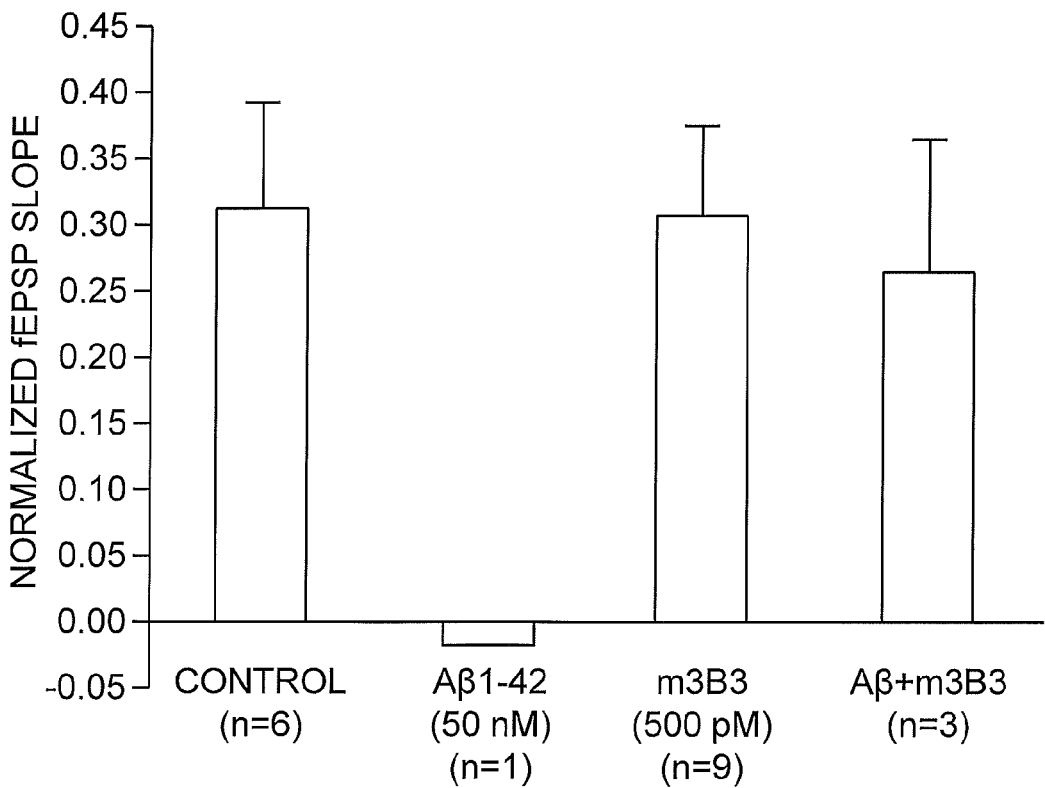
FIG. 16 shows that parental anti-ADDL antibody 3B3 reverses acute Aβ impairment of long term potentiation (LTP) in murine hippocampal slices. The magnitude of LTP is shown as a normalized potentiation of the fEPSP (field excitatory postsynaptic potential) slope values averaged from the last 10 minutes of recordings.
Figure 17:
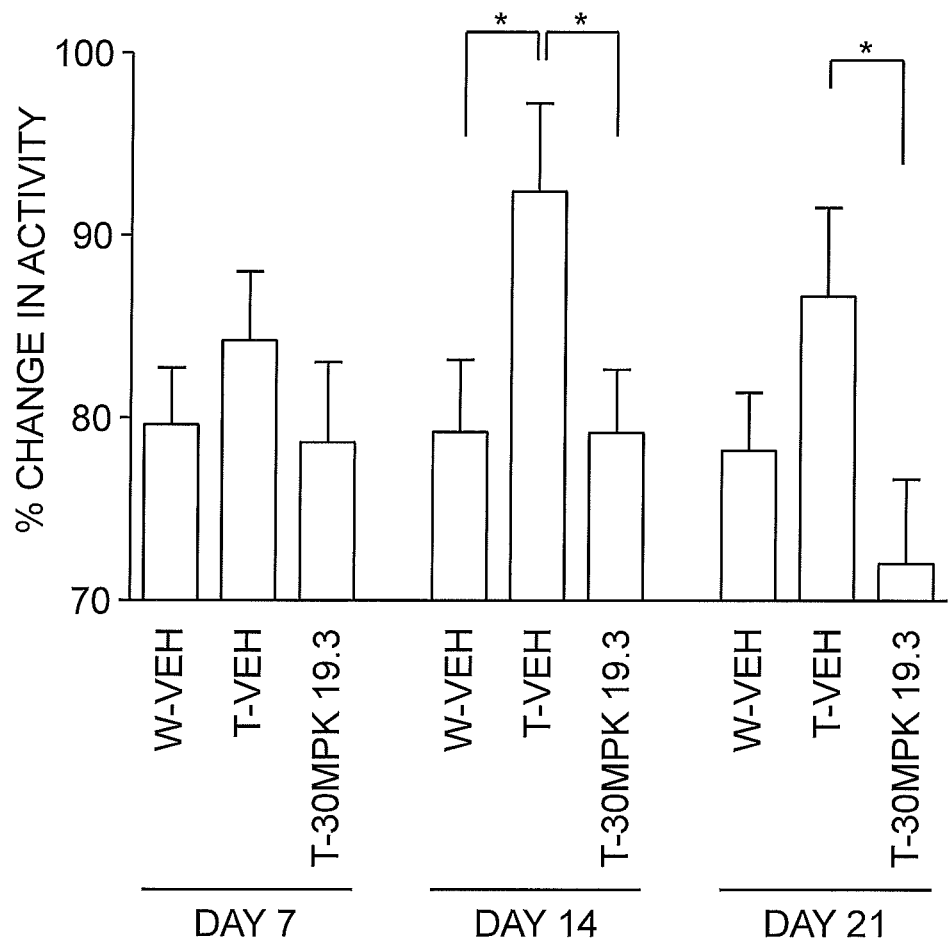
FIG. 17 shows the behavioral effects of antibody 19.3. Shown is a comparison of locomotor activity in Tg2576 and non-transgenic control mice at Days 7, 14, and 21 expressed as percent change relative to baseline activity prior to treatment with antibody 19.3 (30 mg/kg) and vehicle, respectively. A significant decrease in locomotor activity was observed 14 and 21 days post-treatment with antibody 19.3. W-Veh=non-transgenic mice; T-Veh: Tg2576 mice treated with control IgG; T-30 mpk 19.3=Tg2576 mice treated with antibody 19.3 at 30 mg/kg.

ADDL binding may also have long-term effects on neurons. Recent studies have shown that ADDL binding to hippocampal neurons can initiate a signaling cascade that results in the phosphorylation of tau (De Felice, et al. (2006) *Neurobiol. Aging* 29:394-400). One component of this signaling cascade, GSK-3β, has also been shown to be modulated by ADDL binding in vivo and in vitro (Ma, et al. (2006) *J. Neurosci. Res.* 83:374-384). In this study, it was observed that passive immunization of hAPP mice with an antibody that reduced ADDLs also reduced GSK-3β levels and phosphorylation of tau in the cortex. This finding supports a link between Aβ and phosphorylated tau and suggests that ADDL binding may trigger events that lead to the intracellular aggregation of tau. Further, the data indicates that antibodies that prevent the binding of ADDLs to neurons and the associated loss of synaptic spines, such as the antibodies of this invention, would ameliorate the cognitive and/or pathological outcomes associated with Alzheimer's disease and related diseases. In this respect, it was demonstrated that an anti-ADDL antibody can reverse acute ADDL impairment of LTP in murine hippocampal slices (FIG. 16) and alter behavioral activity by reverting increases in locomotor activity in the Tg2576 mouse model of AD (FIG. 17).

Accordingly, this invention includes the use of an anti-ADDL antibody or antibody fragment to prevent or treat a disease associated with, caused by, or resulting from the accumulation of ADDLs (for example, Alzheimer's disease or similar memory-related disorders). Evidence in the art indicates that elevated levels of Aβ, but not necessarily aggregated plaque, cause Alzheimer's disease-associated dementia and subsequent tau abnormalities. Aβ-derived diffusible ligands are directly implicated in neurotoxicity associated with Alzheimer's disease. The art indicates that ADDLs are elevated in transgenic mice and Alzheimer's disease patients and modulate functional activity associated with mnemonic processes in animal models. Thus, removing this form of Aβ would provide relief from the neurotoxicity associated with Alzheimer's disease. As such, treatment with an antibody of the present invention that reduces central nervous system ADDL load could prove efficacious for the treatment of Alzheimer's disease.

Patients amenable to treatment include individuals at risk of disease but not exhibiting symptoms, as well as patients presently exhibiting symptoms. In the case of Alzheimer's disease, virtually anyone is at risk of suffering from Alzheimer's disease if he or she lives long enough. Therefore, the antibody or antibody fragments of the present invention can be administered prophylactically to the general population without the need for any assessment of the risk of the subject patient. The present methods are especially useful for individuals who have a known genetic risk of Alzheimer's disease. Such individuals include those having relatives who have been diagnosed with the disease, and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively. Other markers of risk are mutations in the presenilin genes, PS1 and PS2, and ApoE4, family history of Alzheimer's disease, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have Alzheimer's disease. These include measurement of CSF tau and Aβ1-42 levels. Individuals suffering from Alzheimer's disease can also be diagnosed by ADRDA criteria or the method disclosed herein.

In asymptomatic patients, treatment can begin at any age (for example, 10, 20, 30 years of age). Usually, however, it is not necessary to begin treatment until a patient reaches 40, 50, 60 or 70 years of age. Treatment typically entails multiple dosages over a period of time. Treatment can be monitored by assaying for the presence of ADDLs over time.

In therapeutic applications, a pharmaceutical composition or medicament containing an antibody or antibody fragment of the invention is administered to a patient suspected of, or already suffering from such a disease associated with the accumulation of ADDLs in an amount sufficient to cure, or at least partially arrest, the symptoms of the disease (biochemical, histologic and/or behavioral), including its complications and intermediate pathological phenotypes in development of the disease. In prophylactic applications, a pharmaceutical composition or medicament containing an antibody or antibody fragment of the invention is administered to a patient susceptible to, or otherwise at risk of, a disease associated with the accumulation of ADDLs in an amount sufficient to achieve passive immunity in the patient thereby eliminating or reducing the risk, lessening the severity, or delaying the onset of the disease, including biochemical, histologic and/or behavioral symptoms of the disease, its complications and intermediate pathological phenotypes present during development of the disease. In some methods, administration of agent reduces or eliminates myocognitive impairment in patients that have not yet developed characteristic Alzheimer's pathology. In particular embodiments, an effective amount of an antibody or antibody fragment of the invention is an amount which achieves at least a 15%, 20%, 30%, 40%, 50%, 60%, 70%, 80%, 90%, 95%, or 97% decrease in the binding of ADDLs to neurons in the patient as compared to binding of ADDLs in the absence of treatment so that impairment of long-term potentiation/memory formation is decreased.

Effective doses of the compositions of the present invention, for the treatment of the above described conditions vary depending, upon many different factors, including means of administration, physiological state of the patient, whether the patient is human or an animal, other medications administered, and whether treatment is prophylactic or therapeutic. Usually, the patient is a human but nonhuman mammals such as dogs or transgenic mammals can also be treated.

Treatment dosages are generally titrated to optimize safety and efficacy. For passive immunization with an antibody or antibody fragment, dosage ranges from about 0.0001 to 100 mg/kg, and more usually 0.01 to 20 mg/kg, of the host body weight are suitable. For example, dosages can be 0.5 mg/kg body weight or 10 mg/kg body weight or within the range of 0.5-10 mg/kg are particularly contemplated. In one embodiment, the dose is at or about 10 mg/kg (i.e., ±5 mg/kg). In another embodiment, the dose is at or about 1 mg/kg (i.e., ±0.5 mg/kg). In some methods, two or more antibodies of the invention with different binding specificities are administered simultaneously, in which case the dosage of each antibody administered falls within the ranges indicated. Antibodies are usually administered on multiple occasions, wherein intervals between single dosages can be weekly, monthly or yearly. An exemplary treatment regime entails subcutaneous dosing, once biweekly or monthly. Intervals can also be irregular as indicated by measuring blood levels of antibody to ADDLs in the patient. In some methods, dosage is adjusted to achieve a plasma antibody concentration of 1-1000 μg/mL and in some methods 25-300 μg/mL. Alternatively, the antibody or antibody fragment can be administered as a sustained-release formulation, in which case less frequent administration is required.

Dosage and frequency vary depending on the half-life of the antibody in the patient. In general, human and humanized antibodies have longer half-lives than chimeric antibodies and nonhuman antibodies. As indicated above, dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Antibody and antibody fragments of the present invention can be administered as a component of a pharmaceutical composition or medicament. Pharmaceutical compositions or medicaments generally contain the active therapeutic agent and a variety of other pharmaceutically acceptable components. See, Remington: The Science and Practice of Pharmacy, Alfonso R. Gennaro, editor, 20th ed. Lippincott Williams & Wilkins: Philadelphia, Pa., 2000. The preferred form depends on the intended mode of administration and therapeutic application. Pharmaceutical compositions can contain, depending on the formulation desired, pharmaceutically-acceptable, non-toxic carriers or diluents, which are defined as vehicles commonly used to formulate pharmaceutical compositions for animal or human administration. Diluents are selected so as not to affect the biological activity of the combination. Examples of such diluents are distilled water, physiological phosphate-buffered saline, Ringer's solutions, dextrose solution, and Hank's solution.

Pharmaceutical compositions can also contain large, slowly metabolized macromolecules such as proteins, polysaccharides such as chitosan, polylactic acids, polyglycolic acids and copolymers (such as latex-functionalized SEPHAROSE™, agarose, cellulose, and the like), polymeric amino acids, amino acid copolymers, and lipid aggregates (such as oil droplets or liposomes).

Administration of a pharmaceutical composition or medicament of the invention can be carried out in a variety of routes including, but not limited to, oral, topical, pulmonary, rectal, subcutaneous, intradermal, intranasal, intracranial, intramuscular, intraocular, or intrathecal or intra-articular injection, and the like. The most typical route of administration is intravenous followed by subcutaneous, although other routes can be equally effective.

Intramuscular injection can also be performed in the arm or leg muscles. In some methods, agents are injected directly into a particular tissue where deposits have accumulated, for example, intracranial or intrathecal injection. In some embodiments, an antibody or antibody fragment is injected directly into the cranium or CSF. In other embodiments, antibody or antibody fragment is administered as a sustained-release composition or device, such as a MEDIPAD™ device.

For parenteral administration, antibody or antibody fragments of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions. Antibodies can be administered in the form of a depot injection or implant preparation which can be formulated in such a manner as to permit a sustained-release of the active ingredient.

An exemplary, composition contains an isolated antibody, or antibody fragment thereof, of the present invention formulated as a sterile, clear liquid at a concentration of at least 10 mg/ml in isotonic buffered saline (10 mM histidine, 150 mM sodium chloride, 0.01% (w/v) POLYSORBATE 80, pH 6.0). An exemplary antibody formulation is filled as a single dose, 0.6 ml glass vials filled with 0.3 ml of solution per vial. Each vial is stopped with a TEFLON-coated stopper and sealed with an aluminum cap.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced delivery.

For suppositories, binders and carriers include, for example, polyalkylene glycols or triglycerides; such suppositories can be formed from mixtures containing the active ingredient in the range of 0.5% to 10%, or more desirably 1%-2%.

Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained-release formulations or powders and contain 10%-95% of active ingredient, or more suitably 25%-70%.

Topical application can result in transdermal or intradermal delivery. Topical administration can be facilitated by co-administration of the agent with cholera toxin or detoxified derivatives or subunits thereof or other similar bacterial toxins (see Glenn, et al. (1998) *Nature* 391:851). Co-administration can be achieved by using the components as a mixture or as linked molecules obtained by chemical crosslinking or expression as a fusion protein.

Alternatively, transdermal delivery can be achieved using a skin path or using transferosomes (Paul, et al. (1995) *Eur. J. Immunol.* 25:3521-3524; Cevc, et al. (1998) *Biochem. Biophys. Acta* 1368:201-215).

To provide prophylactic or therapeutic treatment of diseases such as AD, monoclonal antibodies that differentially recognize multi-dimensional conformations of Aβ-derived diffusible ligands, i.e., ADDLs, were generated. These antibodies were humanized and, in some embodiments, affinity-matured. The antibodies advantageously distinguish between Alzheimer's disease and control human brain extracts, and identify endogenous Aβ1-42 oligomers in Alzheimer's disease brain slices and in cultured hippocampal cells. Further, the antibodies of the present invention neutralize endogenous and synthetic ADDLs in solution. So-called "synthetic" ADDLs are produced in vitro by mixing purified Aβ1-42 under conditions that generate ADDLs. See, U.S. Pat. No. 6,218,506. The antibodies disclosed herein exhibit a high degree of selectivity for ADDLs, with minimal detection of monomer Aβ species. Moreover, these antibodies differentially block the ability of ADDL-containing preparations to bind primary cultures of rat hippocampal neurons and immortalized neuroblastoma cell lines, and also block ADDL incorporation into amyloid plaques. These findings demonstrate that these antibodies possess a differential ability to recognize a multi-dimensional conformation of ADDLs despite similar linear sequence recognition and affinities. Since ADDLs are known to associate with a subset of neurons and disrupt normal neuronal function, the antibodies of this invention find use in the prevention of ADDL binding to neurons and the assembly of ADDLs into plaques and, in turn, can be used for the treatment of ADDL-related diseases including Alzheimer's disease.

Accordingly, one embodiment of the present invention is an isolated antibody that differentially recognizes one or more multi-dimensional conformations of ADDLs. An "isolated" antibody of the present invention refers to an antibody which is substantially free of other antibodies. However, the molecule may include some additional agents or moieties which do not deleteriously affect the basic characteristics of the antibody (for example, binding specificity, neutralizing activity, etc.).

An antibody which is capable of specifically and selectively binding one or more multidimensional conformations of ADDLs, binds particular ADDLs derived from the oligomerization of Aβ1-42, but does not cross-react with other Aβ peptides, namely monomeric Aβ1-12, Aβ1-28, Aβ1-40, and Aβ12-28 as determined by western blot analyses as disclosed herein, and preferentially binds ADDLs in solution. Specific binding between two entities generally refers to an affinity of at least $10^6$, $10^7$, $10^8$, $10^9$, or $10^{10}$ $M^{-1}$. Affinities greater than $10^8$ $M^{-1}$ are desired to achieve specific binding.

In particular embodiments, an antibody that is capable of specifically binding a multi-dimensional conformation of one or more ADDLs is also raised against, i.e., an animal is immunized with, multi-dimensional conformations of ADDLs. In other embodiments, an antibody that is capable of specifically binding a multi-dimensional conformation of one or more ADDLs is raised against a low n-mer-forming peptide such as Aβ1-42[Nle35-Dpro37].

The term "epitope" refers to a site on an antigen to which B and/or T cells respond or a site on a molecule against which an antibody will be produced and/or to which an antibody will bind. For example, an epitope can be recognized by an antibody defining the epitope.

A linear epitope is an epitope wherein an amino acid primary sequence comprises the epitope recognized. A linear epitope typically includes at least 3, and more usually, at least 5, for example, about 6 to about 10 amino acids in a unique sequence.

A conformational epitope, in contrast to a linear epitope, is an epitope wherein the primary sequence of the amino acids comprising the epitope is not the sole defining component of the epitope recognized (for example, an epitope wherein the primary sequence of amino acids is not necessarily recognized by the antibody defining the epitope). Typically a conformational epitope encompasses an increased number of amino acids relative to a linear epitope. With regard to recognition of conformational epitopes, the antibody recognizes a three-dimensional structure of the peptide or protein. For example, when a protein molecule folds to form a three-dimensional structure, certain amino acids and/or the polypeptide backbone forming the conformational epitope become juxtaposed enabling the antibody to recognize the epitope.

Methods of determining conformation of epitopes include, but are not limited to, for example, x-ray crystallography, two-dimensional nuclear magnetic resonance spectroscopy and site-directed spin labeling and electron paramagnetic resonance spectroscopy. See, for example, Epitope Mapping Protocols in *Methods in Molecular Biology* (1996) Vol. 66, Morris (Ed.).

The term "Aβ1-40 monomer" or "Aβ1-42 monomer" as used herein refers to the direct product of the enzymatic cleavage, i.e., aspartic protease activity, by β-secretase and γ-secretase on the amyloid protein precursor (APP) in a cell-free or cellular environment. Cleavage of APP by β-secretase generates the Aβ species beginning at Asp 1 (numbering as to Aβ peptide sequence after cleavage), while γ-secretase liberate the C-terminus of Aβ, predominantly either at residues 40 or 42.

Amyloid β-derived diffusible ligands or ADDLs refer to neurotoxic, soluble, globular, non-fibrillar oligomeric structures that are desirably composed of aggregates of Aβ1-42 peptides (e.g., eight or nine Aβ1-42 peptides) and are found associated with Alzheimer's disease. See U.S. Pat. No. 6,218,506 and WO 01/10900. This is in contrast to high molecular weight aggregation intermediates, which form strings of micelles leading to fibril formation. The term "Aβ fibrils" or "fibrils" or "fibrillar amyloid" as used herein refers to insoluble species of Aβ that are detected in human and transgenic mouse brain tissue because of their birefringence with dyes such as thioflavin S. Aβ species that form fiber-like structures composed of Aβ monomers include β-pleated sheets. These species are believed to be immediate precursors to the extracellular amyloid plaque structures found in AD brain.

As exemplified herein, the antibodies of this invention specifically bind to or recognize at least one multi-dimensional conformation of an ADDL. In particular embodiments, the antibodies bind at least two, at least three, or at least four multi-dimensional conformations of an ADDL. Multi-dimensional conformations of ADDLs are intended to encompass dimers, trimers, tetramers, pentamers, hexamers, heptamers, octamers, nonamers, decamers, etc. as defined by analysis via SDS-PAGE. Because trimer, tetramer, etc. designations can vary with the assay method employed (see, e.g., Bitan, et al. (2005) *Amyloid* 12:88-95), the definition of trimer, tetramer, and the like, as used herein, is according to SDS-PAGE analysis. To illustrate the differential binding capabilities of the antibodies herein, it has been found that certain antibodies will recognize one multi-dimensional conformation, for example, tetramers of ADDLs (U.S. Pat. No. 7,780,963, murine antibodies 2D6 and 4E2), while other antibodies recognize several multidimensional conformations, for example, trimers and tetramers of ADDLs (U.S. Pat. No. 7,780,963, murine antibodies 2A10, 2B4, 5F10, and 20C2 and humanized antibody 20C2). As such, the antibody of this invention has oligomer-specific characteristics. In particular embodiments, a multi-dimensional conformation of an ADDL is associated with a specific polypeptide structure which results in a conformational epitope that is recognized by an antibody of the present invention. In other embodiments, an antibody of the invention specifically binds a multi-dimensional conformation ADDL having a size range of approximately a trimer or tetramer, which have molecular weights in excess of >50 kDa.

Preferably, an antibody of this invention is selective for Aβ oligomer, i.e., the antibody has a higher affinity for Aβ1-42 oligomers or ADDLs than for Aβ1-42 monomer, Aβ1-40 monomer, plaques and/or amyloid beta fibrils. As demonstrated herein, selectivity can be assessed using a variety of methods including, but not limited to competitive binding assays such as one-sided ELISA, sandwich ELISA or competitive ELISA assays. Based upon this analysis, an antibody of this invention is defined as being specific for Aβ oligomers if it exhibits at least a 2-fold, 3-fold, 4-fold, 5-fold higher affinity for Aβ oligomers compared to one or more of Aβ1-42 monomer, Aβ1-40 monomer, plaques or amyloid beta fibrils when assessed in a conventional assay, e.g., BIACORE, KIN-EXA, or one-sided ELISA. In particular embodiments, the affinity of the capture antibody for Aβ1-42 oligomers compared to Aβ1-monomers in a competitive binding assay is at least 500:1. In other embodiments, the affinity of the antibody for amyloid beta 1-42 oligomers compared to amyloid beta 1-42 monomers in a sandwich ELISA assay is at least 500:1, at least 600:1, at least 700:1, at least 800:1, at least 900:1 or more preferably at least 1000:1.

While antibodies of the invention may have similar linear epitopes, such linear epitopes are not wholly indicative of the binding characteristics of these antibodies, i.e., ability to block ADDL binding to neurons, prevent tau phosphorylation and inhibit ADDL incorporation into plaques, because, as is well-known to the skilled artisan, the linear epitope may only correspond to a portion of the antigen's epitope (see, for example, Breitling and Dübel (1999) *Recombinant Antibodies*, John Wiley & Sons, Inc., NY, pg. 115). The antibodies of the invention can be distinguished from those of the art as being capable of differentially recognizing multidimensional ADDLs and accordingly differentially blocking ADDL binding to neurons, differentially preventing tau phosphorylation and differentially inhibiting incorporation of ADDLs into amyloid plaques.

An antibody, as used in accordance with the invention includes, but is not be limited to, polyclonal or monoclonal antibodies, and chimeric, human (for example, isolated from B cells), humanized, neutralizing, bispecific or single chain antibodies thereof. In one embodiment, an antibody of the invention is monoclonal. For the production of antibodies, various hosts including goats, rabbits, chickens, rats, mice, humans, and others, can be immunized by injection with synthetic or natural ADDLs. Methods for producing antibodies are well-known in the art. See, for example, Kohler & Milstein (1975) *Nature* 256:495-497; Harlow & Lane (1988) *Antibodies: A Laboratory Manual*, Cold Spring Harbor Laboratory, New York.

Depending on the host species, various adjuvants can be used to increase the immunological response. Adjuvants used in accordance with the invention desirably augment the intrinsic response to ADDLs without causing conformational changes in the immunogen that affect the qualitative form of the response. Particularly suitable adjuvants include 3 De-O-acylated monophosphoryl lipid A (MPL™; RIBI ImmunoChem Research Inc., Hamilton, Mont.; see GB 2220211) and oil-in-water emulsions, such as squalene or peanut oil, optionally in combination with immune stimulants, such as monophosphoryl lipid A (see, Stoute, et al. (1997) *N. Engl. J. Med.* 336:86-91), muramyl peptides (for example, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy) ethylamine (E-PE), N-acetylglucsaminyl-N-acetylmuramyl-L-Al-D-isoglu-L-Ala-dipalmitoxy propylamide (DTP-DPP)), or other bacterial cell wall components. Specific examples of oil-in-water emulsions include MF59 (WO 90/14837), containing 5% Squalene, 0.5% TWEEN™ 80, and 0.5% SPAN 85 (optionally containing various amounts of MTP-PE) formulated into submicron particles using a microfluidizer such as Model 110Y microfluidizer (Microfluidics, Newton, Mass.); SAF containing 10% Squalene, 0.4% TWEEN™ 80, 5% PLURONIC®-blocked polymer L121, and thr-MDP, either microfluidized into a submicron emulsion or vortexed to generate a larger particle size emulsion; and RIBI™ adjuvant system (RAS) (Ribi ImmunoChem, Hamilton, Mont.) containing 2% squalene, 0.2% TWEEN™ 80, and one or more bacterial cell wall components such as monophosphoryllipid A, trehalose dimycolate (TDM), and cell wall skeleton (CWS).

Another class of adjuvants is saponin adjuvants, such as STIMULON™ (QS-21, Aquila, Framingham, Mass.) or particles generated therefrom such as ISCOMs (immunostimulating complexes) and ISCOMATRIX® (CSL Ltd., Parkville, Australia). Other suitable adjuvants include Complete Freund's Adjuvant (CFA), Incomplete Freund's Adjuvant (IFA), mineral gels such as aluminum hydroxide, and surface-active substances such as lysolecithin, PLURONIC® polyols, polyanions, peptides, CpG (WO 98/40100), keyhole limpet hemocyanin, dinitrophenol, and cytokines such as interleukins (IL-1, IL-2, and IL-12), macrophage colony stimulating factor (M-CSF), and tumor necrosis factor (TNF). Among adjuvants used in humans, BCG (bacilli Calmette-Guerin) and *Corynebacterium parvum* are particularly suitable.

An antibody to a multi-dimensional conformation ADDL is generated by immunizing an animal with ADDLs. Generally, ADDLs can be generated synthetically or by recombinant fragment expression and purification. Synthetic ADDLs can be prepared as disclosed herein, or in accordance with the methods disclosed in U.S. Pat. No. 6,218,506 and U.S. Pat. No. 7,811,563. Further, ADDLs can be fused with another protein such as keyhole limpet hemocyanin to generate an antibody against the chimeric molecule. The ADDLs can be conformationally constrained to form an epitope useful as described herein and furthermore can be associated with a surface for example, physically attached or chemically bonded to a surface in such a manner so as to allow for the production of a conformation which is recognized by the antibodies of the present invention.

Monoclonal antibodies to multi-dimensional conformations of ADDLs can be prepared using any technique the provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256:495-497; Kozbor, et al. (1985) *J. Immunol. Methods* 81:31-42; Cote, et al. (1983) *Proc. Natl. Acad. Sci. USA* 80:2026-2030; Cole, et al. (1984) *Mol. Cell Biol.* 62:109-120).

In particular embodiments, the antibodies of the invention are humanized. Humanized or chimeric antibodies can be produced by splicing of mouse antibody genes to human antibody genes to obtain a molecule with appropriate antigen specificity and biological activity (see, Morrison, et al. (1984) *Proc. Natl. Acad. Sci. USA* 81:6851-6855; Neuberger, et al. (1984) *Nature* 312:604-608; Takeda, et al. (1985) *Nature* 314:452-454; Queen, et al. (1989) *Proc. Natl. Acad. Sci. USA* 86:10029-10033; WO 90/07861). For example, a mouse antibody is expressed as the Fv or Fab fragment in a phage selection vector. The gene for the light chain (and in a parallel experiment, the gene for the heavy chain) is exchanged for a library of human antibody genes. Phage antibodies that still bind the antigen are then identified. This method, commonly known as chain shuffling, provided humanized antibodies that should bind the same epitope as the mouse antibody from which it descends (Jespers, et al. (1994) *Biotechnology NY* 12:899-903). As an alternative, chain shuffling can be performed at the protein level (see, Figini, et al. (1994) *J. Mol. Biol.* 239:68-78).

Human antibodies can also be obtained using phage-display methods. See, for example, WO 91/17271 and WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to ADDLs. Human antibodies against ADDLs can also be produced from non-human transgenic mammals having transgenes encoding at least a segment of the human immunoglobulin locus and an inactivated endogenous immunoglobulin locus. See, for example, WO 93/12227 and WO 91/10741. Human antibodies can be selected by competitive binding experiments, or otherwise, to have the same epitope specificity as a particular mouse antibody. Such antibodies generally retain the useful functional properties of the mouse antibodies. Human polyclonal antibodies can also be provided in the form of serum from humans immunized with an immunogenic agent. Optionally, such polyclonal antibodies can be concentrated by affinity purification using ADDLs as an affinity reagent.

As exemplified herein, humanized antibodies can also be produced by veneering or resurfacing of murine antibodies. Veneering involves replacing only the surface fixed region amino acids in the mouse heavy and light variable regions with those of a homologous human antibody sequence. Replacing mouse surface amino acids with human residues in the same position from a homologous human sequence has been shown to reduce the immunogenicity of the mouse antibody while preserving its ligand binding. The replacement of exterior residues generally has little, or no, effect on the interior domains, or on the inter-domain contacts. See, for example, U.S. Pat. No. 6,797,492.

Human or humanized antibodies can be designed to have IgG, IgD, IgA, IgM or IgE constant regions, and any isotype, including IgG1, IgG2, IgG3 and IgG4. In particular embodiments, an antibody of the invention is IgG or IgM, or a combination thereof. In one specific embodiment the antibodies of the present invention are IgG2. Those of skill in the art would understand that other isoforms can be utilized herein. Exemplary sequences for these isoforms are given in SEQ ID NOS:56-58. Other embodiments of the present invention embrace a constant region formed by selective incorporation of human IgG4 sequences into a standard human IgG2 constant region. An exemplary mutant IgG2 Fc is IgG2m4, set forth herein as SEQ ID NO:59. Antibodies can be expressed as tetramers containing two light and two heavy chains, as separate heavy chains and light chains or as single chain antibodies in which heavy and light chain variable domains are linked through a spacer. Techniques for the production of single chain antibodies are well-known in the art.

Exemplary humanized antibodies produced by CDR grafting and veneering are disclosed in U.S. Pat. No. 7,780,963; U.S. Pat. No. 7,731,962 and U.S. Pat. No. 7,811,563.

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger, et al. (1993) Proc. Natl. Acad. Sci. USA 90:6444: Poljak (1994) Structure 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. The skilled artisan will appreciate that any method to generate diabodies can be used. Suitable methods are described by Holliger, et al. (1993) supra; Poljak (1994) supra; Zhu, et al. (1996) Biotechnology 14:192-196, and U.S. Pat. No. 6,492,123.

Fragments of an isolated antibody of the invention are also expressly encompassed by the present invention. Fragments are intended to include Fab fragments, $F(ab')_2$ fragments, $F(ab')$ fragments, bispecific scFv fragments, Fv fragments, single domain antibodies and fragments produced by a Fab expression library, as well as peptide aptamers. For example, $F(ab')_2$ fragments are produced by pepsin digestion of the antibody molecule of the invention, whereas Fab fragments are generated by reducing the disulfide bridges of the $F(ab')_2$ fragments. Alternatively, Fab expression libraries can be constructed to allow rapid and easy identification of monoclonal Fab fragments with the desired specificity (see, Huse, et al. (1989) Science 254:1275-1281). In particular embodiments, antibody fragments of the present invention are fragments of neutralizing antibodies which retain the variable region binding site thereof, i.e. antigen binding fragment. Exemplary are $F(ab')_2$ fragments, $F(ab')$ fragments, and Fab fragments. See, generally, Immunology: Basic Processes (1985) $2^{nd}$ edition, J. Bellanti (Ed.) pp. 95-97.

Single domain antibodies or nanobodies are also encompassed by this invention. Nanobodies are prepared by splitting the dimeric variable domains from common human or mouse IgG into monomers and camelizing a few key residues. See, e.g., Davies & Riechmann (1994) FEBS Lett. 339:285-290 and Reichman & Muyldermans (1999) J. Immunol. Meth. 231:25-38.

Peptide aptamers that differentially recognize multi-dimensional conformations of ADDLs can be rationally designed or screened for in a library of aptamers (for example, provided by Aptanomics SA, Lyon, France). In general, peptide aptamers are synthetic recognition molecules whose design is based on the structure of antibodies. Peptide aptamers are composed of a variable peptide loop attached at both ends to a protein scaffold. This double structural constraint greatly increases the binding affinity of the peptide aptamer to levels comparable to that of an antibody (nanomolar range).

Exemplary nucleic acid sequences encoding light and heavy chain variable regions for use in producing antibody and antibody fragments of the present invention are disclosed herein in SEQ ID NOs: 60 and 61, respectively. As will be appreciated by the skilled artisan, the heavy chain variable regions disclosed herein, such as that shown in SEQ ID NO:61, can be used in combination with any one of the light chain variable regions disclosed herein to generate antibodies with modified affinities, dissociation, epitopes, and the like.

Antibodies or antibody fragments of the present invention can have additional moieties attached thereto. For example, a microsphere or microparticle can be attached to the antibody or antibody fragment, as described in U.S. Pat. No. 4,493,825.

Moreover, particular embodiments embrace antibody or antibody fragments that are mutated and selected for increased antigen affinity, neutralizing activity (i.e., the ability to block binding of ADDLs to neuronal cells or the ability to block ADDL assembly or incorporation into amyloid plaques), or a modified dissociation constant. Mutator strains of E. coli (Low, et al. (1996) J. Mol. Biol. 260:359-368), chain shuffling (Figini, et al. (1994) supra), and PCR mutagenesis are established methods for mutating nucleic acid molecules encoding antibodies. By way of illustration, increased affinity can be selected for by contacting a large number of phage antibodies with a low amount of biotinylated antigen so that the antibodies compete for binding. In this case, the number of antigen molecules should exceed the number of phage antibodies, but the concentration of antigen should be somewhat below the dissociation constant. Thus, predominantly mutated phage antibodies with increased affinity bind to the biotinylated antigen, while the larger part of the weaker affinity phage antibodies remains unbound. Streptavidin can then assist in the enrichment of the higher affinity, mutated phage antibodies from the mixture (Schier, et al. (1996) *J. Mol. Biol.* 255:28-43).

In particular embodiments of this invention, variants of antibody h3B3 (i.e., 14.2, 7.2, 11.4, 13.1, 17.1, 19.3), or variants of antibody 19.3 (i.e., 19.3 N33S, 19.3 N33T, 19.3 N33A, 19.3 N33E, 19.3 N33D, 19.3 N33S-N35Q, 19.3 N33S-N35S, 19.3 N33S-N35T, 19.3 N33S-N35A, 19.3 N58Q, 19.3 N58S, 19.3 N58T, 19.3N35A) are used in the method of this invention. Accordingly, in some embodiments, an antibody of the invention has a light chain variable region with a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1)$_f$ wherein Xaa$_1$ is Asn, Ser, Thr, Ala, Asp or Glu and Xaa$_2$ is Asn, His, Gln, Ser, Thr, Ala, or Asp, a CDR2 having the sequence Lys-Ala-Ser-Xaa$_1$-Arg-Phe-Ser (SEQ ID NO:2), wherein Xaa$_1$ is Asn, Gly, Ser, Thr, or Ala, and a CDR3 having the sequence Phe-Gln-Gly-Ser-Xaa$_1$-Xaa$_2$-Xaa$_3$-Xaa$_4$-Xaa$_5$ (SEQ ID NO:3), wherein Xaa$_1$ is Arg, Lys or Tyr, Xaa$_2$ is Val, Ala, or Leu, Xaa$_3$ is Pro, His, or Gly, Xaa$_4$ is Ala, Pro, or Val, and Xaa$_5$ is Ser, Gly, Arg or Phe; and a heavy chain variable region with a CDR1 having the sequence Gly-Phe-Thr-Phe-Ser-Ser-Phe-Gly-Met-His (SEQ ID NO:4), a CDR2 having the sequence Tyr-Ile-Ser-Arg-Gly-Ser-Ser-Thr-Ile-Tyr-Tyr-Ala-Asp-Thr-Val-Lys-Gly (SEQ ID NO:5), and a CDR3 having the sequence Gly-Ile-Thr-Thr-Ala-Leu-Asp-Tyr (SEQ ID NO:6). Accordingly, in some embodiments, an antibody of the invention has a light chain variable region with a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Thr, Ala, Asp or Glu and Xaa$_2$ is Asn, His, Gln, Ser, Thr, Ala, or Asp or wherein Xaa$_1$ is Asn, Ser, Thr, Ala, Asp or Glu and Xaa$_2$ is Thr, a CDR2 having the sequence Lys-Ala-Ser-Xaa$_1$-Arg-Phe-Ser (SEQ ID NO:2), wherein Xaa$_1$ is Thr, and a CDR3 having the sequence Phe-Gln-Gly-Ser-Xaa$_1$-Xaa$_2$-Xaa$_3$-Xaa$_4$-Xaa$_5$ (SEQ ID NO:3), wherein Xaa$_1$ is Arg, Lys or Tyr, Xaa$_2$ is Val, Ala, or Leu, Xaa$_3$ is Pro, His, or Gly, Xaa$_4$ is Ala, Pro, or Val, and Xaa$_5$ is Ser, Gly, Arg or Phe; and a heavy chain variable region with a CDR1 having the sequence Gly-Phe-Thr-Phe-Ser-Ser-Phe-Gly-Met-His (SEQ ID NO:4), a CDR2 having the sequence Tyr-Ile-Ser-Arg-Gly-Ser-Ser-Thr-Ile-Tyr-Tyr-Ala-Asp-Thr-Val-Lys-Gly (SEQ ID NO:5), and a CDR3 having the sequence Gly-Ile-Thr-Thr-Ala-Leu-Asp-Tyr (SEQ ID NO:6).

In some embodiments, the antibody of the method of the invention is a variant of antibody h3B3 (i.e., 14.2, 7.2, 11.4, 13.1, 17.1, 19.3). In accordance with this embodiment, the antibody has a light chain variable region with a CDR1 having the sequence Arg-Ser-Ser-Gln-Ser-Ile-Val-His-Ser-Asn-Gly-Asn-Thr-Tyr-Leu-Glu (SEQ ID NO:41), a CDR2 having the sequence Lys-Ala-Ser-Asn-Arg-Phe-Ser (SEQ ID NO:51), and a CDR3 of Phe-Gln-Gly-Ser-Xaa$_1$-Xaa$_2$-Xaa$_3$-Xaa$_4$-Xaa$_5$ (SEQ ID NO:3), wherein Xaa$_1$ is Arg, Lys or Tyr, Xaa$_2$ is Val, Ala, or Leu, Xaa$_3$ is Pro, His, or Gly, Xaa$_4$ is Ala, Pro, or Val, and Xaa$_5$ is Ser, Gly, Arg or Phe; and a heavy chain variable region with a CDR1 of SEQ ID NO:4, a CDR2 of SEQ ID NO:5, and a CDR3 of SEQ ID NO:6.

In other embodiments, the antibody of the method of the invention is a variant of antibody 19.3, wherein the CDR1 of the light chain variable region has been mutated (i.e., 19.3 N33S, 19.3 N33T, 19.3 N33A, 19.3 N33E, 19.3 N33D, 19.3 N33S-N35Q, 19.3 N33S-N35S, 19.3 N33S-N35T, 19.3 N33S-N35A). In accordance with this embodiment, the antibody has a light chain variable region with a CDR1 of SEQ ID NO:1, a CDR2 of SEQ ID NO:2, and a CDR3 having the sequence Phe-Gln-Gly-Ser-Arg-Leu-Gly-Pro-Ser (SEQ ID NO:18); and a heavy chain variable region with a CDR1 of SEQ ID NO:4, a CDR2 of SEQ ID NO:5, and a CDR3 of SEQ ID NO:6.

In still other embodiments, the antibody of the method of the invention is a variant of antibody 19.3, wherein the CDR2 of the light chain variable region has been mutated (i.e., 19.3 N58Q, 19.3 N58S, 19.3 N58T, 19.3N35A). In accordance with this embodiment, the antibody has a light chain variable region with a CDR1 of SEQ ID NO:41, a CDR2 of SEQ ID NO:2, a CDR3 of SEQ ID NO:17; and a heavy chain variable region with a CDR1 of SEQ ID NO:4, a CDR2 of SEQ ID NO:5, and a CDR3 of SEQ ID NO:6.

In certain embodiments, the CDR1 of the light chain variable region of the antibody has the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Thr, Ala, Asp or Glu and Xaa$_2$ is Thr. In other embodiments, the CDR2 of the light chain variable region of the antibody has the sequence Lys-Ala-Ser-Xaa$_1$-Arg-Phe-Ser (SEQ ID NO:2), wherein Xaa$_1$ is Thr.

An exemplary antibody of use in this invention is antibody 19.3 having a heavy chain variable region sequence as in SEQ ID NO:7 (i.e., CDR1, CDR2, and CDR3 of SEQ ID NOs:4, 5 and 6, respectively) and light chain variable region sequence as in SEQ ID NO:9 (i.e., CDR1, CDR2, and CDR3 of SEQ ID NOs:41, 51, 18). See FIG. 6. In certain embodiments, the antibody used in the method of this invention is not 3B3.

To facilitate production and enhance storage and use of the antibody in the method of this invention, certain embodiments include the use of an antibody that exhibits less than a 10-fold decrease in EC$_{50}$, in an ELISA-based assay with Aβ oligomers, when stored at 40° C. for 1 month. More preferably, the antibody exhibits less than a 6-fold, 5-fold, 4-fold, 3-fold, or 2-fold decrease in EC$_{50}$ when stored at 40° C. for 1 month. Antibody stability can be assessed as described in the Examples herein. Antibodies having such stability at elevated temperatures are provided in Example 7.

For some therapeutic applications it may be desirable to reduce the dissociation of the antibody from the antigen. To achieve this, phage antibodies are bound to biotinylated antigen and an excess of unbiotinylated antigen is added. After a period of time, predominantly the phage antibodies with the lower dissociation constant can be harvested with streptavidin (Hawkins, et al. (1992) *J. Mol. Biol.* 226:889-96).

Various immunoassays including those disclosed herein can be used for screening to identify antibodies, or fragments thereof, having the desired specificity for multi-dimensional conformations of ADDLs. Numerous protocols for competitive binding (for example, ELISA), latex agglutination assays, immunoradiometric assays, kinetics (for example, BIACORE™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. Such assays can also be used in the detection of multi-dimensional conformations of ADDLs in a sample.

An antibody or antibody fragment can also be subjected to other biological activity assays, e.g., displacement of ADDL binding to neurons or cultured hippocampal cells or blockade of ADDL assembly or ADDL incorporation into amyloid plaques, in order to evaluate neutralizing or pharmacological activity and potential efficacy as a prophylactic or therapeutic agent. Such assays are described herein and are well-known in the art.

Antibodies and fragments of antibodies can be produced and maintained as hybridomas or, alternatively, recombinantly produced in any well-established expression system including, but not limited to, *E. coli*, yeast (e.g., *Saccharomyces* spp. and *Pichia* spp.), baculovirus, mammalian cells (e.g., myeloma, CHO, COS), plants, or transgenic animals (Breitling & Dübel (1999) *Recombinant Antibodies*, John Wiley & Sons, Inc., NY, pp. 119-132). Antibodies and fragments of antibodies can be isolated using any appropriate methods including, but not limited to, affinity chromatography, immunoglobulins-binding molecules (for example, proteins A, L, G or H), tags operatively linked to the antibody or antibody fragment (for example, His-tag, FLAG®-tag, Strep tag, c-myc tag) and the like. See, Breitling & Dübel (1999) supra.

To assess prophylactic or therapeutic treatment of a disease associated with ADDLs, the activity of the antibodies and antibody fragments of this invention can be analyzed for the ability to block or inhibit binding of ADDLs to neuronal cells, inhibit assembly of higher order oligomers, block ADDL incorporation into amyloid plaques, and/or prevent the phosphorylation of tau protein at Ser202/Thr205.

The ability of an antibody or antibody fragment to block or inhibit binding of ADDLs to neuronal cells is determined by measuring whether ADDLs are bound to neurons in the presence of the antibody or antibody fragment. The degree to which an antibody can block the binding of ADDLs to a neuron can be determined in accordance with the methods disclosed herein, i.e., immunocytochemistry, or cell-based alkaline phosphatase assay, or any other suitable assay. In particular embodiments, an antibody or antibody fragment of the present invention achieves at least a 15%, 20%, 30%, 40%, 50%, 60%, 70%, 80%, 90%, 95%, or 97% decrease in the binding of ADDLs as compared to binding of ADDLs in the absence of the antibody or antibody fragment.

The ability of an antibody or antibody fragment to block or inhibit assembly of ADDLs can be determined by measuring whether assembly of larger oligomeric species of Aβ1-42, e.g., octamers or decamers, is inhibited in the presence of the antibody or antibody fragment. The degree to which an antibody can block the assembly of larger oligomeric species of ADDLs can be determined by, e.g., FRET or fluorescence polarization or any other suitable assay.

The ability of an antibody or antibody fragment to prevent the phosphorylation of tau protein at Ser202/Thr205 can be determined by measuring whether tau protein is phosphorylated in the presence of the antibody or antibody fragment. The degree to which an antibody can prevent the phosphorylation of tau protein at Ser202/Thr205 can be determined in accordance with the methods disclosed herein or any other suitable assay.

Blocking or decreasing binding of ADDLs to neurons, inhibiting assembly of larger oligomeric species of ADDLs, and/or preventing the phosphorylation of tau protein at Ser202/Thr205 can be used as an indication that a disease associated with the accumulation of ADDLs is prophylactically or therapeutically being treated.

In accordance with the method herein, an antibody or antibody fragment of the invention can optionally be administered in combination with other agents that are at least partly effective in treatment of amyloidogenic disease. For example, the present antibody can be administered with existing palliative treatments for Alzheimer's disease, such as acetylcholinesterase inhibitors such as ARICEPT™, EXELON™, and REMIYL™ and, the NMDA antagonist, NAMENDA™. In addition to these known treatments, particular embodiments feature the use of one or more antibodies of this invention in combination with an inhibitor of Aβ production and aggregation (e.g., a β-secretase inhibitor, γ-secretase inhibitor, Aβ-monomer aggregation inhibitor, Pan-Aβ immunotherapy, and/or fibrillic or amyloid plaque immunotherapy) and/or tau therapy.

Secretase Enzyme Modulation.

One approach for reducing the levels of Aβ involves modulating the activity of the β- and γ-secretase cleaving enzymes to inhibit the production of Aβ. The 1- and γ-secretase enzymes are aspartyl proteases that convert APP to Aβ; treatment strategies that involve the inhibition of these two enzymes aim to reduce the levels of cerebral amyloid (Marlatt, et al. (2005) *Curr. Med. Chem.* 12(10):1137-47; Lundkvist & Näslund (2007) *Curr. Opin. Pharmacol.* 7(1):112-8). Several agents targeting these enzymes are known, including the β-secretase inhibitors CTS-21166 (CoMentis, Inc.), Posiphen (QR Pharma Inc.; Sabbagh (2009) *Am. J. Geriatr. Pharmacother.* 7:167-185; Neugroschl & Sano (2009) *Curr. Neurol. Neurosci. Rep.* 9:368-376) and ACI-91 (AC Immune SA), as well as beta-amyloid cleaving enzyme-1 (BACE1) inhibitors, MK-8931 (Merck & Co. Inc.), LY2811376 (Eli Lilly & Co.), and TAK-070 (Takeda Pharmaceutical Company Limited). Gamma-secretase inhibitors include, but are not limited to, MK-0752 (Merck & Co Inc.), semagacestat (LY-450139; Eli Lilly & Co; NCT00762411 and NCT00594568) (Lundkvist & Naslund (2007) supra; Barten, et al. (2005) *J. Pharmacol. Exp. Ther.* 312(2):635-643; Wong, et al. (2004) *J. Biol. Chem.* 279(13):12876-82), avagacestat (BMS-708163; Bristol-Myers Squib), EVP-0962 (EnVivo Pharmaceuticals).

Modulation of Beta-Amyloid Aggregation.

Several inhibitors of beta-amyloid aggregation have been developed including PBT2 (Prana Biotechnology Ltd.), which prevents the interation of synaptic zinc and copper with beta-amyloid to prevent it from becoming toxic; and ELND0005 (scyllo-inositol; Elan Corporation, PLC).

Tau-Based Therapies.

Another significant aspect of AD pathology that provides a target for therapeutic intervention is the hyperphosphorylated form of the microtubule-associated protein tau. Tau hyperphosphorylation and the presence of this protein in an aggregated form in neurofibrillary tangles are correlated with cognitive decline in patients with AD (Castellani, et al. (2006) *Acta Neuropathol.* 111:503-509; Nunomura, et al. (2006) *Sci. Aging Knowledge Environ.* 2006:e10). Thus, therapeutic strategies that target hyperphosphorylated tau proteins are potentially relevant for the treatment of AD.

The disruptive effects of aggregated, hyperphosphorylated tau can also be eliminated by the upregulation of the intracellular degradation of the protein through the ubiquitin proteosome system or through macroautophagy (Brunden, et al. (2009) *Nat. Rev. Drug Discov.* 8:783-93). In the ubiquitin proteosome degradation pathway, a targeted protein is tagged with ubiquitin and subsequently recognized and degraded by the proteosome complex (Ravikumar, et al. (2003) *Clin. Neurosci. Res.* 3:141-148). As the ubiquitin proteosome system requires that the target protein is threaded through the narrow opening of the proteosome, the activation of this system degrades only the non-fibrillar phosphorylated tau. Nevertheless, the Hsp90 inhibitor-mediated degradation of the smaller non-fibrillar phosphorylated tau. Because Hsp90 is primarily responsible for the ATP-driven refolding of denatured proteins, the inhibition of this protein halts the attempted preservation of phosphorylated tau by this chaperone effectively, thereby enhancing tau degradation (Dickey, et al. (2007) *J. Clin. Invest.* 117:648-658). For example, the Hsp90 inhibitor EC-102, which was administered to human tau-expressing Tg mice for 7 days, reduced the levels of hyperphosphorylated tau in the brain (Dickey, et al. (2007) supra; Luo, et al. (2007) *Proc. Natl. Acad. Sci. USA* 104:9511-16). Moreover, EC-102 inhibited the formation of Hsp90/non-fibrillar phosphorylated tau complexes in cortical homogenates from the brains of patients with AD effectively, at a concentration that was 1000-fold lower than for control homogenates (Dickey, et al. (2007) supra); thus, clinically safe doses of EC-102 are a possibility.

Additional agents that target tau include davunetide (Allon Therapeutics), REMBER (TauRx Pharmaceuticals Ltd.), and tideglusib (NYPTA/ZENTYLOR; Noscira), which is a glycogen synthetase kinase-3 inhibitor. Still another embodiment of the present invention is a kit for detecting ADDLs comprising an isolated anti-ADDL antibody, or an antigen binding fragment thereof, that binds ADDLs.

In accordance with such combination treatments, this invention also includes a kit containing one or more antibodies that selectively and specifically bind soluble oligomers of Aβ1-42 in combination with an inhibitor of Aβ production and aggregation and/or a tau therapeutic. Such a kit can contain various containers, already containing the doses of the individual active ingredients, in a single package (kit) bearing the instructions for the modes of administration.

In addition to treatment, antibody and antibody fragments of the present invention also find application in the identification of therapeutic agents that prevent the binding of ADDLs to neurons (e.g., a hippocampal cell) thereby preventing downstream events attributed to ADDLs. Such an assay is carried out by contacting a neuron with ADDLs in the presence of an agent and using an antibody or antibody fragment of the invention to determine binding of the ADDLs to the neuron in the presence of the agent. As will be appreciated by the skilled artisan, an agent that blocks binding of ADDLs to a neuron will decrease the amount of ADDLs bound to the neuron as compared to a neuron which has not been contacted with the agent; an amount which is detectable in an immunoassay employing an antibody or antibody fragment of the present invention. Suitable immunoassays for detecting neuronal-bound ADDLs are disclosed herein.

Agents which can be screened using the method provided herein encompass numerous chemical classes, although typically they are organic molecules, preferably small organic compounds having a molecular weight of more than 100 and less than about 2,500 daltons. Agents encompass functional groups necessary for structural interaction with proteins, particularly hydrogen bonding, and typically include at least an amine, carbonyl, hydroxyl or carboxyl group, preferably at least two of the functional chemical groups. The agents often contain cyclical carbon or heterocyclic structures and/or aromatic or polyaromatic structures substituted with one or more of the above functional groups. Agents can also be found among biomolecules including peptides, antibodies, saccharides, fatty acids, steroids, purines, pyrimidines, derivatives, structural analogs or combinations thereof. Agents are obtained from a wide variety of sources including libraries of natural or synthetic compounds.

A variety of other reagents such as salts and neutral proteins can be included in the screening assays. Also, reagents that otherwise improve the efficiency of the assay, such as protease inhibitors, nuclease inhibitors, anti-microbial agents, and the like can be used. The mixture of components can be added in any order that provides for the requisite binding.

Agents identified by the screening assay of the present invention will be beneficial for the treatment of amyloidogenic diseases and/or tauopathies. In addition, it is contemplated that the experimental systems used to exemplify these concepts represent research tools for the evaluation, identification and screening of novel drug targets associated with amyloid beta induction of tau phosphorylation.

All references cited herein are incorporated herein by reference in their entirety. The invention is described in greater detail by the following non-limiting examples.

Example 1

Materials and Methods

Generation of ADDL-Selective Monoclonal Antibodies.

Soluble Aβ oligomers, a species of which is referred to herein as "synthetic" ADDLs, were mixed 1:1 with complete Freund's adjuvant (first and second vaccination) or incomplete Freund's adjuvant (all subsequent vaccinations) and were given by subcutaneous (first two vaccinations) or intraperitoneal injection into three mice in a total volume of 1 mL/mouse. Each injection included purified ADDLs equivalent to 194±25 µg total protein. Mice were injected approximately every three weeks. After six injections, one mouse died and its spleen was frozen. The spleen from the mouse with the highest titer serum was then fused with SP2/0 myeloma cells in the presence of polyethylene glycol and plated out into six 96-well plates. The cells were cultured at 37° C. with 5% $CO_2$ for 10 days in 200 µL of hypoxanthine-aminopterin-thymidine (HAT) selection medium, which is composed of an enriched synthetic medium, such as Iscove's Modified Dulbecco's Medium (IMDM), (Sigma-Aldrich, St. Louis, Mo.), supplemented with 10% fetal bovine serum (FBS), 1 µg/mL HYBRI-MAX® (azaserine-hypoxanthine; Sigma-Aldrich, Mo.), and 30% conditioned media collected from SP2/0 cell culture. The cultures were fed once with IMDM (Sigma-Aldrich, St. Louis, Mo.) supplemented with 10% FBS on day 10, and the culture supernatants were removed on day 14 to screen for positive wells in ELISA. The positive cultures were further cloned by limiting dilutions with the probability of 0.3 cells per well. The positive clones were confirmed in ELISA and further expanded. Monoclonal antibodies were then produced and purified for use (QED Bioscience, San Diego, Calif.).

Preparation of ADDLs and bADDLs.

ADDLs were prepared using previously described methods (Hepler, et al. (2006) *Biochemistry* 45:15157-15167; Shughrue, et al. (2010) *Neurobiol. Aging* 31:189-202). Briefly, synthetic Aβ1-42 peptide (American Peptide, Sunnyvale, Calif.) was dissolved in hexafluoro-2-propanol (HFIP) at a concentration of 10 mg/ml, and incubated at room temperature (RT) for one hour. The peptide solution was dispensed into 50 it aliquots in polypropylene 1.5 ml microcentrifuge tubes. The HFIP was removed using a SPEEDVAC® (Thermo-Fisher Scientific, Waltham, Mass.), and the resulting peptide films were stored desiccated at −70° C. until needed. A 0.5 mg dried HFIP film was dissolved in 22 µl of anhydrous dimethyl sulfoxide (DMSO) with agitation for 10 minutes on a vortex mixer. Subsequently, 1 ml of cold Ham's F12 media without phenol red (United Biosource, San Francisco, Calif.) was added rapidly to the DMSO/peptide mixture. The tube was capped, inverted to insure complete mixing and incubated overnight at 4° C. The next morning, the samples were centrifuged for ten minutes at 12,000×g in a Beckman microcentrifuge (Beckman Coulter, Brea, Calif.) operated at 2-8° C. The supernatant was collected and filtered through YM50 (50,000 kDa molecular cutoff) CENTRICON® centrifugal filter (Millipore, Billerica, Mass.) to enrich the oligomeric species. Biotinylated ADDLs (bADDLs) were prepared using the same methods, but starting with N-terminal biotinylated Aβ1-42 peptide (American Peptide, Sunnyvale, Calif.). Such preparations of bADDLs have been shown via immunocytochemistry analysis to bind to mature synapses of rat hippocampal neurons in the same manner as ADDLs (Shughrue, et al. (2010) supra).

Monomer and Fibril Preparations.

To generate monomer preparations, room temperature Aβ1-40 or Aβ1-42 peptide film was dissolved in 2 mL of 25 mM borate buffer (pH 8.5) per mg of peptide, divided into aliquots, and frozen at −70° C. until used. The fibril preparations were made by adding 2 mL of 10 mM hydrochloric acid per mg of Aβ1-42 peptide film. The solution was mixed on a vortex mixer at the lowest possible speed for five to ten minutes and the resulting preparation was stored at 37° C. for 18 to 24 hours before use.

Primary Neurons.

Primary neuronal cultures were prepared from rat hippocampal and/or cortical tissues purchased from BrainBits (Springfield, Ill.). After dissociation, cells were plated at a 35,000 cells/well in 96-well plates pre-coated with laminin and poly-D-lysine (Corning Life Sciences, Lowell, Mass.). Cells were maintained at 37° C. with 5% $CO_2$ in media (Neurobasal supplemented with 2% B27, 1% L-glutamine, and 1% pen/strep; Invitrogen, Carlsbad, Calif.) for two-three weeks and then used for binding studies.

Cell-Based ADDL Binding Assay.

To measure the effect of anti-ADDL antibodies on blocking ADDL binding, anti-ADDL antibodies were mixed with 500 nM bADDLs, with the final antibody concentrations ranging from 1.8 nM to 450 nM. As a control, the same concentration of heat-denatured antibody (98° C. for 30 minutes) was mixed with bADDLs. The antibody-bADDL mixtures were incubated in siliconized microcentrifuge tubes (Fischer Scientific, Pittsburgh, Pa.) at 37° C. for one hour with constant end-to-end rotation at a low speed. The mixtures were then applied to primary hippocampal and/or cortical cultures and incubated at 37° C. for one hour. The incubation was terminated by removing the culture medium. Cells were subjected to fixation and post-fixation treatments using known methods Cells were then incubated with streptavidin conjugated with alkaline phosphate (AP) at 4° C. overnight, washed five times with PBS and reacted with the TROPIX® CDP®-Star chemiluminescent substrate (LIFE TECHNOLOGIES', Carlsbad, Calif.) at room temperature for 30 minutes. The bADDL binding intensity was measured and recorded with an ENVISION® microplate reader (PerkinElmer, Waltham, Mass.).

ELISA.

Biotinylated ADDLs (bADDLs) or monomer Aβ1-40 or Aβ1-42 was added to a high-capacity streptavidin-coated plate (Sigma-Aldrich, St. Louis, Mo.) with 100 µl per well of coating reagent in PBS at 1 µM and incubated for two hours at room temperature. The plates were washed in PBS with 0.05% TWEEN (six times) and then PBS alone (three times) prior to blocking the wells with 5% non-fat dry milk in PBS for one hour at room temperature. The wells were then washed and a serial dilution of antibody samples was added to the plates and allowed to bind for two hours at room temperature. After incubation and washing, the antibody binding was detected with a goat anti-human IgG-Fc secondary antibody conjugated to horse radish peroxidase (HRP) (1:1000; one hour at room temperature). The HRP label was visualized with tetramethyl benzidine (Virolabs, Chantilly, Va.) as a substrate and read at 450 nm on a microplate reader.

Example 2

Selection of Anti-ADDL Antibodies

Panning Humanized Antibody Library.

An affinity mature library of a humanized anti-ADDL antibody, h3B3, (See, US 2006/0228349 and US 2008/0175835) was constructed in which part of the light chain CDR3 amino acid sequences was subject to random mutagenesis. To cover the entire CDR3 region, two sub-libraries were built. One library was composed of the parental heavy chain variable region and mutated amino acids in the left half of the light chain CDR3 and the other in the right half of the light chain CDR3. A similar strategy was used for heavy chain CDRs random mutagenesis with three sub-libraries.

Humanized 3B3 (h3B3) was subject to affinity maturation using methods known in the art. The h3B3 variable regions were cloned in a Fab display vector (pFab3D). In this vector, the variable regions for heavy and light chains were in-frame inserted to match the CH1 domain of the constant region and the kappa constant region, respectively. In Fab3D, myc epitope and six consecutive histidine amino acids follow the CH1 sequence, which is then linked to the phage pIII protein for display. All positions in the heavy and light chain CDR3s were randomly mutagenized using degenerate oligonucleotide sequences built in the PCR primers. To accommodate the physical size, the sub-libraries were constructed with each focusing on 5-6 amino acids. The vector DNA of human 3B3 (h3B3) was used as template DNA to amplify both heavy and light chains with the mutated PCR primers (Table 1). After PCR amplification, the synthesized DNA fragments were separated on a 1.3% agarose gel, the primers removed and the variable fragments digested with restriction enzymes, BsiWI and XbaI cloning sites for light chain variable cloning, and XhoI and ApaI for heavy chain variable cloning.

TABLE 1

| 3B3 Affinity Maturation Library | Primer | Primer Sequence | SEQ ID NO: |
|---|---|---|---|
| Light Chain Libraries | Forward | tatggcttctagagatgtggtgatg | 11 |
| | Reverse | tgcagccaccgtacgcttgatctcca gcttggtgccctggccaaaggtgggg ggcacmnnmnnmnnmnnmnngcagta gtag | 12 |
| | | tgcagccaccgtacgcttgatctcca gcttggtgccctggccaaamnnmnnm nnmnnmnngctgccctgg | 13 |
| Heavy Chain Libraries | Forward | aggcggccctcgaggaggtgcagc | 14 |
| | Reverse | agaccgatgggcccttggtggaggcg ctggacacggtcaccagggtgccctg gccccamnnmnnmnnmnnmnnggtga tgccc | 15 |
| | | agaccgatgggcccttggtggaggcg ctggacacggtcaccagggtgccctg gccccagtagtccagmnnmnnmnnmn nmnnccgggcacag | 16 |

M = A/C, N = A/C/G/T.

To construct an affinity maturation library in pFab3D phage display vector, pFab3D-3B3 DNA was digested with the same pair of the restriction enzymes, purified and the PCR fragments for heavy or light chain variables ligated with T4 ligase (Invitrogen) overnight at 16° C. The ligation products were then transfected into *E. coli* TG1 electroporation-competent cells (Stratagene, Agilent Technologies, Santa Clara, Calif.) and aliquots of the bacterial culture plated on LB agar-carbenicillin (50 µg/mL) plates to titer library size. The remaining cultures were either plated on a large plate with carbenicillin and incubated at 30° C. overnight for *E. coli* library stock or infected with helper phage M13K07 (Invitrogen, Carlsbad, Calif., $10^{11}$ pfu/mL) by incubating at room temperature and 37° C. for ten minutes. Then 2YT medium with carbenicillin (50 µg/mL) was added and incubated at 37° C. for one hour with shaking. Kanamycin (70 µg/mL) was then added and the cultures grown overnight at 30° C. with shaking. The phage culture supernatant was titered and concentrated by precipitation with 20% (v/v) PEG (polyethylene glycol/NaCl, resuspended in PBS, sterilized with a 0.22 µm filter, and aliquots made for phage library panning.

Phage library panning was then conducted as summarized in Table 2.

TABLE 2

| | Panning Rounds | | | |
|---|---|---|---|---|
| | Round 1 | Round 2 | Round 3 | Round 4 |
| Antigen Concentration | 180 nM | 60 nM | 20 nM | 10 nM |

Input phages from the Fab display phage libraries (100 µl, about $10^{11-12}$ pfu) were blocked with 900 µl, of blocking solution (3% non-fat dry milk in PBS) to reduce nonspecific binding to the phage surface. Streptavidin-coated beads were prepared by collecting 200 µT of the bead suspension in a magnetic separator and removing supernatants. The beads were then suspended in 1 mL of blocking solution and put on a rotary mixer for 30 minutes. To remove non-specific streptavidin binding phage, the blocked phage library was mixed with the blocked streptavidin-coated beads and placed on a rotary mixer for thirty minutes. Phage suspensions from the deselection process were transferred to a new tube and 200 µl of antigen, 10% bADDL was added and incubated for two hours for antibody and antigen binding. After the incubation, the mixture was added into the blocked Streptavidin-coated beads and incubated on a rotary mixer for one hour to capture the antibody/antigen complex on streptavidin beads. The beads with captured 10% bADDL/phage complexes were washed five times with PBS/0.05% TWEEN 20 and then twice with PBS alone. The bound phages were eluted from the bADDL with 200 µl^ of 100 mM TEA (Sigma Aldrich, St. Louis, Mo.) and incubated for twenty minutes. The eluted phage were then transferred to a 50 mL tube, neutralized with 100 µl of 1M Tris-HCl, pH 7.5, and added to 10 mL of *E. coli* TG1 cells with an OD 600 nm between 0.6-0.8. After incubation at 37° C. with shaking for one hour, culture aliquots were plated on LB agar-carbenicillin (50 µg/mL) plates to titer the output phage number, and the remaining bacteria centrifuged and suspended with 500 µl 2×YT medium (Teknova, Hollister, Calif.), plated on bioassay YT agar plates (Teknova, Hollister, Calif.) containing 100 µg/ml ampicillin and 1% glucose. The bioassay plates were grown overnight at 30° C.

After each round of panning, single colonies were randomly picked to produce phage in 96-well plates. The procedures for phage preparation in 96-well plate were similar to that described above except no phage precipitation step was used. Culture plates containing colonies growing in 120 µl of 2×TY medium with 100 µg/ml ampicillin and 0.1% glucose were incubated overnight in a HIGRO® shaker (Genomic Solutions, Ann Arbor, Mich.) at 30° C. with shaking at 450 rpm. The phage supernatants (about 100 µl) were directly used for analysis in the ADDL binding ELISA described above. One difference is that the binding of phage to ADDLs was detected with an anti-M13 antibody conjugated to HRP (Amersham Bioscience, GE Healthcare, Waukesha, Wis.).

Example 3

Identification of Anti-ADDL Antibodies

From the light chain affinity maturation effort, a panel of seven clones (11.4, 17.1, 14.2, 13.1, 19.3, 7.2 and 9.2) showed strong binding activities to ADDLs when compared with h3B3 in a phage/Fab ELISA. Table 3 shows the amino acid similarity for the clones selected from the light chain affinity maturation library relative to parental antibody, h3B3.

TABLE 3

| Antibody | 11.4 | 17.1 | 14.2 | 13.1 | 19.3 | 7.2 | 9.2 | h3B3-humanized LC |
|---|---|---|---|---|---|---|---|---|
| 11.4 | — | 98 | 98 | 96 | 96 | 96 | 97 | 97 |
| 17.1 | — | — | 98 | 96 | 97 | 96 | 97 | 97 |
| 14.2 | — | — | — | 96 | 97 | 98 | 98 | 98 |
| 13.1 | — | — | — | — | 97 | 97 | 97 | 96 |
| 19.3 | — | — | — | — | — | 96 | 97 | 96 |
| 7.2 | — | — | — | — | — | — | 98 | 96 |
| 9.2 | — | — | — | — | — | — | — | 97 |

Table 4 summarizes the amino acid sequences in CDR3 of the light chain (LC) of the selected clones compared to the CDR3 of the light chain for the parental antibody, h3B3.

TABLE 4

| Antibody | LC-CDR3 Sequence | SEQ ID NO: |
|---|---|---|
| h3B3 (parental) | FQGSHVPPT | 17 |
| 19.3 | FQGSRLGPS | 18 |
| 17.1 | FQGSRVPAS | 19 |
| 14.2 | FQGSRVPPG | 20 |
| 13.1 | FQGSKAHPS | 21 |
| 7.2 | FQGSYAPPG | 22 |
| 9.2 | FQGSRAPPF | 23 |
| 11.4 | FQGSRVPVR | 24 |

Table 5 provides the sequence of a portion (positions 21-117) of the light chain variable regions (LCVR) for the selected clones and the parental antibody, h3B3. The CDR3 of each clone is shown in bold.

TABLE 5

| Ab | LCVR Sequence | SEQ ID NO: |
|---|---|---|
| h3B3 | PASISCRSSQSIVHSNGNTYLEWYLQKPGQSPQLLIYKASNRF SGVPDRFSGSGSGTDFTLKISRVEAEDVGVYYCFQGSHVPPTF GQGTKLEIK | 25 |
| 19.3 | PASISCRSSQSIVHSNGNTYLEWYLQKPGQSPQLLIYKASNRF SGVPDRFSGSGSGTDFTLKISRVEAEDVGVYYCFQGSRLGPSF GQGTKLEIK | 26 |

TABLE 5-continued

| Ab | LCVR Sequence | SEQ ID NO: |
|---|---|---|
| 17.1 | PASISCRSSQSIVHSNGNTYLEWYLQKPGQSPQLLIYKASNRF SGVPDRFSGSGSGTDFTLKISRVEAEDVGVYYCFQGSRVPASF GQGTKLEIK | 27 |
| 14.2 | PASISCRSSQSIVHSNGNTYLEWYLQKPGQSPQLLIYKASNRF SGVPDRFSGSGSGTDFTLKISRVEAEDVGVYYCFQGSRVPPGF GQGTKLEIK | 28 |
| 13.1 | PASISCRSSQSIVHSNGNTYLEWYLQKPGQSPQLLIYKASNRF SGVPDRFSGSGSGTDFTLKISRVEAEDVGVYYCFQGSKAHPSF GQGTKLEIK | 29 |
| 7.2 | PASISCRSSQSIVHSNGNTYLEWYLQKPGQSPQLLIYKASNRF SGVPDRFSGSGSGTDFTLKISRVEAEDVGVYYCFQGSYAPPGF GQGTKLEIK | 30 |
| 9.2 | PASISCRSSQSIVHSNGNTYLEWYLQKPGQSPQLLIYKASNRF SGVPDRFSGSGSGTDFTLKISRVEAEDVGVYYCFQGSRAPPFF GQGTKLEIK | 31 |
| 11.4 | PASISCRSSQSIVHSNGNTYLEWYLQKPGQSPQLLIYKASNRF SGVPDRFSGSGSGTDFTLKISRVEAEDVGVYYCFQGSRVPVRF GQGTKLEIK | 32 |

Example 4

IgG Conversion of Affinity Matured 3B3 Antibodies

The seven leading Fab clones (11.4, 17.1, 14.2, 13.1, 19.3, 7.2 and 9.2) were selected for IgG conversion. The converted IgGs were expressed using plasmid-based vectors. The expression vectors were built such that they contained all the necessary components except the variable regions. In the basic vectors, the expression of both light and heavy chains was driven by human CMV promoter and bovine growth hormone polyadenylation signal. For the seven clones selected for IgG conversion, the heavy chain variable region was in-frame fused with a human IgG2 heavy chain constant region (SEQ ID NOs:33 and 34), while the light chain variable region was in-frame fused with the kappa light chain constant region (SEQ ID NOs:35 and 36). The heavy (SEQ ID NOs:37 and 38) and light (SEQ ID NOs:39 and 40) chain leader sequences, which mediate the secretion of the antibodies into the culture media, were also in-frame fused with the variable regions accordingly. For the heavy chain expression vectors, the constant region could be selected from a different subclass isotype, e.g., IgG1 or IgG2. Between the leader sequence and the constant region, the intergenic sequences contain cloning sequences for seamless in-frame fusion of the incoming variable region with the leader sequence at its 5'-end and the constant region at its 3'-end using an IN-FUSION cloning strategy (Clontech, Mountain View, Calif.). The IN-FUSION Dry-Down PCR Cloning Kit (Clontech, Mountain View, Calif.) was used for PCR amplification of the variable regions. The dry-down cloning kit contained all the necessary components for PCR reaction. PCR primers and template DNAs were added. The expression vectors carry oriP from the EBV viral genome. The oriP/EBNA1 pair is often used to prolong the presence of the expression vector inside the transfected cells and widely used for the extension of the expression duration (Lindner, et al. (2007) *Plasmid* 58:1-12) for prolonged expression in 293EBNA cells, bacterial sequences for a kanamycin selection marker, and a replication origin in *E. coli*. When the variable regions were inserted, the IgGs were directly expressed in mammalian cells. All heavy chain variable regions herein were cloned into an IgG1 expression vector (pV1 JNSA-BF-HCG1) and the light chain variable regions were cloned into a matching kappa or lambda expression vector (pV1 JNSA-GS-FB-LCK).

Example 5

Affinity Matured 3B3 Antibody Cloning and Expression

The seven leading clones (11.4, 17.1, 14.2, 13.1, 19.3, 7.2 and 9.2) were produced as monoclonal antibodies and purified for further characterization. The cloning procedure for the resulting antibody expression vectors was as follows. The variable regions were PCR-amplified, wherein the PCR reactions were carried out in a volume of 25 µL containing high fidelity PCR master mix, template (1 µL), and forward and reverse primers (1 µL each). PCR conditions: 1 cycle of 94° C., 2 minutes; 25 cycles of 94° C., 1.5 minutes; 60° C., 1.5 minutes; 72° C., 1.5 minutes and 72° C., 7 minutes; 4° C. until removed. The PCR products were then digested with DpnI and purified with QIAQUICK plate kit (Qiagen, Venlo, The Netherlands). One hundred nanograms of the corresponding previously linearized heavy chain or light chain vectors was annealed to 10 ng of the PCR fragment with an IN-FUSION reaction (IN-FUSION Dry-Down Cloning Kit, Clontech, Mountain View, Calif.). The reaction mixture was transformed to XL2 Blue MRF' competent cells and plated overnight on agar plates containing 50 µg/mL kanamycin. Light chain constructs were digested with HindIII+NotI and heavy chain constructs were digested with AspI+HindIII to check structure by restriction analysis. The DNA sequences for all the clones were confirmed by sequence analysis.

Sequencing confirmed constructs of light chain and heavy chain DNA were transfected in 293 FREESTYLE cells (Invitrogen, Carlsbad, Calif.). The 293 FREESTYLE cells were transfected using 293 Transfectin (Invitrogen, Carlsbad, Calif.). EBNA monolayer cells were transfected using polyethylenimine-based transfection reagents. Transfected cells were incubated at 37° C./5% $CO_2$ for seven days in OPTI-MEM serum-free medium (Invitrogen, Carlsbad, Calif.). The medium was collected, centrifuged, filtered through 0.22 µm filtration system (Millipore, Billerica, Mass.), and then concentrated by a CENTRICON centrifuge filter (Millipore, Billerica, Mass.). Concentrated medium was mixed 1:1 with binding buffer (Pierce, Thermo Fisher Scientific, Rockford, Ill.), and subsequently loaded onto a pre-equilibrated protein A/G column (Pierce, Thermo Fisher Scientific, Rockford, Ill.) or HI-TRAP rProtein A FF (GE Healthcare, Waukesha, Wis.). The loaded column was washed with binding buffer and eluted with elution buffer (Pierce, Thermo Fisher Scientific, Rockford, Ill.). Eluted antibody was neutralized immediately and dialyzed against PBS buffer for overnight. Dialyzed antibody was concentrated with an AMICON centrifuge filter (Pierce, Thermo Fisher Scientific, Rockford, Ill.) and protein concentration was determined at OD280 nm with the extinct coefficient of 1.34 mg/mL. Purified antibody was analyzed using SDS-PAGE (Invitrogen, Carlsbad, Calif.), or protein LABCHIP (Caliper LifeSciences, Hopkinton, Mass.). SDS-PAGE was run under non-reducing conditions.

Example 6

Characterization of Affinity Matured 3B3 Antibodies

ELISA.
The selected anti-ADDL antibodies, i.e., those derived from the parental antibody, h3B3, where first assessed in a three-pronged Aβ ELISA to evaluate binding of the antibody to monomer Aβ, ADDLs, and fibrillar A. Polyclonal anti- ADDLs IgG (M90/1; Bethyl Laboratories, Inc., Montgomery, Tex.) was plated at 0.25 mg/well on IMMULON 3 REMOVAWELL strips (Dynatech Labs, Chantilly, Va.) for 2 hours at room temperature and the wells blocked with 2% BSA in TBS. Samples (monomeric Aβ, ADDLs, or fibrillar Aβ) diluted with 1% BSA in F12 were added to the wells, allowed to bind for 2 hours at 4° C., and washed 3× with BSA/TBS at room temperature. Monoclonal antibodies diluted in BSA/TBS were incubated for 90 minutes at room temperature and detected with a VECTASTAIN® ABC kit to mouse IgG. The HRP label was visualized with BIO-RAD peroxidase substrate and read at 405 nm on a Dynex MRX-TC microplate reader.

As shown in FIG. 1, with the exception of antibody 9.2, all of the anti-ADDL antibodies showed preferential binding to ADDLs relative to h3B3, selective (Comp 1 and 3: bind only ADDLs), non-selective (Comp 2: bind all forms of Aβ evaluated) comparators, and a control (no antibody). Antibody 9.2 showed low binding to all forms of Aβ, which suggested that its binding affinity was adversely affected during IgG conversion and/or antibody production. A summary of the ratio of ADDL:monomer and ADDL:fibrillar binding of the antibodies in this assay is presented in Table 6.

TABLE 6

| Antibody | ADDL:Monomer | ADDL:Fibrillar |
|---|---|---|
| h3B3 | 3.2 | 2.2 |
| 14.2 | 4.2 | 2.3 |
| 7.2 | 3.2 | 2.1 |
| 11.4 | 2.4 | 2.4 |
| 9.2 | 4.0 | 0.5 |
| 13.1 | 2.4 | 2.0 |
| 17.1 | 3.2 | 2.1 |
| 19.3 | 2.5 | 2.0 |

Cell-Based Binding Assay.

It has been shown that some anti-ADDL antibodies having preferential binding to ADDLs but cannot prevent ADDL binding to primary hippocampal neurons (Shughrue, et al. (2010) Neurobiol. Aging 31:189-202). In that preferential binding to ADDLs alone may not be an accurate predictor of effectiveness, it was desirable to identify anti-ADDL antibodies that also block ADDL binding to neurons, which was evaluated in a cell-based binding assay as follows. Anti-ADDL antibodies were mixed with 500 nM bADDLs, with the final antibody concentrations ranging from 1.8 nM to 450 nM. As a control, the same concentration of heat-denatured antibody (98° C. for minutes) was mixed with bADDLs. The antibody-bADDL mixtures were incubated in siliconized microcentrifuge tubes (Fischer Scientific, Pittsburgh, Pa.) at 37° C. for one hour with constant end-to-end rotation at a low speed. The mixtures were then applied to primary hippocampal and/or cortical cultures and incubated at 37° C. for one hour. The incubation was terminated by removing the culture medium. Cells were subjected to fixation and post-fixation treatments. Cells were then incubated with streptavidin conjugated with alkaline phosphate (Aβ) at 4° C. overnight, washed five times with PBS and reacted with the TROPIX CDP-Star chemiluminescent substrate (Life Technologies, Carlsbad, Calif.) at room temperature for 30 minutes. The bADDL binding intensity was measured and recorded with an ENVISION microplate reader (PerkinElmer, Waltham, Mass.).

The results of this study showed that the anti-ADDL antibodies herein, specifically antibody 19.3, dramatically reduced ADDL binding to neurons (FIG. 3). However, a marked reduction in antibody activity in this assay was observed when the antibodies were heat-denatured (FIG. 3).

In the same cell-based assay, it was determined whether excess Aβ monomer could reduce the ability of the 19.3 antibody to block ADDL binding to neurons. This analysis indicated that excess Aβ monomer did not reduce the in vitro efficacy of antibody 19.3. The $IC_{50}$ of antibody 19.3 alone was 15.4 nM, whereas the $IC_{50}$ of antibody 19.3 in the presence of excess monomer was 15.3 nM.

Determination of $EC_{50}$.

High protein binding plates (Costar, Corning, Lowell, Mass.), were coated with target ligand in PBS overnight at 4° C. The concentration of coating protein was 100 pmol/well for Aβ40 (American Peptide, Sunnyvale, Calif.) and 50 pmol/well for ADDLs. ADDLs were generated as described in Example 1. Next day, plates were washed five times with PBS+0.05% TWEEN-20 (Sigma Aldrich, St. Louis, Mo.) and blocked overnight with casein blocking buffer (Thermo Scientific, Waltham, Mass.) and 0.05% TWEEN-20. Three representative antibodies, 19.3 (FIG. 4A), 19.3S33 (FIG. 4B), and 19.3T33 (FIG. 4C), generated as described in Example 3, were tested at 15 µg/ml to 0 µg/ml in a 12-point three-fold dilution series. After 2 hours at room temperature incubation, the plates were washed and alkaline phosphatase conjugated anti-human IgG (ThermoScientific, Waltham, Mass.) was added at 0.08 µg/ml. After 45 minutes at room temperature incubation, the plates were washed and TROPIX® CDP®-Star chemiluminescent substrate (LIFE TECHNOLOGIES', Carlsbad, Calif.) was added. Luminescence was detected after 30 minutes on an ENVISION® microplate reader (PerkinElmer, Waltham, Mass.). Curve fits were completed using GRAPHPAD PRISM (GraphPad Software, Inc., San Diego, Calif.) software.

Example 7

Preparation of 19.3 Variants

An assessment of the amino acid sequence of the 19.3 antibody was conducted to identify potential sites of deamidation. Asparagine and aspartic acid residues present in the CDRs of therapeutic antibodies can undergo deamidation and isoaspartate formation (Valsak & Ionescu (2008) Curr. Pharm. Biotech. 9:468-481; Aswad, et al. (2000) J. Pharm. Biomed. Anal. 21:1129-1136), the formation of which can alter the binding potency of an antibody and, in turn, reduce antibody effectiveness for use as a therapeutic. Therefore, the asparagine residue at position 33 of the light chain CDR1 of antibody 19.3 was altered. Variants of the 19.3 antibody were produced (Table 7) with the substitution of serine, threonine or glutamic acid for the asparagine at position 33 in CDR1. The substitution of aspartic acid for the asparagine as position 33 was also generated as a control.

The mutagenesis of the asparagine at position 33 (N33) of the light chain CDR1 for the antibody 19.3 into N33S, N33T, N33E, or N33D was carried out by site-directed mutagenesis from the wild-type expression vector of pV1 JASN-GS-19.3-LCK using QUIKCHANGE II XL Site-Directed Mutagenesis Kit (Agilent Technologies, La Jolla, Calif.). The codon AAT for N was mutated to AGT for S in 19.3 N33S, ACT for T in 19.3 N33T, GAA for E in 19.3 N33E, or GAT for D in 19.3 N33D. Additional mutations at the asparagine at position 35 (N35) of CDR1 were also generated and combined with the N33S mutation (Table 7). Furthermore, mutations at the asparagine at position 58 in the CDR2 of antibody 19.3 were prepared (Table 8). All new codons in were confirmed by DNA sequence analysis. To generate full-length IgG antibodies for these variants, the respective light chain plasmids were paired with the cognate heavy chain plasmid, pV1JNSA-19.3-HCG2, for transient transfection in 293 FREESTYLE cells (Invitrogen, Carlsbad, Calif.). The expression and purification methods were described above.

Table 7 summarizes the amino acid sequence of CDR1 of the light chain of the variants compared to the CDR1 of the light chain for the parental antibody, 19.3. The present invention provides the variants of 19.3 whose light chain CDR1 is as set out in Table 7 below and whose CDR2 and CDR3 light chains and all heavy chains are as set for 19.3 itself.

TABLE 7

| Antibody | LC-CDR1 Sequence | SEQ ID NO: |
|---|---|---|
| 19.3 (parental) | RSSQSIVHSNGNTYLE | 41 |
| 19.3 N33S | RSSQSIVHSSGNTYLE | 42 |
| 19.3 N33T | RSSQSIVHSTGNTYLE | 43 |
| 19.3 N33A | RSSQSIVHSAGNTYLE | 44 |
| 19.3 N33E | RSSQSIVHSEGNTYLE | 45 |
| 19.3 N33D | RSSQSIVHSDGNTYLE | 46 |
| 19.3 N33S-N35Q | RSSQSIVHSSGQTYLE | 47 |
| 19.3 N33S-N35S | RSSQSIVHSSGSTYLE | 48 |
| 19.3 N33S-N35T | RSSQSIVHSSGTTYLE | 49 |
| 19.3 N33S-N35A | RSSQSIVHSSGATYLE | 50 |

Table 8 summarizes the amino acid sequence of CDR2 of the light chain of the variants compared to the CDR2 of the light chain for the parental antibody, 19.3. The present invention provides the variants of 19.3 whose light chain CDR2 is as set out in Table 8 below and whose CDR1 and CDR3 light chains and all heavy chains are as set for 19.3 itself.

TABLE 8

| Antibody | LC-CDR2 Sequence | SEQ ID NO: |
|---|---|---|
| 19.3 (parental) | KASNRFS | 51 |
| 19.3 N58Q | KASQRFS | 52 |
| 19.3 N58S | KASSRFS | 53 |
| 19.3 N58T | KASTRFS | 54 |
| 19.3 N58A | KASARFS | 55 |

The 19.3 variants were subsequently evaluated to determine whether the mutations had any effect on the stability of the antibody. Aliquots of purified variant antibodies, along with the 19.3 parental antibody, were incubated under various conditions at 4° C., 25° C. or 40° C. for a month before being subjected to ELISA analysis. High protein binding plates (Costar, Corning, Lowell, Mass.), were coated with target ligand in PBS overnight at 4° C. The concentration of coating protein was 50 pmol/well for ADDLs. ADDLs were generated as described in Example 1. One the next day, plates were washed five times with PBS+0.05% TWEEN 20 (Sigma Aldrich, St. Louis, Mo.) and blocked overnight with casein blocking buffer (Thermo Scientific, Waltham, Mass.) and 0.05% TWEEN 20. Three representative antibodies, 19.3, 19.3 N33S, and 19.3 N33T were tested at 15 μg/ml to 0 μg/ml in a 12-point three-fold dilution series. After 2 hours at room temperature incubation, the plates were washed and alkaline phosphatase-conjugated anti-human IgG (ThermoScientific, Waltham, Mass.) was added at 0.08 μg/ml. After 45 minutes at room temperature incubation, the plates were washed and TROPIX CDP-Star chemiluminescent substrate (LIFE TECHNOLOGIES, Carlsbad, Calif.) was added. Luminescence was detected after 30 minutes on an ENVISION microplate reader (PerkinElmer, Waltham, Mass.). Curve fits were completed using GRAPHPAD PRISM software (GraphPad Software, Inc., San Diego, Calif.).

As shown in FIGS. 4B and 4C, antibodies 19.3 N33S and 19.3 N33T had enhanced binding stability compared to the 19.3 parent (WT, FIG. 4A) following a one-month incubation at varying temperatures. A summary of the $EC_{50}$s of these antibodies at the various incubation temperatures is provided in Table 9.

TABLE 9

| | | Antibody $EC_{50}$ (nM) | | |
|---|---|---|---|---|
| Antigen | Incubation | 19.3 | 19.3 N33T | 19.3 N33S |
| bADDL | 0 timepoint | 1.1 | 15.5 | 7.8 |
| | 4°, 1 month | 1.7 | 11.6 | 8.6 |
| | 25°, 1 month | 2.1 | 15.7 | 12.8 |
| | 40°, 1 month | 5.9 | 23.5 | 10.1 |
| Aβ1-40 | 0 timepoint | 10.1 | 332.1 | 55.1 |
| | 4°, 1 month | 16.3 | 306.8 | 59.1 |
| | 25°, 1 month | 22.1 | ND | 24.3 |
| | 40°, 1 month | 88.8 | 96.3 | 29.9 |

$EC_{50}$s of several of the 19.3 variants were determined and it was found that the variants maintained specificity for ADDLs in an ELISA assay (Table 10)

TABLE 10

| | $EC_{50}$ (nM) | |
|---|---|---|
| Antibody | ADDL | Aβ1-42 |
| 19.3 | 0.8 | 18 |
| 19.3 N33S | 1.7 | 150 |
| 19.3 N33T | 3.1 | 244 |
| 19.3 N33D | 0.82 | 28 |

All antibodies were IgG2.

Example 8

In Vitro FcRn Binding of Anti-ADDL Antibodies

To characterize the ability of anti-ADDL antibodies to bind and to dissociate immobilized human FcRn, the seven h3B3 variant anti-ADDL antibodies were evaluated in a BIACORE FcRn binding assay, a surrogate system used to evaluate antibody PK and predict the terminal half life ($t_{1/2}$) of antibodies in non-human primates. Briefly, purified human FcRn protein was immobilized onto a BIACORE CM5 biosensor chip and PBSP (50 mM $NaPO_4$, 150 mM NaCl and 0.05% (v/v) TWEEN 20) pH 7.3 was used as running buffer. The monoclonal antibodies were diluted with PBSP, pH 6.0, to 100 nM, allowed to bind FcRn for 3 minutes to reach equilibrium and dissociated in pH 7.3 running buffer. A report point (Stability) was inserted at 5 seconds at the end of monoclonal antibody binding and the "% bound" was calculated as $RU_{stability}/RU_{binding}$ (%). This analysis indicated that monoclonal antibodies (mAbs) with identical Fc sequences but different Fab domains can bind and dissociate from FcRn with considerable differences. Moreover, an apparent correlation between dissociation at neutral pH and in vivo pharmacokinetics was observed, in which mAbs with slow-dissociation fractions (i.e., higher "% bound") tended to exhibit shorter $t_{1/2}$ in vivo. This feature was used as an in vitro screening tool for antibody pharmacokinetics.

h3B3 variant anti-ADDL antibodies, along with h3B3, two ADDL preferring antibodies (Comp 1 and 3) and a non-selective (Comp 2: binds all Aβ forms evaluated) comparator in the FcRn binding assay. A sensorgram was generated (FIG. 5) showing the initial binding of the antibody at pH 6.0 and then the dissociation of the antibody at pH 7.3 from 180 seconds. As shown in FIG. 5, there was a noticeable difference between h3B3 and the other antibodies assessed. While h3B3 had a high percent bound to FcRn, the seven anti-ADDL antibodies of the present invention, as well as the two comparator antibodies exhibited considerably lower binding.

Example 9

Binding Affinity of Anti-ADDL Antibody 19.3

Affinity matured antibody 19.3 was selected for further characterization. The complete DNA sequence and the deduced amino acid sequence for the variable region of the light chain was determined, SEQ ID NOs:14 and 15, respectively. Alignment of the heavy (SEQ ID NO:17) and light (SEQ ID NO:15) chain variable regions is shown in FIG. 6, together with the closest germ line sequence (SEQ ID NO:47).

BIACORE™ (GE Healthcare, Waukesha, Wis.) and KINEXA (Sapidyne, Boise, Id.) analyses were carried out to ascertain the binding affinity of anti-ADDL antibody 19.3 for ADDLs and determine the selectivity of 19.3 for ADDLs versus monomer Aβ. BIACORE™ and KINEXA-based technologies are widely used for the measurement of binding affinity between macromolecules such as antibody and protein target.

BIACORE™.

In the Surface Plasmon Resonance (SPR) technology on which BIACORE™ is based, quantitative measurements of the binding interaction between one or more molecules are dependent on the immobilization of a target molecule to the sensor chip surface. Binding partners to the target can be captured as they pass over the chip. SPR detects changes in mass in the aqueous layer close to the sensor chip surface by measuring changes in refractive index. When molecules in the test solution bind to a target molecule, the mass increases ($k_a$), when they dissociate the mass falls ($k_d$). This simple principle forms the basis of the sensorgram, i.e., a continuous, real-time monitoring of the association and dissociation of the interacting molecules. The sensorgram provides quantitative information in real-time on specificity of binding, active concentration of molecule in a sample, kinetics and affinity.

KINEXA.

The KINEXA technology (Sapidyne Instruments, Boise, Id.) measures binding constants to characterize biomolecular binding events in the solution phase, not binding events between a solution phase and a solid phase. In solution, the binding partners reach equilibrium after sufficient incubation. The unbound molecules are quantified with a titration, which reflects the portion of molecules bound to the partners. The KINEXA method does not require modification of molecules under study. With KINEXA, the reaction being measured occurs between unmodified molecules in solution. Therefore, concerns of how modification alters "native" binding reactions are eliminated. The KINEXA method allows a wider range of binding constants as tight as $10^{-13}$ M. The KINEXA software performs data analyses, which are based on exact solutions to classic binding equations ($K^d$ mathematics), not pseudo first-order approximations. KINEXA does not require arbitrary data manipulations or range selections.

As shown in Table 11, antibody 19.3 had a 4.8 nM affinity for ADDLs as compared to a 150 nM affinity for monomer Aβ in the BIACORE™ assay. The thirty-fold selectivity of antibody 19.3 for ADDLs over Aβ monomer was markedly better than that seen for the parental antibody, h3B3, which exhibited only a 10-fold preference for ADDLs versus Aβ monomer.

TABLE 11

| Antibody | ADDLs (nM) | Aβ1-40 (nM) | Ratio (Aβ monomer/ADDL) |
|---|---|---|---|
| 3B3 | 10.0 | 104.6 | 10 |
| 19.3 | 4.8 | 150.0 | 31 |

Similarly, antibody 19.3 was evaluated in a KINEXA-based equilibrium constant measurement. As shown in Table 12, antibody 19.3 had an equilibrium constant of 2.7 nM, which represents more than a six-fold preference for ADDL oligomers versus Aβ40 monomer binding in the same assay.

TABLE 12

| Antibody | ADDLs (nM) | Aβ1-40 (nM) | Ratio (Aβ monomer/ADDL) |
|---|---|---|---|
| 3B3 | 3.3 | 45.0 | 13.6 |
| 19.3 | 2.7 | 16.7 | 6.2 |

$EC_{50}$ of 19.3 for Aβ Oligomers and Aβ1-40 in One-Sided ELISA Assay.

Figure 7A:
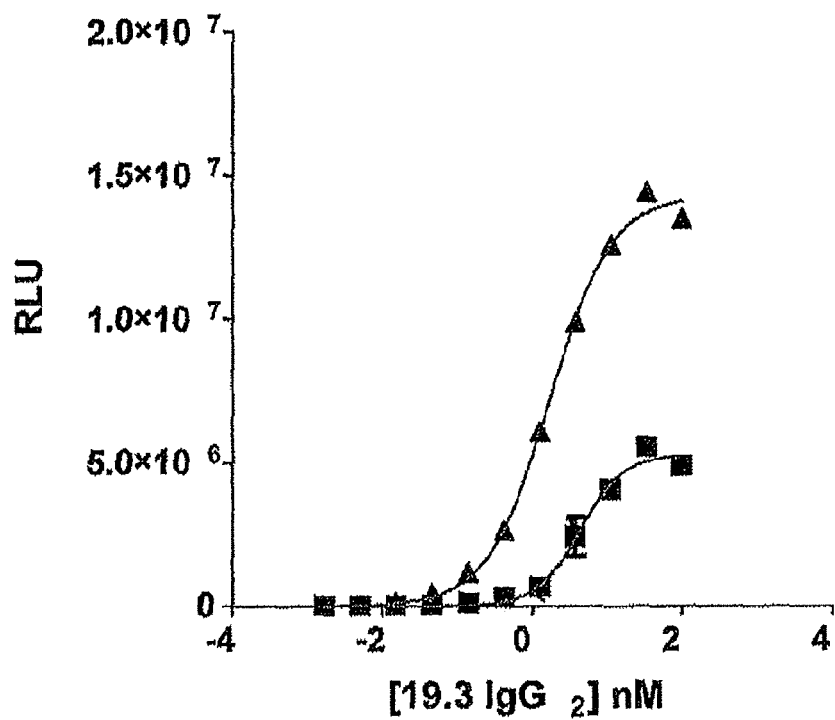
FIG. 7A shows a one-sided ELISA with plates coated with either Aβ oligomer (triangles) or Aβ monomer (squares), demonstrating the relative affinities and maximum binding characteristics of the humanized antibody 19.3.

$EC_{50}$ represents the half-maximal total Aβ oligomer binding. High protein binding plates were coated at either 100 pmol/well Aβ1-40 or 50 pmol/well Aβ oligomers in PBS, overnight at 4° C. Next day, plates were washed five times with PBS+0.05% TWEEN 20 and blocked overnight with casein blocking buffer (Thermo Scientific, Waltham, Mass.) and 0.05% TWEEN 20. The 19.3 antibody was tested at 0 to 15 µg/ml in a 12-point three-fold dilution series. After two hours at room temperature incubation, the plates were washed and alkaline phosphatase-conjugated anti-human IgG (ThermoScientific, Waltham, Mass.) was added at 0.08 µg/ml. After incubation for 45 minutes at room temperature, the plates were washed and TROPIX CDP star (Applied Biosystems, Foster City, Calif.) was added. Luminescence was detected after minutes on an ENVISION plate reader (PerkinElmer, Waltham, Mass.). Curve fits were completed using GraphPad Prism (GraphPad Software, Inc., San Diego, Calif.) software. This analysis indicated that the 19.3 antibody (IgG2 isotype) has an $EC_{50}$ of approximately 1.7 nM and 4.3 nM for Aβ oligomers and Aβ1-40 monomer, respectively, in the one-sided ELISA assay (FIG. 7A). In this format the 19.3 antibody demonstrated approximately three-fold greater maximum binding for Aβ oligomers as compared to Aβ40 monomer, while the potency was approximately 3.7-fold greater.

Competitive Binding Assays with Aβ Oligomers and Aβ Monomer.

In an ELISA assay that measures binding of antibody 19.3 to ADDLs and Aβ monomer captured on plates, $ED_{50}$ values for ADDLs and Aβ monomer were 1.7 nM and 4.3 nM, respectively. The numbers generated by the BIACORE and the plate-based ELISA assays represent an underestimation of the true affinity and selectivity of the 19.3 antibody, because the values are calculated based on the monomeric concentration of $A\beta_{1-42}$ in the ADDL preparations. ADDL preparations contain a mixture of soluble $A\beta$ oligomers of various sizes, ranging from dimers to 24-mers, and possibly larger aggregates, thus the epitope concentration of ADDLs is not known. Moreover, to more accurately represent an in vivo CSF sample, where both $A\beta$ oligomers and $A\beta$ monomers would be present, the affinity of 19.3 for $A\beta$ oligomers in the presence of $A\beta1$-40 monomer was tested in a competitive ELISA format.

The ELISA plate was prepared by first coating with a preparation of $A\beta$ oligomers at 50 pmol per well and then adding the 19.3 antibody at a final concentration of 2 nM to each well. This concentration of 19.3, i.e., 2 nM, represents the $EC_{50}$ concentration for $A\beta$ oligomers binding determined in the one-sided ELISA (FIG. 7A). Adding $A\beta1$-monomer in a titration curve to competitively remove 19.3 from the $A\beta$ oligomer-coated surface resulted in an $EC_{50}$ of 5.5 µM. $A\beta1$-40 monomer-coated plates were prepared in the same way, using 100 pmol/well. The 19.3 antibody was applied at 4 nM to each well in the casein blocking buffer matrix and allowed to interact with $A\beta$ oligomers or $A\beta1$-40 for 30 minutes at room temperature with shaking. A 12-point, three-fold concentration curve starting at 10 µM, for either $A\beta$ oligomers or $A\beta1$-40, was applied to the antibody containing wells. For plates coated with $A\beta$ oligomers, $A\beta1$-40 was added to the wells; for $A\beta1$-40 plates, $A\beta$ oligomers were added to the wells. The plates were incubated for one and half hours at room temperature. Both detection of residual antibody binding and the $EC_{50}$ calculations were determined as in the one-sided ELISA assay.

Figure 7B:
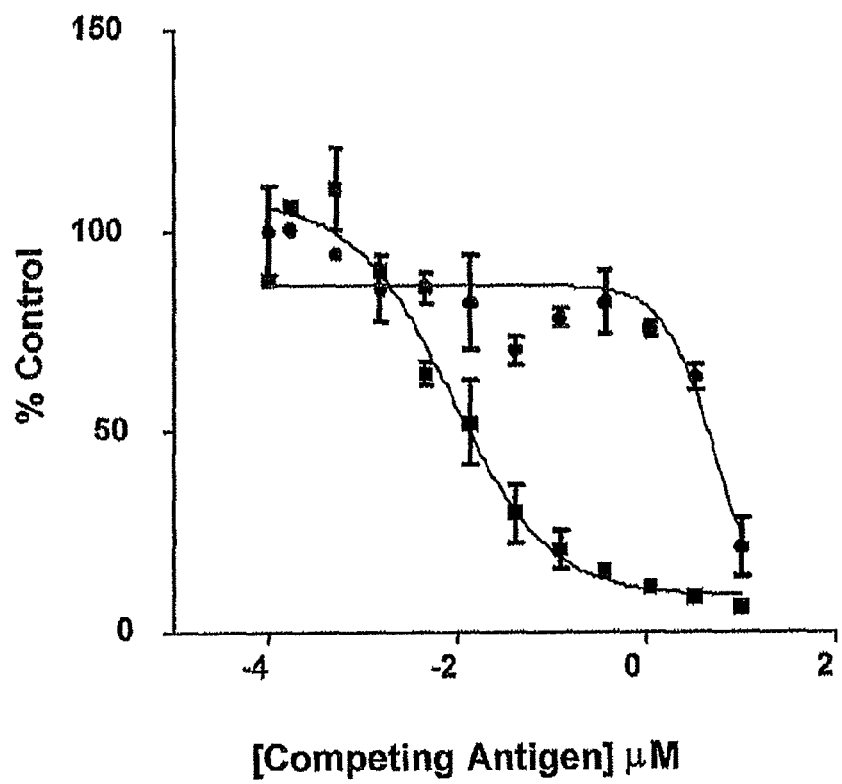
FIG. 7B shows a competitive ELISA and the relative affinities of 19.3 for Aβ oligomers (triangles) and Aβ monomer (squares) coated on an ELISA plate in the presence of the competing species in solution.

This analysis indicated that adding $A\beta1$-40 monomer in a titration curve to competitively remove 19.3 from $A\beta$ oligomer-coated surface resulted in an $EC_{50}$ of 5.5 µM (FIG. 7B). When 100 pmol per well of $A\beta1$-40 monomer was used to coat the ELISA plate and $A\beta$ oligomers were used to compete for antibody binding, the $EC_{50}$ was 8.7 nM. This indicated that 19.3 had an affinity for $A\beta1$-42 oligomers compared to $A\beta1$-40 monomers of ~630:1 in a competitive binding assay. Alternatively stated, the concentration of $A\beta1$-40 required to displace 50% of 19.3 from $A\beta$ oligomers was approximately 600-fold higher than the concentration of $A\beta$ oligomers required to displace 19.3 binding to $A\beta1$-40. Concentrations up to 0.2 µM of $A\beta$ oligomers have been reported in CSF from AD patients (Georganopoulou, et al. (2005) *Proc. Natl. Acad. Sci. USA* 102:2273-2276) as compared to 1500 pM of $A\beta$ monomer. Thus, the sensitivity and selectivity of 19.3 for $A\beta$ oligomers indicates the use of this antibody in the treatment of a disease mediated by the effects of soluble, oligomers of $A\beta1$-42.

To determine the calculated affinity of antibody 19.3 for monomer $A\beta1$-40 versus soluble oligomers of $A\beta1$-42, the average molecular weight of ADDLs was taken into consideration (Hepler, et al. (2006) *Biochemistry* 45:15157-15167). With a measured $EC_{50}$ for ADDLs of 9 nM, antibody 19.3 exhibits approximately a 600-fold selectivity for ADDLs as compared to monomeric $A\beta1$-40. When including the molecular weight of ADDLs (175 kDa), as compared to the molecular weight of monomeric $A\beta1$-42 (4.5 kDa), the $IC_{50}$ value of antibody 19.3 for ADDLs was calculated to be 0.28 nM, with a selectivity versus monomer of >17,000.

ALPHALISA Assay.

The ALPHALISA technology (PerkinElmer) is a bead-based immunoassay designed for the detection of analytes in biological samples. This chemiluminescent assay exhibits remarkable sensitivity, wide dynamic range and robust performance that compares advantageously with conventional ELISA. The selectivity and sensitivity the 19.3 antibody for ADDLs versus monomeric $A\beta$ ($A\beta1$-40) in the ALPHALISA assay was determined. This analysis indicated that a signal at 0.2 pM of ADDLs was greater than a signal at 1000 pM of $A\beta1$-40, indicating an ADDL versus monomeric $A\beta$ selectivity of approximately 5000 in this assay.

Oligomer Selectively.

Synthetic ADDLs or ADDLs extracted from Tg2576 mouse brains were prepared and cross-linked using the photo-induced cross-linking of unmodified proteins (PICUP) method (Bitan & Teplow (2004) *Acc. Chem. Res.* 37:357-64). Antibody 19.3 was added and antibody:ADDL complexes were cross-linked with an amine-reactive crosslinker (CovalX technology; Bich & Zenobi (2009) *Curr. Opin. Struct. Biol.* 19:632-39) and then separated by size exclusion chromatography (SEC). The cross-linked complexes of antibody 19.3 with ADDLs where detected with an ELISA using a second anti-$A\beta$ antibody, 82E1, and an anti-human kappa antibody. 19.3:ADDL complexes eluted at retention times corresponding to soluble $A\beta$ oligomers; monomeric $A\beta$ eluted in later eluting fractions. Wild-type mouse brain extracts showed no signal. These results showed that antibody 19.3 binds synthetic and endogenous ADDLs, and that synthetic and endogenous ADDLs have a similar size distribution. This analysis indicated that antibody 19.3 had an affinity for a spectrum of soluble $A\beta$ oligomer species separated by SEC from $A\beta$ monomers.

Binding of Antibody 19.3 to $\beta$-Amyloid in Brain Tissue.

To assess whether antibody 19.3 binds to $\beta$-amyloid plaque deposits, 8-9 month old female Tg2576 transgenic mice, with existing $\beta$-amyloid aggregates in the brain were injected IV with 2, 20, or 50 mg/kg of the antibody and brain sections were collected and evaluated microscopically. Co-localization studies with the amyloid marker Thioflavin-S showed no preferential staining of $\beta$-amyloid. The results of this analysis showed that antibody 19.3 was present in the brain and typically did not co-localize with plaques in Tg2576 brain at 24 hours after a mg/kg IV dose. However, there was occasional co-localization of antibody 19.3 with fibrillic plaques. These results indicate that antibody 19.3 has very low, non-selective affinity for fibrillar $A\beta$-species. In addition, in all of these studies there was no evidence of antibody 19.3-mediated plaque dissolution or microhemorrhage.

The ability of antibody 19.3 to bind to vascular $\beta$-amyloid plaque deposits was assessed in the same study. The results of this analysis indicated that there was no 19.3 antibody staining of blood vessels or of $\beta$-amyloid associated with blood vessels. Therefore, there is a reduced potential for vasogenic edema using the antibody of this invention in the treatment of subjects with AD.

Example 10

Biophysical Characterization of Anti-ADDL Antibody 19.3

Biophysical characterization to assess the potential for antibody aggregate formation was carried out to show that the anti-ADDL antibodies herein are stable under stressed conditions and suitable for use as a therapeutic. Anti-ADDL antibody 19.3 was concentrated to >50 mg/mL and placed in a number of formulations with a pH ranging from 5.0 to 8.0. Two sets of samples were incubated at 37° C. and 45° C. for one week. A third set of samples was placed at −70° C. to initiate a series of five freeze/thaw cycles. Size exclusion chromatography analysis indicated that the antibody preparations were predominantly (>95%) in the monomer state, with small amount of dimers, which were typical for monoclonal antibody preparations, The amount of dimers and higher molecular weight oligomers did not increase after the temperature stress across all buffers and no fragmentation was observed. As summarized in Table 13, the near ultraviolet turbidity analysis also indicated lack of aggregation.

TABLE 13

| Antibody | Initial Aggregation (%) | Initial Fragments (%) |
|---|---|---|
| 19.3 | 2.2 | 0.0 |
| Control 1 | 1.6 | 0.4 |
| Control 2 | 2.6 | 0.0 |

The freeze/thaw stressed samples showed buffer-dependent increase in turbidity, which was comparable to other monoclonal antibodies. Viscosity at 50 mg/mL was below 2 centipoise, indicating an acceptable injection viscosity, as the 20 centipoise level is generally considered to be a practical limit for subcutaneous injections. Differential scanning calorimetry also revealed acceptable thermal stability, with Fab unfolding at about 72° C. and the least stable CH2 domain unfolding above 65° C. Taken together, antibody 19.3 demonstrated very good structural stability with biophysical properties compatible with subcutaneous delivery.

Example 11

Aβ Oligomers in Human CSF and Brain

Data provided in a number of publications (Mayeux, et al. (2003) *Neurology* 61:1185-1190; Mechta, et al. (2000) *Arch. Neurol.* 57:100-105; Fukumoto, et al. (2010) *FASEB J.* 24:2716-2726; Karran, et al. (2011) *Nature* 10:698-712; Delacourte, et al. (2002) *Neurology* 59:398-407) were analyzed to determine the level of various species of Aβ that are present in the brain and CSF of AD and healthy subjects. This analysis (Table 14) indicated that soluble oligomeric Aβ are the least prevalent species of Aβ in the brain and CSF of subjects with AD.

TABLE 14

| Aβ Species | AD | Non-AD |
|---|---|---|
| Aβ40 Plaque in brain | 7.80E+07 pg/g brain tissue | 1.00E+05 pg/g brain tissue |
| Aβ42 Plaque in brain | 3.44E+08 pg/g brain tissue | 7.10E+06 pg/g brain tissue |
| CSF Aβ40 monomer | 6.04E+03 pg/mL CSF | 6.39E+03 pg/mL CSF |
| CSF Aβ42 monomer | 2.38E+02 pg/mL CSF | 4.03E+02 pg/mL CSF |
| CSF Aβ oligomer | 2.20E+00 pg/mL CSF | 3.00E-01 pg/mL CSF |

Figure 8A:
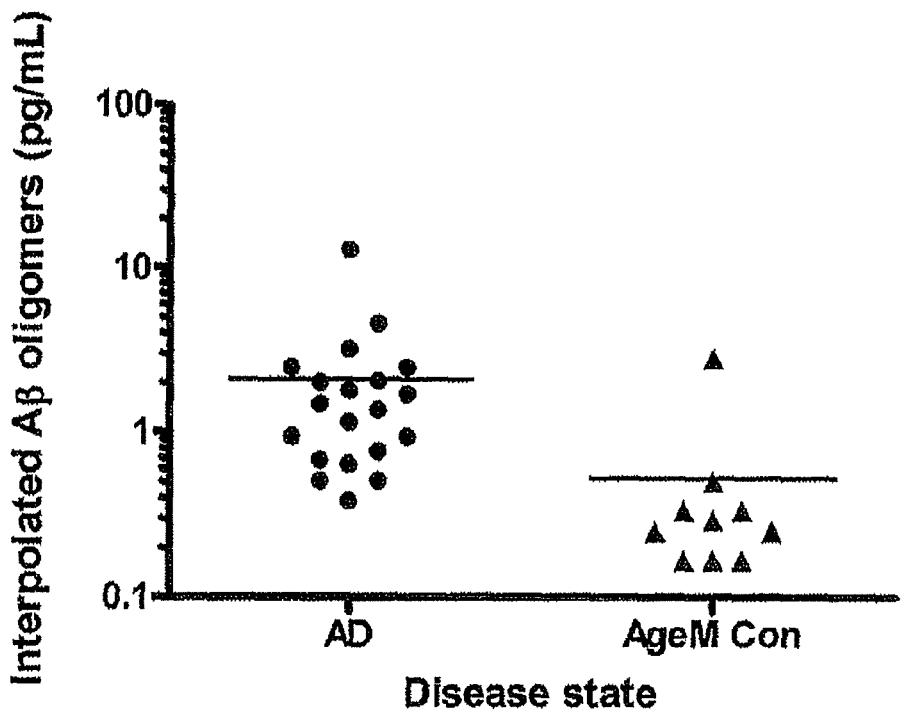
FIGS. 8A and 8B are graphic representations of the levels of Aβ oligomers detected in human cerebrospinal fluid (CSF) samples.
Figure 8B:
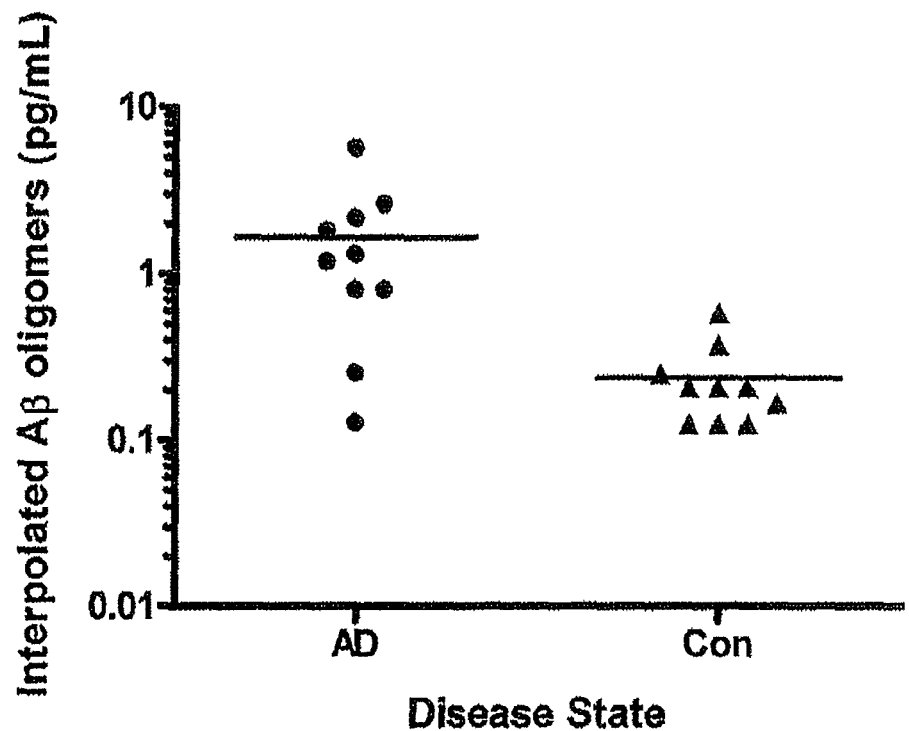
Figure 9A:
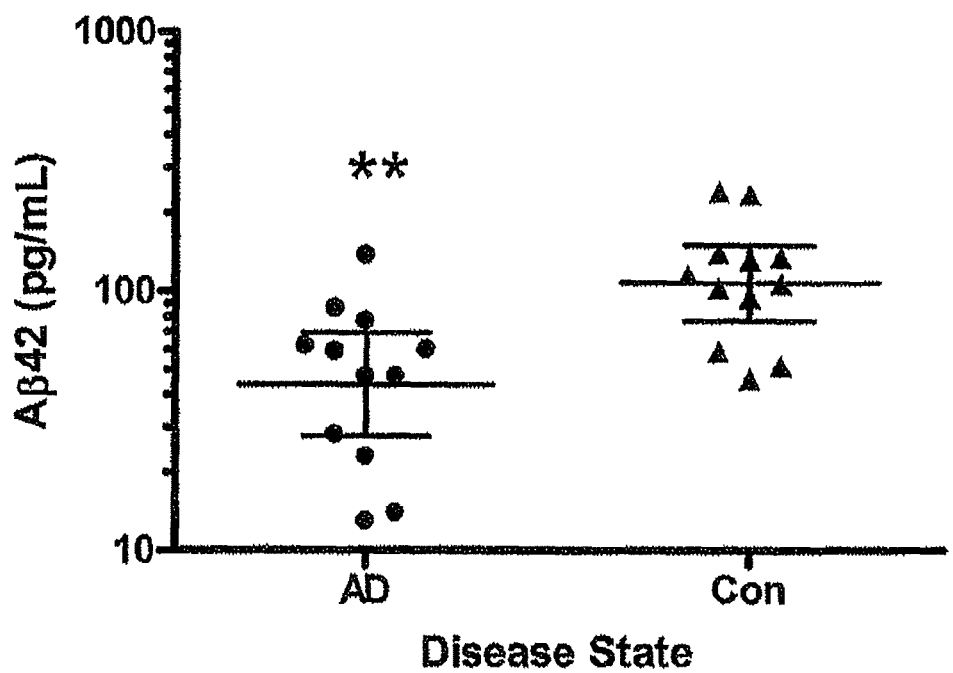
FIGS. 9A and 9B are graphic representations of Aβ monomer levels in the CSF of either clinically confirmed AD or young control, i.e., non-AD, patients, with a corresponding decrease in the levels of Aβ1-42 monomer and unchanged levels of Aβ1-40 monomer in the AD samples. This is representative of the general pattern observed for AD patients and confirmed the disease state of the samples evaluated in FIG. 8B.
Figure 9B:
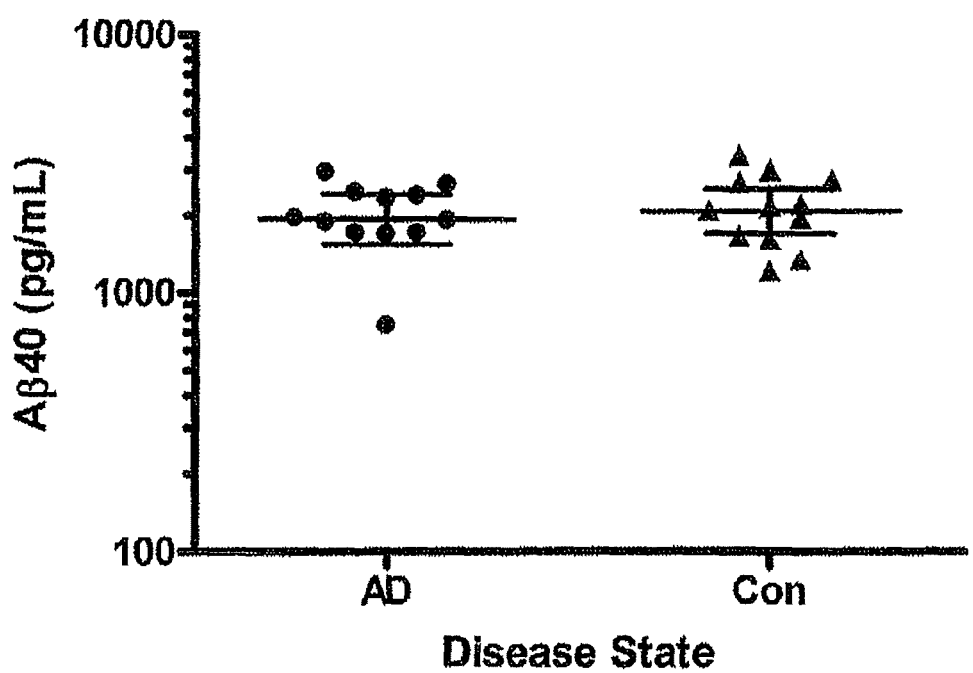

A combination of antibody 19.3 and 82E1 (Immunobiological Laboratories (IBL), Inc., Minneapolis, Minn.) were used in an Aβ oligomer-selective sandwich ELISA to further determine endogenous levels of Aβ oligomers in human CSF samples (FIGS. 8A and 8B). In two separate sample cohorts, the fluorescent signal, generated by the presence of Aβ oligomers, was significantly elevated in AD (clinically diagnosed using a MMSE score below 25 as probable AD) CSF as compared to either young or healthy age matched controls. The absolute levels of Aβ oligomers observed were 2.1±0.61 pg/mL in AD (n=20) and 0.53±0.26 pg/mL in age-matched control (n=10) in CSF samples from Precision Medicine (Solana Beach, Calif.) with a t-test, two way Mann-Whitney score of p<0.0004 (FIG. 8A). The absolute levels of Aβ oligomers observed were 1.66±0.5 pg/mL in AD (n=10) and 0.24±0.05 pg/mL in control (n=10) in CSF samples from Bioreclamation (Hicksville, N.Y.), with a t-test, two way Mann-Whitney score of p<0.0021 (FIG. 8B). Combining the two cohorts, 90% of the diagnosed AD CSF samples were above the LLoRQ of 0.42 pg/mL, while only 20% of the age-matched control or 10% of the young controls were above this limit. All values were above the LoD of 0.04 pg/mL. Aβ40 and Aβ42 monomer levels were measured in the CSF samples obtained from Bioreclamation (FIGS. 9A and 9B, respectively) and were comparable between the AD and control CSF for Aβ1-40 (FIG. 9A), while they were significantly reduced in the AD samples for Aβ1-42 (FIG. 9B). This has been previously reported as a feature of AD CSF (De Meyer, et al. (2010) *Arch. Neurol.* 67:949-956; Jack, et al. (2010) *Lancet Neurol.* 9:119-128) and confirmed the correct diagnosis of these samples. Without wishing to be bound to any theory, it is believed that the lower levels of Aβ1-42 in the AD CSF samples is due to retention of Aβ1-42 in the amyloid deposits of the AD brain.

Given the specifically and selectively of the antibodies of this invention for soluble oligomeric Aβ, the instant antibodies can provide a therapeutic benefit at relatively low doses because once the anti-ADDL antibody of the invention reaches the brain it will not be diluted by the more abundant species of Aβ (Table 14). Not wishing to be bound by theory, it is believed that the lack of efficacy of other anti-Aβ immunotherapies may be attributed to their lack of specificity. In particular, given that these other antibodies bind to the highly abundant Aβ monomer and/or Aβ plaque species (Table 15), an efficacious dose will likely be difficult to attain.

TABLE 15

| mAb | Aβ Monomer | Aβ Oligomers | Aβ Plaque |
|---|---|---|---|
| 19.3 | − | +++ | + |
| mAb158[1] | − | +++ | ++ |
| BiiB037[2] | − | − | +++ |
| Gantenerumab[3] | + | ++ | +++ |
| Crenezumab[4] | ++ | +++ | ++ |
| Bapineuzumab[5] | +++ | +++ | +++ |
| Ponezumab[6] | +++ | − | +++ |
| Solanezumab[7] | +++ | ++ | − |

−, no detectable affinity;
+, low affinity;
++, medium affinity;
+++, high affinity.
[1]Lord, et al. (2009) *Neurobiol. Dis.* 36: 425-34).
[2]Dunstan, et al. (2011) *Alz. Dement.* 7: S457 and S700.
[3]Bohrmann, et al. (2012) *J. Alzheimers Dis.* 28: 49-69.
[4]US 2010/0098707.
[5]Bonda, et al. (2010) *Curr. Opin. Drug Discov. Devel.* 13: 235-246; Salloway, et al. (2012) Verbal presentation, *Annual Meeting European Federation of Neurological Societies*, Stockholm, Sweden.
[6]Freeman, et al. (2012) *J. Alzheimers Dis.* 28: 531-41.
[7]Farlow, et al. (2012) *Alzheimers Dement.* 8: 261-71; Doody (2012) Verbal presentation, *American Neurological Association Annual Conference*, Boston.

Example 12

Pharmacokinetic Analysis of 19.3 and Efficacy in a Model of AD

Pharmacokinetics Study in Human FcRn Mice.

Human FcRn mice (heterozygous Tg2576) (Jackson Laboratories, Bar Harbor, Me.) have been shown to be a valuable surrogate system for evaluating monoclonal antibody pharmacokinetics. To characterize the pharmacokinetics of the anti-ADDL antibody 19.3 in human FcRn mice, three animals received a single intravenous injection of antibody 19.3 at 10 mg/kg via tail vein. A series of 10 blood samples were then collected at time points 0, 25, 50, 75, 100, 150, 250 and 350 hours after IV administration of antibody 19.3 or h3B3 and a validated anti-human IgG immunoassay was used to determine blood levels of antibody. As shown in FIG. 10, blood levels for antibody 19.3 declined in a biphasic manner with an apparent $t_{1/2}$ 77±6 hours, which was considerably longer than the half-life for the parental antibody, h3B3, of about 29±9 hours. These half lives were in agreement with the difference predicted by the in vitro FcRn binding assay (FIG. 5). The elimination phase terminal half-life was determined using non-compartmental model (WINNONLIN®, Pharsight, Sunnyvale, Calif.) and data points between day 3 and day 15 post-dose.

Pharmacokinetics of Antibody 19.3 in Rats.

Male rats were injected IV with 2, 10, or 50 mg/kg of the antibody 19.3. Plasma, CSF, and brain levels were measured 24 hours after the injection. There were linear, dose-dependent increases of antibody levels in all 3 compartments. CSF and brain levels were roughly, 0.1% and 0.03%, respectively, of the plasma concentration.

Pharmacokinetics of Antibody 19.3 in Dogs.

Two male beagle dogs were injected IV with 10 mg/kg of antibody 19.3. Serum, CSF, and brain levels were measured 48 hours after the injection. The injections produced significant concentrations of the antibody in the serum and measurable concentrations in CSF and brain of dogs (Table 16).

TABLE 16

| Sample | Antibody 19.3 (µg/ml) |
|---|---|
| Serum | 31200 |
| CSF | 45 |
| Brain | 6 |

CSF and brain levels were 0.15% and 0.02%, respectively, of serum concentrations at 48 hours.

Pharmacokinetics Study in Non-Human Primates.

Figure 11:
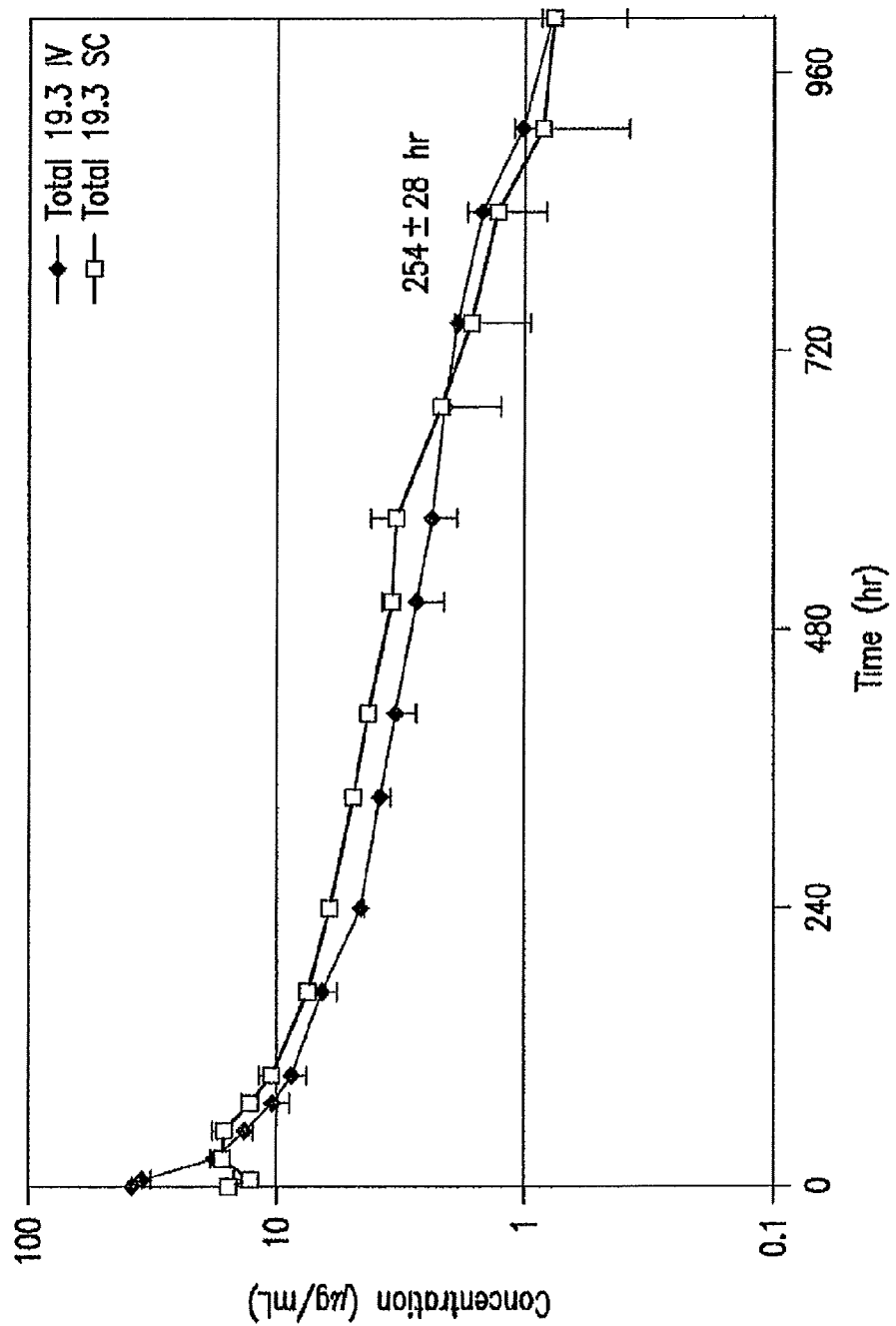
FIG. 11 is a graphical representation of the PK of anti-ADDL antibody 19.3 (in serum) assessed in six rhesus monkeys following administration of a bolus intravenous (IV) or subcutaneous (SC) dose of 5 mg/kg. A half-life ($t_{1/2}$) of 254±28 (274±9) hours was determined after IV administration and 204±49 (219±52) hours after SC dosing.

To confirm the predicted $t_{1/2}$ of 19.3 in primates, a primate pharmacokinetics study was conducted for anti-ADDL antibody 19.3 in a cohort of cisterna magna ported rhesus monkeys. Six animals (three male/three female) were dosed with a single intravenous bolus or subcutaneous injection of antibody 19.3 (5 mg/kg) and blood samples collected after antibody administration. Concurrently, CSF samples were collected from the cisterna magna port at 0, 2, 4, 8, 12, 24, 30, 48, 54 and 72 hours and the concentration of antibody 19.3 in the serum and CSF was determined with an anti-human IgG ELISA assay. When the animals were administered a single IV bolus injection of antibody 19.3, a $t_{1/2}$ of 254±28 hours was observed, while a $t_{1/2}$ of 204±49 hours was seen after subcutaneous administration (FIG. 11). In addition, it was observed that antibody 19.3 was able to cross into the primate CSF, where it increased in concentration during the first 48 hours and peaked at about 0.1% of the antibody dosed (FIG. 12).

In a second study, 20 mg/kg of the anti-ADDL antibody 19.3 was given IV to 6 male Rhesus monkeys on Study Day 1 and Day 7. Plasma and CSF were sampled at multiple time points after dosing. Dosing resulted in significant plasma concentrations of antibody. There were no significant differences in the values measured for the first and the second dosing. The values of the 2 doses were thus combined for the quantitative analysis. The terminal plasma half-life was measured at 10.8 days and the clearance at 0.75 mL/hr/kg. Antibody dosing resulted in measurable levels in the CSF of the animals with a similar time course as in the plasma CSF concentrations of the antibody were approximately 0.05% of the corresponding plasma levels.

In additional repeat-dose studies, 3 male and 3 female rhesus monkeys received three weekly doses of antibody 19.3 (100 mg/kg). Clinical and serological endpoints were measured after the last dose and after 28 day recovery period there were no deaths, physical indications, or changes in body weight or food consumption in any animals. Moreover, there were no relevant hematological findings. Therefore, the No Observed Adverse Effect Level (NOAEL) in Rhesus monkeys was up to 100 mg/kg. Telemetric measurements of cardiovascular, respiratory function and body temperature in conscious animals indicated that there was increased systolic and diastolic blood pressure and heart rate in 2 monkeys with a coinciding decreased uncorrected QT interval (≤−8%) and no effects on the HR-corrected QT interval (QTci interval). In addition, there was a slight increase in body temperature, but no effects on rate and depth of respiration.

Biodistribution of Antibody 19.3 in Rhesus Monkeys.

A specific study assessed the in vivo distribution of antibody 19.3 in comparison with antibody 3D6 (murine precursor of bapineuzumab) in Rhesus monkey using PET combined with computerized tomography (CT). Three male adult monkeys were used in the study. Antibodies 19.3 and 3D6 were radiolabeled with $^{64}Cu$. Blood and plasma counts were measured and whole body PET/CT scans were obtained at various time intervals over 48 hours. PET/CT imaging demonstrated no significant off-target binding uptake difference between antibodies for non-excretory organs/tissues. The highest signals were observed in the heart reflecting the blood pool. Liver and kidneys were considered excretion organs for labeled antibodies and smaller protein fragments. Inspection of the PET images revealed higher uptake in the sacral region for the 19.3 antibody at the 24- and 48-hour time points as compared to 3D6. The similar shape of the curve for both antibodies in liver did not point to off-target binding, but a difference in non-specific hepatic clearance rate between the two antibodies.

Distribution of $^{125}I$-Labeled Anti-ADDL Antibody 19.3 in Mouse Brain.

To determine the concentration of antibody that reached the brain, twelve-month-old male Tg2576 mice (line B6; SJL-TgN APPSWE) were injected (tail vein) with 200 µg of $^{125}I$-labeled 19.3 antibody (~8 mg/kg), or one of two comparator antibodies, and the blood and CSF collected two hours later. The residual radioactivity was cleared from the vessels of the brain via cardiac perfusion with PBS prior to the removal of the brain. A sample of blood, CSF and the whole brain was then placed in a gamma counter to determine the amount of radio-labeled antibody present in each sample. After counting, the brains were fixed in 4% paraformaldehyde for 48 hours and then processed for free-floating immunocytochemistry. The localization of antibody 19.3 in the mouse brain was detected with an anti-human secondary antibody and a standard ABC detection method. This immunoreactivity was then combined with thioflavin S staining (a stain that detects plaques) to determine the colocalization of antibody with plaques in the mouse brain.

Figure 13C:
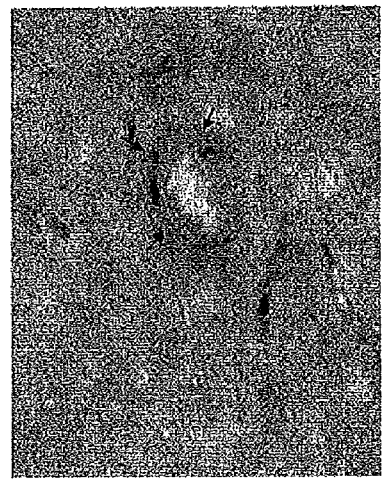

As shown in FIGS. 13A and 13B, radiolabeled antibody 19.3 was able to penetrate the blood-brain-barrier into the mouse CSF and brain. Moreover, the data indicated that antibody 19.3 was enriched in the brain (0.19%) when compared with levels seen in the CSF (0.02%). To determine if this concentration in the brain was due to the association of antibody 19.3 with Aβ, the brains were fixed and processed for immunocytochemistry. Analysis of antibody distribution in the aged Tg2576 mouse brain revealed that antibody 19.3 was associated with thioflavin S-positive amyloid plaques in the brain (FIGS. 13C and 13D). These data provided the first evidence that antibody 19.3 was able to penetrate into the transgenic mouse brain and bind to Aβ species of interest.

Plaque Deposition Model.

To further assess the ability of anti-ADDL antibody 19.3 to abate ADDL deposition into amyloid plaques in the brain, twelve month-old male Tg2576 mice (Taconic, N.Y.) were unilaterally cannulated weekly and bADDLs (50 pmol/μl) infused weekly for four weeks into the hippocampus (FIG. 14A). One week after the last bADDL treatment, half of the mice (n=5/treatment) were dosed (tail vein) weekly, for four weeks with PBS, while the remaining animals were dosed weekly with 200 μg of anti-ADDL antibody (about 8 mg/kg). All animals were euthanized one week after the last treatment and their brains processed for immuno-cytochemistry. For the detection of bADDL and plaques, brain sections wee incubated with Streptavidin ALEXA FLUOR® 594 (Invitrogen, Carlsbad, Calif.), mounted onto slides and the plaques stained with thioflavin S. Fluorescent images of the plaques were then captured with a PERKINELMER Rapid Confocal Imager with ULTRAVIEW ERS software and the difference in plaque growth quantified. The details of this model have been described (Gaspar, et al. (2010) $Exp. Neurol.$ 223:394-400). After one month of treatment, a significant reduction in the deposition of new ADDLs into existing plaques was seen in animals treated with antibody 19.3 (FIG. 14C), when compared to animals treated with vehicle alone (FIG. 14B; Table 16).

In a second series of experiments animals were treated with bADDLs as above, however beginning one week after the last bADDL injection, animals received 4 weekly IV injections of an anti-ADDL antibody (3B3, the murine progenitor of antibody 19.3). The effects of 3B3 were compared with that of antibody m266, an Aβ monomer selective antibody (Yamada, et al. (2009) $J. Neurosci.$ 29:11393-8), or vehicle. Animals were euthanized one week following the last injection of antibody and brain tissue was analyzed for β-amyloid plaque as above. The results of this study demonstrate that an anti-ADDL antibody can penetrate the brain, prevent bADDL deposition around plaques, and suppress accumulation of new β-amyloid plaque growth deposits surrounding the bADDL halos, while treatment with an Aβ monomer selective antibody did not suppress β-amyloid plaque growth (Table 17).

TABLE 17

| Treatment | Growth Relative to Baseline |
| --- | --- |
| anti-ADDL antibody | 0.46 |
| m266 | 1.27 |
| PBS | 1.19 |

In the mice receiving only bADDL infusions, without anti-ADDL antibody treatment, a positive 3B3 signal reflecting the presence of biotinylated Aβ appeared as a halo surrounding thioflavin-S positive dense core plaques or as separate bADDL deposits not associated with existing plaques at Week 4. At Week 8, additional ThioS-positive deposition was observed surrounding Week 4 biotinylated Aβ coated dense core plaques or bADDL deposited plaques. These results showed further accumulation of growth of β-amyloid plaques during the one-month bADDL treatment period, and continued growth of β-amyloid plaques following termination of biotinylated Aβ treatment due to endogenously produced Aβ. Treatment of the mice with anti-ADDL antibodies significantly reduced the halo surrounding biotinylated Aβ positive plaques, indicating that antibody treatment effectively prevented further growth of the β-amyloid plaques. This data demonstrate that IV treatment with an anti-ADDL antibody is effective in reducing biological effects of ADDLs within the brain.

One month of treatment with anti-ADDL antibody 3B3 significantly reduced the further growth of β-Amyloid plaques when compared to animals treated with vehicle alone (Table 17) or an Aβ monomer selective antibody. These results show that an anti-ADDL antibody can penetrate into the brain, sequester ADDLs, and abate the further growth of β-amyloid plaques.

Minimal Efficacious Dose.

To determine a minimal efficacious dose, Tg2576 mice (7 month old) received a single IV injection of antibody 19.3 and were taken for analysis of antibody 19.3:ADDL complexes in the brain after 24 hour using the sandwich ELISA assay described in Example 11. Single IV injections of antibody 19.3 in male and female mice resulted in a dose-dependent increase in the level of antibody 19.3:ADDL complexes in the brain (FIG. 15) and direct evidence for target engagement. In addition, this study identified 10 mg/kg as minimal effective dose (MED) to significantly elevate antibody 19.3:ADDL complexes in the brain. As such, a dose of 0.8 mg/kg (56 mg for an individual weighing 70 kg) would be the Human Equivalent Dose (HED) of the MED based on allometric scaling (conversion factor 0.08 from mouse to human; FDA Guidance Document UCM078932).

The methodology used in this study provided an opportunity to measure the levels of ADDLs in the brain. Levels of antibody 19.3:ADDL complexes in brain extracts were compared with a standard curved based on such complexes formed in vitro. Concentrations of approximately nM ADDLs were present in the brains of 7-9 months old Tg2576 mice. Given the levels of antibody that can be achieved via IV and SC injection, the amount of anti-ADDL antibodies are approximately an order of magnitude higher than the levels of ADDLs in the brain. Therefore, the antibodies of this invention are of use in the treatment of a disease associated with or resulting from the accumulation of soluble oligomer amyloid beta 1-42.

Example 13

Activity of 19.3 Antibody in Hippocampal Slices

In rodent hippocampal slice preparations, synaptic binding of ADDLs leads to rapid blockage of long-term potentiation (LTP) (Rammes, et al. (2011) $Neuropharmacol.$ 60:982-990), and injection of various soluble Aβ oligomer preparations directly into the rodent brain leads to impaired cognitive function (Reed, et al. (2011) $Neurobiol.\ Aging$ 32:1784-1794). Therefore, it was determined whether murine 3B3 could reverse ADDL impairment of LTP in this model. Antibody 3B3, the parent of 19.3, was used in this analysis as it is the murine version of humanized 19.3. Electrophysiological recordings were carried out as described by Rammes, et al. ((2011) supra). Briefly, murine hippocampal slices were perfused with oligomeric Aβ1-42 (50 nM), 3B3 antibody (500 pM) or oligomeric Aβ1-42+3B3 antibody. Twenty minutes after perfusion, high frequency stimulation (100 Hz/1 s) was used to induce LTP and field excitatory postsynaptic potential (fEPSPs) slopes were recorded. This analysis indicated that murine 3B3 reversed acute ADDL impairment of LTP in murine hippocampal slices (FIG. 16).

Example 14

Effect of Antibody 19.3 on Behavior in a Model of AD

Studies in animals and the theoretical considerations based on known functions of soluble Aβ oligomers indicate that behavioral benefits should manifest acutely with measurable impact within days and weeks of initial treatment. To analyze the acute effect of antibody 19.3 in a mouse model of AD, in vivo efficacy was evaluated using a locomotor activity behavioral assay. Increases in open-field locomotor activity in Tg2576 mice relative to control animals has been previously described as a behavioral readout of Alzheimer pathology in these animals (Gil-Bea, et al. (2007) *Behavioral Neurosci.* 121:340-4; King & Arendash (2002) *Physiol. Behavior* 75:627-42). In this study Tg2576 (8-9 month old) and wild-type mice were treated with a single dose of antibody 19.3 (30 mg/kg) or vehicle control, and locomotor activity (LMA) was tested at baseline prior to dosing and again at Days 7, 14, and 21 post-dosing. The locomotor activity (total distance travelled) was measured as an average of 10 minute time intervals over a 30 minute time period using a video tracking system. Tg2576 mice treated with IgG vehicle showed a significant increase of locomotor activity after 14 days post-injection as measured by the distance traveled over a 30 minute period. This increase was not observed in wild-type mice. Treatment of Tg2576 mice with antibody 19.3 reduced the LMA at Day 14 and Day 21 post-injection relative to the vehicle control group and reverted it to the level seen in non-transgenic control animals. The results are shown in FIG. 17. The data of the behavioral study provide evidence that IV administration of antibody 19.3 is able to alter behavior of the Tg2576 transgenic animals and is therefore useful in the treatment of AD.

A contextual fear conditioning model can also be used to assess behavior. Contextual fear conditioning is the most basic of the conditioning procedures. It involves taking an animal (e.g., a Tg2576 mouse) and placing it in a novel environment, providing an aversive stimulus, and then removing it. When the animal is returned to the same environment, it generally will demonstrate a freezing response if it remembers and associates that environment with the aversive stimulus. Freezing is a species-specific response to fear, which has been defined as "absence of movement except for respiration." This may last for seconds to minutes depending on the strength of the aversive stimulus, the number of presentations, and the degree of learning achieved by the subject. See Curzon, et al. (2009) *Methods of Behavior Analysis in Neuroscience*, 2$^{nd}$ Ed., Buccafusco (Ed.), Boca Raton: CRC Press.

Example 15

Use of Antibody 19.3 in the Treatment of AD

A randomized, double blind, placebo controlled study can be carried out in subjects with mild to moderate AD (PET confirmed) with detectable levels of ADDLs in the CSF. The study population can be composed of men and women aged 45-90 who fulfill clinical criteria for Alzheimer's disease using the McKhann criteria (McKhann, et al. (2011) *Alzheimers Dement.* 7:263-9). The population can be enriched for people with disordered Aβ metabolism by requirements for a florbetapir F$^{18}$ PET scan demonstrating Aβ deposition; CSF with decreased Aβ$_{1-42}$, and detectable CSF soluble Aβ oligomers. Throughout the study, treatment can include three IV infusions administered at monthly intervals. Subjects in the study are provided a dose of 0.1, 0.3, 1.0, 3.0 or 10 mg/kg and are monitored for signs and/or symptoms of AD. In particular, CSF samples are taken and ADDL:Antibody 19.3 conjugates and CSF biomarkers (e.g., Aβ1-40, Aβ1/42, tau, and phosphotau) are measured. Moreover, cognitive tests such as CANTAB (i.e., Paired Associates Learning, Pattern Recognition Memory, Spatial Working Memory, Delayed Matching to Sample, Reaction Time and Rapid Visual Information Processing), Cogstate computerized tests, ADAS-Cog (Alzheimer's Disease Assessment Scale-cognitive subscale), MMSE (Mini-Mental State Examination), Repeatable Battery for the Assessment of Neuropsychological Status (RBANS), and/or NPI (Neuropsychiatric Inventory) are performed. Given the excellent pharmacokinetic and pharmacodynamic, blood-brain barrier penetration, and safety properties demonstrated herein, the results of human administration are expected to deliver acute symptomatic benefit to the subjects and chronic disease modification. Specifically, it is expected that reversal of ADDL-mediated disruption of synaptic activities will permit improved hippocampal activity, which will manifest clinically as improved memory and cognition. Therefore, unlike other anti-Aβ monoclonal antibodies, the anti-ADDL antibodies of this invention are anticipated to produce measurable symptomatic improvement after short term treatment and are therefore useful in the treatment of a disease associated with or resulting from the accumulation of soluble oligomer amyloid beta 1-42.

What is claimed is:

1. A method for treating a disease associated with or resulting from the accumulation of soluble oligomer amyloid beta 1-42 comprising administering to a subject in need thereof a dose of less than 10 mg/kg body weight of
   (a) an antibody, or antibody fragment thereof, which has an affinity for amyloid beta 1-42 oligomers compared to amyloid beta 1-40 monomers in a competitive binding assay of at least 500:1 and has:
   a light chain variable region comprising,
      (i) a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Asn, Ser, Thr, Ala, Asp or Glu and Xaa$_2$ is Asn, His, Gln, Ser, Thr, Ala, or Asp,
      (ii) a CDR2 having the sequence Lys-Ala-Ser-Xaa$_1$-Arg-Phe-Ser (SEQ ID NO:2), wherein Xaa$_1$ is Asn, Gln, Ser, Thr, or Ala, and
      (iii) a CDR3 having the sequence Phe-Gln-Gly-Ser-Xaa$_1$-Xaa$_2$-Xaa$_3$-Xaa$_4$-Xaa$_5$ (SEQ ID NO:3), wherein Xaa$_1$ is Arg, Lys or Tyr, Xaa$_2$ is Val or Ala, Xaa$_3$ is Pro or His, Xaa$_4$ is Ala, Pro, or Val, and Xaa$_5$ is Ser, Gly, Arg or Phe; and
   a heavy chain variable region comprising,
      (i) a CDR1 of SEQ ID NO:4,
      (ii) a CDR2 of SEQ ID NO:5, and
      (iii) a CDR3 of SEQ ID NO:6; or
   (b) an antibody, or antibody fragment thereof, which has an affinity for amyloid beta 1-42 oligomers compared to amyloid beta 1-40 monomers in a competitive binding assay of at least 500:1 and has:
   a light chain variable region comprising,
      (i) a CDR1 having the sequence Arg-Ser-Ser-Gln-Ser-Ile-Val-His-Ser-Xaa$_1$-Gly-Xaa$_2$-Thr-Tyr-Leu-Glu (SEQ ID NO:1), wherein Xaa$_1$ is Ser, Thr, Ala, Asp or Glu and Xaa$_2$ is Asn, His, Gln, Ser, Thr, Ala, or Asp,
      (ii) a CDR2 having the sequence Lys-Ala-Ser-Xaa$_1$-Arg-Phe-Ser (SEQ ID NO:2), wherein Xaa$_1$ is Asn, Gln, Ser, Thr, or Ala, and
      (iii) a CDR3 of SEQ ID NO:18; and
   a heavy chain variable region comprising,
      (i) a CDR1 of SEQ ID NO:4,
      (ii) a CDR2 of SEQ ID NO:5, and
      (iii) a CDR3 of SEQ ID NO:6,
so that the disease associated with or resulting from the accumulation of soluble oligomer amyloid beta 1-42 is treated.

* * * * *

SEQUENCE LISTING

```
<160> NUMBER OF SEQ ID NOS: 61

<210> SEQ ID NO 1
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Xaa denotes N, S, T, A, D or E;  or Xaa denotes
      T, A, D, or E.
```

```
<220> FEATURE:
<221> NAME/KEY: MISC_FEATURE
<222> LOCATION: (12)..(12)
<223> OTHER INFORMATION: Xaa denotes N, H, Q, S, T, A or D; or Xaa
      denotes T.

<400> SEQUENCE: 1

Arg Ser Ser Gln Ser Ile Val His Ser Xaa Gly Xaa Thr Tyr Leu Glu
1               5                   10                  15

<210> SEQ ID NO 2
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa denotes N, G, S, T or A; or Xaa denotes T.

<400> SEQUENCE: 2

Lys Ala Ser Xaa Arg Phe Ser
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa denotes R, K or Y.
<220> FEATURE:
<221> NAME/KEY: MISC_FEATURE
<222> LOCATION: (6)..(6)
<223> OTHER INFORMATION: Xaa denotes V, A or L.
<220> FEATURE:
<221> NAME/KEY: MISC_FEATURE
<222> LOCATION: (7)..(7)
<223> OTHER INFORMATION: Xaa denotes P, H or G.
<220> FEATURE:
<221> NAME/KEY: MISC_FEATURE
<222> LOCATION: (8)..(8)
<223> OTHER INFORMATION: Xaa denotes A, P or V.
<220> FEATURE:
<221> NAME/KEY: MISC_FEATURE
<222> LOCATION: (9)..(9)
<223> OTHER INFORMATION: Xaa denotes S, G, R or F.

<400> SEQUENCE: 3

Phe Gln Gly Ser Xaa Xaa Xaa Xaa Xaa
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Gly Phe Thr Phe Ser Ser Phe Gly Met His
1               5                   10

<210> SEQ ID NO 5
<211> LENGTH: 17
<212> TYPE: PRT
<213> ORGANISM: Artificial sequence
```

<220> FEATURE:
<223> OTHER INFORMATION: Synthetic peptide

<400> SEQUENCE: 5

Tyr Ile Ser Arg Gly Ser Ser Thr Ile Tyr Tyr Ala Asp Thr Val Lys
1               5                   10                  15

Gly

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Gly Ile Thr Thr Ala Leu Asp Tyr
1               5

<210> SEQ ID NO 7
<211> LENGTH: 117
<212> TYPE: PRT
<213> ORGANISM: Artificial sequence
<220> FEATURE:
<223> OTHER INFORMATION: Synthetic peptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Thr Thr Ala Leu Asp Tyr Trp Gly Gln Gly Thr Leu
            100                 105                 110

Val Thr Val Ser Ser
        115

<210> SEQ ID NO 8
<211> LENGTH: 71
<212> TYPE: PRT
<213> ORGANISM: Artificial sequence
<220> FEATURE:
<223> OTHER INFORMATION: Synthetic peptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Ser Arg Phe Thr Ile Ser Arg Asp Asn Ser
        35                  40                  45

Lys Asn Thr Leu Tyr Leu Gln Met Asn Ser Leu Arg Ala Glu Asp Thr
    50                  55                  60

```
Ala Val Tyr Tyr Cys Ala Arg
 65                  70

<210> SEQ ID NO 9
<211> LENGTH: 112
<212> TYPE: PRT
<213> ORGANISM: Artificial sequence
<220> FEATURE:
<223> OTHER INFORMATION: Synthetic peptide

<400> SEQUENCE: 9

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Gln Leu Leu Ile Tyr Lys Ala Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Arg Leu Gly Pro Ser Phe Gly Gln Gly Thr Lys Leu Glu Ile Leu
            100                 105                 110

<210> SEQ ID NO 10
<211> LENGTH: 70
<212> TYPE: PRT
<213> ORGANISM: Artificial sequence
<220> FEATURE:
<223> OTHER INFORMATION: Synthetic peptice

<400> SEQUENCE: 10

Asp Ile Val Met Thr Gln Ser Pro Leu Ser Leu Pro Val Thr Pro Gly
  1               5                  10                  15

Glu Pro Ala Ser Ile Ser Cys Trp Tyr Leu Gln Lys Pro Gly Gln Ser
             20                  25                  30

Pro Gln Leu Leu Ile Tyr Gly Val Pro Asp Arg Phe Ser Gly Ser Gly
         35                  40                  45

Ser Gly Thr Asp Phe Thr Leu Lys Ile Ser Arg Val Glu Ala Glu Asp
     50                  55                  60

Val Gly Val Tyr Tyr Cys
 65                  70

<210> SEQ ID NO 11
<211> LENGTH: 25
<212> TYPE: DNA
<213> ORGANISM: Artificial sequence
<220> FEATURE:
<223> OTHER INFORMATION: Synthetice oligonucleotide

<400> SEQUENCE: 11
tatggcttct agagatgtgg tgatg                                         25

<210> SEQ ID NO 12
<211> LENGTH: 82
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t

<400> SEQUENCE: 12
tgcagccacc gtacgcttga tctccagctt ggtgccctgg ccaaaggtgg ggggcacmnn    60
mnnmnnmnnm nngcagtagt ag                                            82

<210> SEQ ID NO 13
<211> LENGTH: 70
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 13
tgcagccacc gtacgcttga tctccagctt ggtgccctgg ccaaamnnmn nmnnmnnmnn    60
gctgccctgg                                                          70

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 14
aggcggccct cgaggaggtg cagc                                          24

<210> SEQ ID NO 15
<211> LENGTH: 83
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t

<400> SEQUENCE: 15
agaccgatgg gcccttggtg gaggcgctgg acacggtcac cagggtgccc tggccccamn    60
nmnnmnnmnn mnnggtgatg ccc                                            83

<210> SEQ ID NO 16
<211> LENGTH: 92
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (78)..(79)
<223> OTHER INFORMATION: n is a, c, g, or t
<220> FEATURE:
<221> NAME/KEY: misc_feature
<222> LOCATION: (81)..(82)
<223> OTHER INFORMATION: n is a, c, g, or t

<400> SEQUENCE: 16
agaccgatgg gcccttggtg gaggcgctgg acacggtcac cagggtgccc tggccccagt    60
agtccagmnn mnnmnnmnnm nnccgggcac ag                                  92

<210> SEQ ID NO 17
<211> LENGTH: 9
<212> TYPE: PRT
<213> ORGANISM: Artificial sequence
<220> FEATURE:
<223> OTHER INFORMATION: Synthetic peptide

<400> SEQUENCE: 17

Phe Gln Gly Ser His Val Pro Pro Thr
1               5

<210> SEQ ID NO 18
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 18

Phe Gln Gly Ser Arg Leu Gly Pro Ser
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Phe Gln Gly Ser Arg Val Pro Ala Ser
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Phe Gln Gly Ser Arg Val Pro Pro Gly
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic peptide

<400> SEQUENCE: 21

Phe Gln Gly Ser Lys Ala His Pro Ser
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

Phe Gln Gly Ser Tyr Ala Pro Pro Gly
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Phe Gln Gly Ser Arg Ala Pro Pro Phe
1               5

<210> SEQ ID NO 24
<211> LENGTH: 9
<212> TYPE: PRT
<213> ORGANISM: Artificial sequence
<220> FEATURE:
```

<223> OTHER INFORMATION: Synthetic peptide

<400> SEQUENCE: 24

Phe Gln Gly Ser Arg Val Pro Val Arg
1               5

<210> SEQ ID NO 25
<211> LENGTH: 95
<212> TYPE: PRT
<213> ORGANISM: Artificial sequence
<220> FEATURE:
<223> OTHER INFORMATION: Synthetic peptide

<400> SEQUENCE: 25

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

His Val Pro Pro Thr Phe Gly Gln Gly Thr Lys Leu Glu Ile Lys
                85                  90                  95

<210> SEQ ID NO 26
<211> LENGTH: 95
<212> TYPE: PRT
<213> ORGANISM: Artificial sequence
<220> FEATURE:
<223> OTHER INFORMATION: Synthetic peptide

<400> SEQUENCE: 26

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Arg Leu Gly Pro Ser Phe Gly Gln Gly Thr Lys Leu Glu Ile Lys
                85                  90                  95

<210> SEQ ID NO 27
<211> LENGTH: 95
<212> TYPE: PRT
<213> ORGANISM: Artificial sequence
<220> FEATURE:
<223> OTHER INFORMATION: Synthetic peptide

<400> SEQUENCE: 27

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
            35                  40                  45

Arg Phe Ser Gly Ser Gly Ser Gly Thr Asp Phe Thr Leu Lys Ile Ser
 50                  55                  60

Arg Val Glu Ala Glu Asp Val Gly Val Tyr Tyr Cys Phe Gln Gly Ser
 65                  70                  75                  80

Arg Val Pro Ala Ser Phe Gly Gln Gly Thr Lys Leu Glu Ile Lys
                85                  90                  95

<210> SEQ ID NO 28
<211> LENGTH: 95
<212> TYPE: PRT
<213> ORGANISM: Artificial sequence
<220> FEATURE:
<223> OTHER INFORMATION: Synthetic peptide

<400> SEQUENCE: 28

Pro Ala Ser Ile Ser Cys Arg Ser Ser Gln Ser Ile Val His Ser Asn
 1               5                  10                  15

Gly Asn Thr Tyr Leu Glu Trp Tyr Leu Gln Lys Pro Gly Gln Ser Pro
                20                  25                  30

Gln Leu Leu Ile Tyr Lys Ala Ser Asn Arg Phe Ser Gly Val Pro Asp
            35                  40                  45

Arg Phe Ser Gly Ser Gly Ser Gly Thr Asp Phe Thr Leu Lys Ile Ser
 50                  55                  60

Arg Val Glu Ala Glu Asp Val Gly Val Tyr Tyr Cys Phe Gln Gly Ser
 65                  70                  75                  80

Arg Val Pro Pro Gly Phe Gly Gln Gly Thr Lys Leu Glu Ile Lys
                85                  90                  95

<210> SEQ ID NO 29
<211> LENGTH: 95
<212> TYPE: PRT
<213> ORGANISM: Artificial sequence
<220> FEATURE:
<223> OTHER INFORMATION: Synthetic peptide

<400> SEQUENCE: 29

Pro Ala Ser Ile Ser Cys Arg Ser Ser Gln Ser Ile Val His Ser Asn
 1               5                  10                  15

Gly Asn Thr Tyr Leu Glu Trp Tyr Leu Gln Lys Pro Gly Gln Ser Pro
                20                  25                  30

Gln Leu Leu Ile Tyr Lys Ala Ser Asn Arg Phe Ser Gly Val Pro Asp
            35                  40                  45

Arg Phe Ser Gly Ser Gly Ser Gly Thr Asp Phe Thr Leu Lys Ile Ser
 50                  55                  60

Arg Val Glu Ala Glu Asp Val Gly Val Tyr Tyr Cys Phe Gln Gly Ser
 65                  70                  75                  80

Lys Ala His Pro Ser Phe Gly Gln Gly Thr Lys Leu Glu Ile Lys
                85                  90                  95

<210> SEQ ID NO 30
<211> LENGTH: 95
<212> TYPE: PRT
<213> ORGANISM: Artificial sequence
<220> FEATURE:
<223> OTHER INFORMATION: Synthetic peptide

<400> SEQUENCE: 30

Pro Ala Ser Ile Ser Cys Arg Ser Ser Gln Ser Ile Val His Ser Asn

```
                1               5                   10                  15
            Gly Asn Thr Tyr Leu Glu Trp Tyr Leu Gln Lys Pro Gly Gln Ser Pro
                            20                  25                  30

Gln Leu Leu Ile Tyr Lys Ala Ser Asn Arg Phe Ser Gly Val Pro Asp
                            35                  40                  45

Arg Phe Ser Gly Ser Gly Ser Gly Thr Asp Phe Thr Leu Lys Ile Ser
                    50                  55                  60

Arg Val Glu Ala Glu Asp Val Gly Val Tyr Tyr Cys Phe Gln Gly Ser
            65                  70                  75                  80

Tyr Ala Pro Pro Gly Phe Gly Gln Gly Thr Lys Leu Glu Ile Lys
                            85                  90                  95

<210> SEQ ID NO 31
<211> LENGTH: 95
<212> TYPE: PRT
<213> ORGANISM: Artificial sequence
<220> FEATURE:
<223> OTHER INFORMATION: Synthetic peptide

<400> SEQUENCE: 31

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
                20                  25                  30

Gln Leu Leu Ile Tyr Lys Ala Ser Asn Arg Phe Ser Gly Val Pro Asp
            35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Arg Ala Pro Pro Phe Phe Gly Gln Gly Thr Lys Leu Glu Ile Lys
                85                  90                  95

<210> SEQ ID NO 32
<211> LENGTH: 95
<212> TYPE: PRT
<213> ORGANISM: Artificial sequence
<220> FEATURE:
<223> OTHER INFORMATION: Synthetic peptide

<400> SEQUENCE: 32

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
                20                  25                  30

Gln Leu Leu Ile Tyr Lys Ala Ser Asn Arg Phe Ser Gly Val Pro Asp
            35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Arg Val Pro Val Arg Phe Gly Gln Gly Thr Lys Leu Glu Ile Lys
                85                  90                  95

<210> SEQ ID NO 33
<211> LENGTH: 981
<212> TYPE: DNA
<213> ORGANISM: Artificial sequence
<220> FEATURE:
```

<223> OTHER INFORMATION: Synthetic polynucleotide

<400> SEQUENCE: 33

```
gcatccacca agggcccatc cgtcttcccc ctggcgccct gctccaggag cacctccgag      60
agcacagccg ccctgggctg cctggtcaag gactacttcc ccgaaccggt gacggtgtcc     120
tggaactctg gcgccctgac ctctggcgtg cacaccttcc ctgctgtgct gcaatcctct     180
ggcctgtact ccctgtcctc tgtggtgaca gtgccatcct ccaacttcgg cacccagacc     240
tacacatgca atgtggacca caagccatcc aacaccaagg tggacaagac agtggagcgg     300
aagtgctgtg tggagtgccc cccatgccct gccccccctg tggctggccc atctgtgttc     360
ctgttccccc caagcccaa ggacaccctg atgatctccc ggacccctga ggtgacctgt      420
gtggtggtgg acgtgtccca tgaggaccct gaggtgcagt tcaactggta tgtggatggc     480
gtggaggtgc acaatgccaa gaccaagccc cgggaggagc agttcaactc caccttccgg     540
gtggtgtctg tgctgacagt ggtgcaccag gactggctga atggcaagga gtacaagtgc     600
aaggtgtcca acaagggcct gcctgccccc atcgagaaga ccatctccaa gaccaagggc     660
cagccccggg agccccaggt gtacaccctg cccccatccc gggaggagat gaccaagaac     720
caggtgtccc tgacctgcct ggtgaagggc ttctacccat ccgacattgc tgtggagtgg     780
gagtccaatg gccagcctga gaacaactac aagaccaccc cccccatgct ggactctgat     840
ggctccttct cctgtactc caagctgaca gtggacaagt cccggtggca gcagggcaat     900
gtgttctcct gctctgtgat gcatgaggcc ctgcacaacc actacaccca gaagtccctg     960
tccctgtccc ctggcaagtg a                                              981
```

<210> SEQ ID NO 34
<211> LENGTH: 326
<212> TYPE: PRT
<213> ORGANISM: Artificial sequence
<220> FEATURE:
<223> OTHER INFORMATION: Synthetic polypeptide

<400> SEQUENCE: 34

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                165                 170                 175
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 35
<211> LENGTH: 324
<212> TYPE: DNA
<213> ORGANISM: Artificial sequence
<220> FEATURE:
<223> OTHER INFORMATION: Synthetic polynucleotide

<400> SEQUENCE: 35
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                            324

<210> SEQ ID NO 36
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 37
<211> LENGTH: 57
<212> TYPE: DNA
<213> ORGANISM: Artificial sequence
<220> FEATURE:
<223> OTHER INFORMATION: Synthetic oligonucleotide

<400> SEQUENCE: 37
atggaatgga gctgggtctt tctcttcttc ctgtcagtaa ctacaggtgt ccactcg         57

<210> SEQ ID NO 38
<211> LENGTH: 19
<212> TYPE: PRT
<213> ORGANISM: Artificial sequence
<220> FEATURE:
<223> OTHER INFORMATION: Synthetic peptide

<400> SEQUENCE: 38

Met Glu Trp Ser Trp Val Phe Leu Phe Phe Leu Ser Val Thr Thr Gly
1               5                   10                  15

Val His Ser

<210> SEQ ID NO 39
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 39
atgagtgtgc ccactcaggt cctggggttg ctgctgctgt ggcttacaga tgccagatgc      60

<210> SEQ ID NO 40
<211> LENGTH: 20
<212> TYPE: PRT
<213> ORGANISM: Artificial sequence
<220> FEATURE:
<223> OTHER INFORMATION: Synthetic peptide

<400> SEQUENCE: 40

Met Ser Val Pro Thr Gln Val Leu Gly Leu Leu Leu Leu Trp Leu Thr
1               5                   10                  15

Asp Ala Arg Cys
            20

<210> SEQ ID NO 41
<211> LENGTH: 16
<212> TYPE: PRT
<213> ORGANISM: Artificial sequence
<220> FEATURE:
<223> OTHER INFORMATION: Synthetic peptide

<400> SEQUENCE: 41

Arg Ser Ser Gln Ser Ile Val His Ser Asn Gly Asn Thr Tyr Leu Glu
1               5                   10                  15

<210> SEQ ID NO 42
<211> LENGTH: 16
<212> TYPE: PRT
<213> ORGANISM: Artificial sequence

```
<220> FEATURE:
<223> OTHER INFORMATION: Synthetic peptide

<400> SEQUENCE: 42

Arg Ser Ser Gln Ser Ile Val His Ser Ser Gly Asn Thr Tyr Leu Glu
1               5                   10                  15

<210> SEQ ID NO 43
<211> LENGTH: 16
<212> TYPE: PRT
<213> ORGANISM: Artificial sequence
<220> FEATURE:
<223> OTHER INFORMATION: Synthetic peptide

<400> SEQUENCE: 43

Arg Ser Ser Gln Ser Ile Val His Ser Thr Gly Asn Thr Tyr Leu Glu
1               5                   10                  15

<210> SEQ ID NO 44
<211> LENGTH: 16
<212> TYPE: PRT
<213> ORGANISM: Artificial sequence
<220> FEATURE:
<223> OTHER INFORMATION: Synthetic peptide

<400> SEQUENCE: 44

Arg Ser Ser Gln Ser Ile Val His Ser Ala Gly Asn Thr Tyr Leu Glu
1               5                   10                  15

<210> SEQ ID NO 45
<211> LENGTH: 16
<212> TYPE: PRT
<213> ORGANISM: Artificial sequence
<220> FEATURE:
<223> OTHER INFORMATION: Synthetic peptide

<400> SEQUENCE: 45

Arg Ser Ser Gln Ser Ile Val His Ser Glu Gly Asn Thr Tyr Leu Glu
1               5                   10                  15

<210> SEQ ID NO 46
<211> LENGTH: 16
<212> TYPE: PRT
<213> ORGANISM: Artificial sequence
<220> FEATURE:
<223> OTHER INFORMATION: Synthetic peptide

<400> SEQUENCE: 46

Arg Ser Ser Gln Ser Ile Val His Ser Asp Gly Asn Thr Tyr Leu Glu
1               5                   10                  15

<210> SEQ ID NO 47
<211> LENGTH: 16
<212> TYPE: PRT
<213> ORGANISM: Artificial sequence
<220> FEATURE:
<223> OTHER INFORMATION: Synthetic peptide

<400> SEQUENCE: 47

Arg Ser Ser Gln Ser Ile Val His Ser Ser Gly Gln Thr Tyr Leu Glu
1               5                   10                  15

<210> SEQ ID NO 48
<211> LENGTH: 16
<212> TYPE: PRT
<213> ORGANISM: Artificial sequence
<220> FEATURE:
```

-continued

<223> OTHER INFORMATION: Synthetic peptide

<400> SEQUENCE: 48

Arg Ser Ser Gln Ser Ile Val His Ser Ser Gly Ser Thr Tyr Leu Glu
1               5                   10                  15

<210> SEQ ID NO 49
<211> LENGTH: 16
<212> TYPE: PRT
<213> ORGANISM: Artificial sequence
<220> FEATURE:
<223> OTHER INFORMATION: Synthetic peptide

<400> SEQUENCE: 49

Arg Ser Ser Gln Ser Ile Val His Ser Ser Gly Thr Thr Tyr Leu Glu
1               5                   10                  15

<210> SEQ ID NO 50
<211> LENGTH: 16
<212> TYPE: PRT
<213> ORGANISM: Artificial sequence
<220> FEATURE:
<223> OTHER INFORMATION: Synthetic peptide

<400> SEQUENCE: 50

Arg Ser Ser Gln Ser Ile Val His Ser Ser Gly Ala Thr Tyr Leu Glu
1               5                   10                  15

<210> SEQ ID NO 51
<211> LENGTH: 7
<212> TYPE: PRT
<213> ORGANISM: Artificial sequence
<220> FEATURE:
<223> OTHER INFORMATION: Synthetic peptide

<400> SEQUENCE: 51

Lys Ala Ser Asn Arg Phe Ser
1               5

<210> SEQ ID NO 52
<211> LENGTH: 7
<212> TYPE: PRT
<213> ORGANISM: Artificial sequence
<220> FEATURE:
<223> OTHER INFORMATION: Synthetic peptide

<400> SEQUENCE: 52

Lys Ala Ser Gln Arg Phe Ser
1               5

<210> SEQ ID NO 53
<211> LENGTH: 7
<212> TYPE: PRT
<213> ORGANISM: Artificial sequence
<220> FEATURE:
<223> OTHER INFORMATION: Synthetic peptide

<400> SEQUENCE: 53

Lys Ala Ser Ser Arg Phe Ser
1               5

<210> SEQ ID NO 54
<211> LENGTH: 7
<212> TYPE: PRT
<213> ORGANISM: Artificial sequence
<220> FEATURE:
<223> OTHER INFORMATION: Synthetic peptide

<400> SEQUENCE: 54

Lys Ala Ser Thr Arg Phe Ser
1               5

<210> SEQ ID NO 55
<211> LENGTH: 7
<212> TYPE: PRT
<213> ORGANISM: Artificial sequence
<220> FEATURE:
<223> OTHER INFORMATION: Synthetic peptide

<400> SEQUENCE: 55

Lys Ala Ser Ala Arg Phe Ser
1               5

<210> SEQ ID NO 56
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 326
<212> TYPE: PRT
<213> ORGANISM: Artificial sequence
<220> FEATURE:
<223> OTHER INFORMATION: Synthetic polypeptide

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Gly Lys
                325
```

<210> SEQ ID NO 58
<211> LENGTH: 327
<212> TYPE: PRT
<213> ORGANISM: Artificial sequence
<220> FEATURE:
<223> OTHER INFORMATION: Synthetic peptide

<400> SEQUENCE: 58

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 59
<211> LENGTH: 326
<212> TYPE: PRT
<213> ORGANISM: Artificial sequence
<220> FEATURE:
<223> OTHER INFORMATION: Synthetic polypeptide

<400> SEQUENCE: 59

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 60
<211> LENGTH: 354
<212> TYPE: DNA
<213> ORGANISM: Artificial sequence
<220> FEATURE:
<223> OTHER INFORMATION: Synthetic polynucleotide

```
<400> SEQUENCE: 60
gcttctagag atgtggtgat gacccagagc cccctgtccc tgcctgtgac ccctggcgag      60
cctgccagca tctcctgccg gagctcccag agcatcgtgc actccaatgg caacacctac    120
ctggagtggt acctgcagaa gcctggccag agcccccagc tgctgatcta caaggcttcc    180
aaccggttct ccggcgtgcc tgaccggttc agcggctccg gcagcggcac agacttcacc    240
ctgaagatca gccgggtgga ggctgaggat gtgggcgtct actactgctt ccagggcagc    300
cggcttggtc ctagttttgg ccagggcacc aagctggaga tcaagcgtac ggtg          354

<210> SEQ ID NO 61
<211> LENGTH: 351
<212> TYPE: DNA
<213> ORGANISM: Artificial sequence
<220> FEATURE:
<223> OTHER INFORMATION: Synthetic polynucleotide

<400> SEQUENCE: 61
gaggtgcagc tggtggagtc cggcggcggc ctggtgcagc ctggcggcag cctgcggctg     60
agctgtgctg cctctggctt caccttcagc tcctttggca tgcactgggt gcggcaggcc   120
cctggcaagg gcctggagtg ggtggcctac atcagccggg gctccagcac catctactat   180
gctgacacag tgaagggccg gttcaccatc agccgggaca tgccaagaa ctccctgtat    240 ctgcagatga acagcctgcg ggctgaggac acagcagtgt actactgtgc ccggggcatc   300
accacagccc tggactactg gggccagggc accctggtga ccgtgtccag c             351
```